(12) United States Patent
Philippon et al.

(10) Patent No.: US 8,771,279 B2
(45) Date of Patent: Jul. 8, 2014

(54) METHOD AND APPARATUS FOR PERFORMING AN OSTEOTOMY IN BONE

(75) Inventors: Marc J. Philippon, Vail, CO (US); Kelly Ammann, Boulder, CO (US); J. Michael Egan, Edwards, CO (US); Marc Prisant, legal representative, Edwards, CO (US); Bjorn N. Rindal, Chandler, AZ (US)

(73) Assignee: Arthrex, Inc., Naples, FL (US)

( * ) Notice: Subject to any disclaimer, the term of this patent is extended or adjusted under 35 U.S.C. 154(b) by 75 days.

(21) Appl. No.: 13/363,191

(22) Filed: Jan. 31, 2012

(65) Prior Publication Data

US 2012/0215225 A1  Aug. 23, 2012

Related U.S. Application Data

(63) Continuation-in-part of application No. 11/888,506, filed on Aug. 1, 2007, now Pat. No. 8,540,777, and a continuation-in-part of application No. 11/888,719, filed on Aug. 2, 2007, now abandoned, and a continuation-in-part of application No. 11/047,159, filed on Jan. 31, 2005, and a continuation-in-part of application No. 11/047,551, filed on Jan. 31, 2005, now Pat. No. 8,083,746, and a continuation-in-part of application No. 11/350,333, filed on Feb. 8, 2006, now Pat. No. 8,496,662, and a continuation-in-part of application No. 11/352,103, filed on Feb. 9, 2006, now Pat. No. 8,211,112, and a continuation-in-part of application No. 11/396,490, filed on Apr. 3, 2006, and a continuation-in-part of application No. 11/607,321, filed on Dec. 1, 2006, now Pat. No. 7,967,823, and a continuation-in-part of application No. 11/644,218, filed on Dec. 22, 2006, now Pat. No. 7,935,119.

(60) Provisional application No. 61/437,892, filed on Jan. 31, 2011, provisional application No. 60/835,172, filed on Aug. 2, 2006, provisional application No. 60/835,269, filed on Aug. 3, 2006, provisional application No. 60/835,292, filed on Aug. 3, 2006, provisional application No. 60/835,268, filed on Aug. 3, 2006, provisional application No. 60/847,527, filed on Sep. 27, 2006, provisional application No. 60/860,595, filed on Nov. 22, 2006.

(51) Int. Cl.
  *A61B 17/56* (2006.01)
(52) U.S. Cl.
  USPC .......................................................... 606/87
(58) Field of Classification Search
  CPC ........................................................ A61F 2/28
  USPC ......... 606/246, 282, 289, 291, 301, 305, 105, 606/86 R, 87–89; 623/17.11, 20.32, 20.35, 623/20.36; 411/114, 116, 122, 143, 193
  See application file for complete search history.

(56) References Cited

U.S. PATENT DOCUMENTS

| | | |
|---|---|---|
| 2,737,724 A | 3/1956 | Herz |
| 3,579,777 A | 5/1971 | Milewski |
| 3,750,652 A | 8/1973 | Sherwin |
| 4,349,018 A | 9/1982 | Chambers |
| 4,421,112 A | 12/1983 | Mains et al. |
| 4,501,268 A | 2/1985 | Comparetto |
| 4,509,511 A | 4/1985 | Neufeld |
| 4,523,587 A | 6/1985 | Frey |
| 4,563,489 A | 1/1986 | Urist |
| 4,565,191 A | 1/1986 | Slocum |
| 4,750,481 A | 6/1988 | Reese |
| 4,769,040 A | 9/1988 | Wevers |
| 4,817,794 A | 4/1989 | Workman |
| 4,851,005 A | 7/1989 | Hunt et al. |
| 4,852,558 A | 8/1989 | Outerbridge |
| 4,936,844 A | 6/1990 | Chandler et al. |
| 5,053,039 A | 10/1991 | Hofmann et al. |
| 5,254,119 A | 10/1993 | Schreiber |
| 5,259,398 A | 11/1993 | Vrespa |
| 5,275,603 A | 1/1994 | Ferrante et al. |
| 5,297,538 A | 3/1994 | Daniel |
| 5,306,276 A | 4/1994 | Johnson et al. |
| 5,352,229 A | 10/1994 | Goble et al. |
| 5,413,579 A | 5/1995 | Tom Du Toit |
| 5,445,640 A | 8/1995 | Johnson et al. |
| 5,451,228 A | 9/1995 | Johnson et al. |

Captive Anchor Implant System

| | | |
|---|---|---|
| 5,540,695 A | 7/1996 | Levy |
| 5,569,250 A | 10/1996 | Sarver et al. |
| 5,601,565 A | 2/1997 | Huebner |
| 5,609,635 A | 3/1997 | Michelson |
| 5,613,969 A | 3/1997 | Jenkins, Jr. |
| 5,620,448 A | 4/1997 | Puddu |
| 5,640,813 A | 6/1997 | Glazik et al. |
| 5,643,272 A | 7/1997 | Haines et al. |
| 5,662,655 A | 9/1997 | Laboureau et al. |
| 5,669,909 A | 9/1997 | Zdeblick et al. |
| 5,674,296 A | 10/1997 | Bryan et al. |
| 5,681,316 A | 10/1997 | DeOrio et al. |
| 5,722,978 A | 3/1998 | Jenkins, Jr. |
| 5,733,290 A | 3/1998 | McCue et al. |
| 5,749,875 A | 5/1998 | Puddu |
| 5,766,251 A | 6/1998 | Koshino |
| 5,843,085 A | 12/1998 | Graser |
| 5,888,223 A | 3/1999 | Bray, Jr. |
| 5,911,724 A | 6/1999 | Wehrli |
| 5,935,128 A | 8/1999 | Carter et al. |
| 5,980,526 A | 11/1999 | Johnson et al. |
| 6,008,433 A | 12/1999 | Stone |
| 6,027,504 A | 2/2000 | McGuire |
| 6,039,761 A | 3/2000 | Li et al. |
| 6,086,593 A | 7/2000 | Bonutti |
| 6,099,531 A | 8/2000 | Bonutti |
| 6,102,950 A | 8/2000 | Vaccaro |
| 6,190,390 B1 | 2/2001 | McAllister |
| 6,200,347 B1 | 3/2001 | Anderson et al. |
| 6,203,546 B1 | 3/2001 | MacMahon |
| 6,224,599 B1 | 5/2001 | Baynham et al. |
| 6,277,149 B1 | 8/2001 | Boyle et al. |
| 6,287,308 B1 | 9/2001 | Betz et al. |
| 6,379,361 B1 | 4/2002 | Beck, Jr. et al. |
| 6,423,063 B1 | 7/2002 | Bonutti |
| 6,461,359 B1 | 10/2002 | Tribus et al. |
| 6,478,800 B1 | 11/2002 | Fraser et al. |
| 6,565,570 B2 | 5/2003 | Sterett et al. |
| 6,575,982 B1 | 6/2003 | Bonutti |
| 6,755,841 B2 | 6/2004 | Fraser et al. |
| 6,796,986 B2 | 9/2004 | Duffner |
| 6,823,871 B2 | 11/2004 | Schmieding |
| 2002/0010513 A1 | 1/2002 | Schmieding |
| 2002/0029084 A1 | 3/2002 | Paul et al. |
| 2002/0095156 A1 | 7/2002 | Kuras et al. |
| 2002/0165552 A1 | 11/2002 | Duffner |
| 2003/0028197 A1 | 2/2003 | Hanson et al. |
| 2003/0105526 A1 | 6/2003 | Bryant et al. |
| 2003/0171757 A1 | 9/2003 | Coon et al. |
| 2003/0195516 A1 | 10/2003 | Sterett et al. |
| 2003/0199881 A1 | 10/2003 | Bonutti |
| 2004/0039387 A1 | 2/2004 | Gause et al. |
| 2004/0249377 A1 | 12/2004 | Kaes et al. |
| 2005/0033296 A1 | 2/2005 | Bono et al. |
| 2005/0075641 A1 | 4/2005 | Singhatat et al. |
| 2005/0149039 A1 | 7/2005 | Haines et al. |
| 2005/0216090 A1 | 9/2005 | O'Driscoll et al. |
| 2005/0228498 A1 | 10/2005 | Andres |
| 2005/0251147 A1 | 11/2005 | Novak |
| 2005/0273114 A1 | 12/2005 | Novak |
| 2005/0273115 A1 | 12/2005 | Coon et al. |
| 2006/0015109 A1 | 1/2006 | Haines |
| 2006/0106396 A1 | 5/2006 | Justin et al. |
| 2006/0122617 A1 | 6/2006 | Lavallee et al. |
| 2006/0129163 A1 | 6/2006 | McGuire |
| 2006/0149274 A1 | 7/2006 | Justin et al. |
| 2006/0149275 A1 | 7/2006 | Cadmus |
| 2006/0241636 A1 | 10/2006 | Novak et al. |
| 2007/0282341 A1 | 12/2007 | Hes et al. |
| 2008/0195097 A1 | 8/2008 | Eglseder |

FOREIGN PATENT DOCUMENTS

| | | |
|---|---|---|
| EP | 1 669 033 A1 | 6/2006 |
| FR | 2741525 A1 | 5/1997 |
| WO | WO 2005/048888 A1 | 6/2005 |
| WO | WO 2006/107800 A2 | 10/2006 |

OTHER PUBLICATIONS

Oliver C. Kessler et al., "Avoidance of Medial Cortical Fracture in High Tibial Osteotomy: Improved Technique," Clinical Orthopaedics and Related Research, No. 395, pp. 180-185, Feb. 2002.

*Primary Examiner* — Pedro Philogene
*Assistant Examiner* — David Comstock
(74) *Attorney, Agent, or Firm* — Dickstein Shapiro LLP

(57) ABSTRACT

A method and apparatus for forming an osteotomy in bone. The osteotomy opening is formed in a bone with a keyhole. A similarly configured implant is inserted into the opening with a key configured to engage the keyhole to provide stability and support to the osteotomy opening.

27 Claims, 89 Drawing Sheets

TOP VIEW

LATERAL VIEW UNDER FLUOROSCOPY, WITH GUIDE ELEMENT NOT VERTICALLY ALIGNED WITH FLUOROSCOPE

LATERAL VIEW UNDER FLUOROSCOPY, WITH GUIDE ELEMENT VERTICALLY ALIGNED WITH FLUOROSCOPE

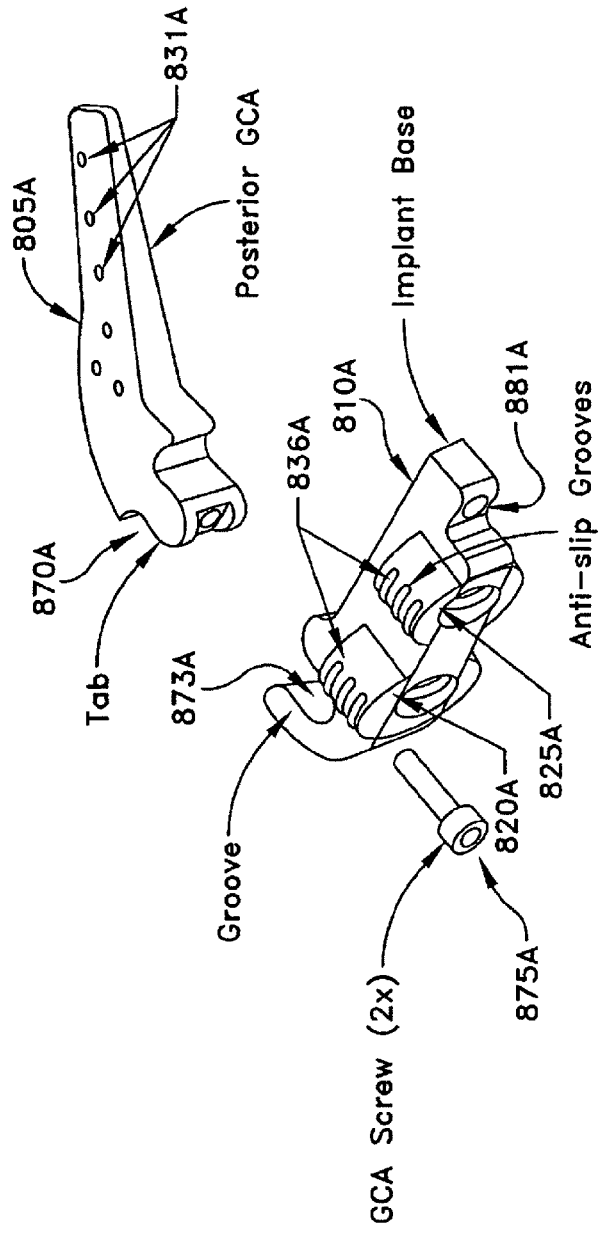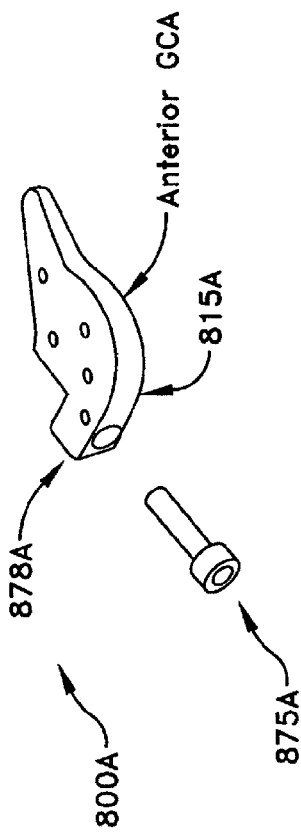
FIG. 32

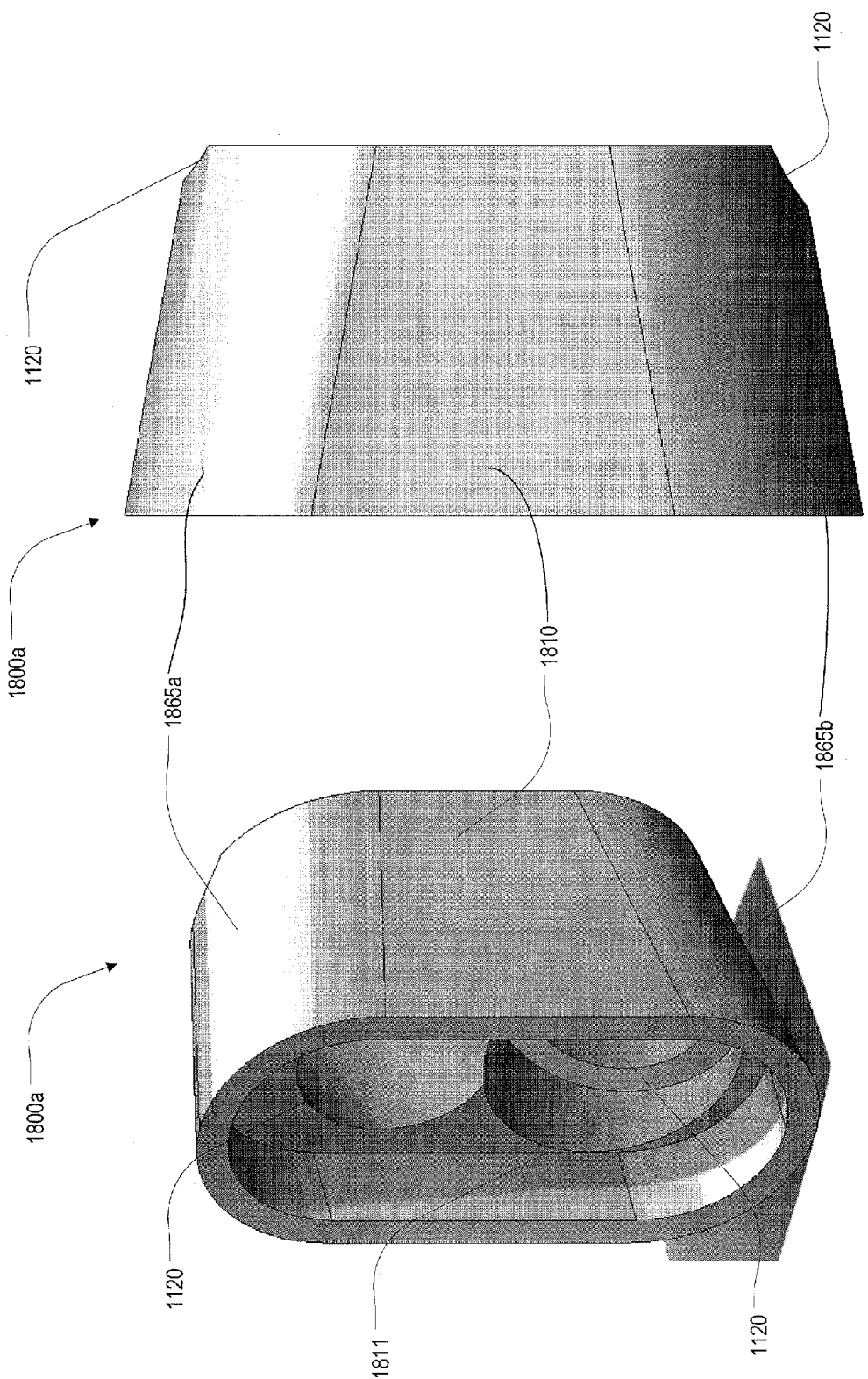

METHOD AND APPARATUS FOR PERFORMING AN OSTEOTOMY IN BONE

CROSS-REFERENCE TO RELATED APPLICATIONS

This patent application claims priority to U.S. Provisional Patent Application No. 61/437,892, filed Jan. 31, 2011, by Kelly G. Ammann et al. for OSTEOTOMY SYSTEM FOR REPOSITIONING OF THE SOCKET IN THE ANATOMIC BALL AND SOCKET JOINT.

This application is also a continuation-in-part of co-pending U.S. patent application Ser. No. 11/888,506 filed Aug. 1, 2007 by Kelly G. Ammann et al. for METHOD AND APPARATUS FOR PERFORMING AN OPEN WEDGE, HIGH TIBIAL OSTEOTOMY and U.S. patent application Ser. No. 11/888,719, filed Aug. 2, 2007 by Kelly G. Ammann et al. for METHOD AND APPARATUS FOR PERFORMING AN OPEN WEDGE, HIGH TIBIAL OSTEOTOMY, both of which in turn claim the benefit of the following provisionals:

U.S. Provisional Patent Application Ser. No. 60/835,172, filed Aug. 2, 2006 by Kelly G. Ammann et al. for METHOD AND SYSTEM OF FIXATION FOR PERFORMING AN OPENING WEDGE OSTEOTOMY;

U.S. Provisional Patent Application Ser. No. 60/835,269, filed Aug. 3, 2006 by Kelly G. Ammann et al. for METHOD AND SYSTEM OF FIXATION FOR PERFORMING AN OPENING WEDGE OSTEOTOMY;

U.S. Provisional Patent Application Ser. No. 60/835,292, filed Aug. 3, 2006 by Robert E. Schneider et al. for BONE ANCHOR FOR FIXATION TO A DISTAL CORTICAL WALL THROUGH CANCELLOUS BONE;

U.S. Provisional Patent Application Ser. No. 60/835,268, filed Aug. 3, 2006 by Kelly G. Ammann et al. for OPEN WEDGE OSTEOTOMY SYSTEM;

U.S. Provisional Patent Application Ser. No. 60/847,527, filed Sep. 27, 2006 by Vincent P. Novak et al. for KEYHOLE OSTEOTOMY SYSTEM; and U.S. Provisional Patent Application Ser. No. 60/860,595, filed Nov. 22, 2006 by Kelly Ammann et al. for METHOD AND APPARATUS FOR PERFORMING AN OPEN WEDGE, HIGH TIBIAL OSTEOTOMY.

This application is also a continuation-in-part of:

U.S. patent application Ser. No. 11/047,159, filed Jan. 31, 2005 by Vincent P. Novak for OPEN WEDGE OSTEOTOMY SYSTEM AND SURGICAL METHOD;

U.S. patent application Ser. No. 11/047,551, filed Jan. 31, 2005 by Vincent P. Novak for OPEN WEDGE OSTEOTOMY SYSTEM AND SURGICAL METHOD;

U.S. patent application Ser. No. 11/350,333, filed Feb. 8, 2006 by Vincent P. Novak et al. for METHOD AND APPARATUS FOR FORMING A WEDGE-LIKE OPENING IN A BONE FOR AN OPEN WEDGE OSTEOTOMY;

U.S. patent application Ser. No. 11/352,103, filed Feb. 9, 2006 by Vincent P. Novak et al. for MULTI-PART IMPLANT FOR OPEN WEDGE KNEE OSTEOTOMIES;

U.S. patent application Ser. No. 11/396,490, filed Apr. 3, 2006 by Kelly Ammann et al. for METHOD AND APPARATUS FOR PERFORMING AN OPEN WEDGE, HIGH TIBIAL OSTEOTOMY;

U.S. patent application Ser. No. 11/607,321, filed Dec. 1, 2006 by Kelly G. Ammann et al. for METHOD AND APPARATUS FOR PERFORMING AN OPEN WEDGE, HIGH TIBIAL OSTEOTOMY;

U.S. patent application Ser. No. 11/644,218, filed Dec. 22, 2006 by Kelly G. Ammann et al. for METHOD AND APPARATUS FOR PERFORMING AN OPEN WEDGE, HIGH TIBIAL OSTEOTOMY;

The above-identified patent applications are hereby incorporated by reference herein in their entirety.

FIELD OF THE INVENTION

This invention relates to surgical methods and apparatus in general, and more particularly to surgical methods and apparatus for performing osteotomies in bone.

BACKGROUND OF THE INVENTION

Osteotomies of the knee are an important technique for treating knee osteoarthritis. In essence, knee osteotomies adjust the geometry of the knee joint so as to transfer weight bearing load from arthritic portions of the joint to relatively unaffected portions of the joint.

Knee osteotomies are also an important technique for addressing abnormal knee geometries, e.g., due to birth defect, injury, etc.

Most knee osteotomies are designed to modify the geometry of the tibia, so as to adjust the manner in which the load is transferred across the knee joint.

There are essentially two ways in which to adjust the orientation of the tibia: (i) the closed wedge technique; and (ii) the open wedge technique.

With the closed wedge technique, a wedge of bone is removed from the upper portion of the tibia, and then the tibia is manipulated so as to close the resulting gap, whereby to reorient the lower portion of the tibia relative to the tibial plateau and hence adjust the manner in which load is transferred from the femur to the tibia.

With the open wedge technique, a cut is made into the upper portion of the tibia, the tibia is manipulated so as to open a wedge-like opening in the bone, and then the bone is secured in this position (e.g., by screwing metal plates to the bone or by inserting a wedge-shaped implant into the opening in the bone), whereby to reorient the lower portion of the tibia relative to the tibial plateau and hence adjust the manner in which load is transferred from the femur to the tibia.

While both closed wedge osteotomies and open wedge osteotomies provide substantial benefits to the patient, they are procedurally challenging for the surgeon. Among other things, with respect to open wedge osteotomies, it can be difficult to create the wedge-like opening in the bone with the necessary precision and with a minimum of trauma to the surrounding tissue (e.g., the neurological and vascular structures at the back of the knee). Furthermore, with open wedge osteotomies, it can be difficult to stabilize the upper and lower portions of the tibia relative to one another and to maintain them in this position while healing occurs.

The present invention is directed to osteotomies in bone, and is intended to provide increased precision and reduced trauma when creating the opening in the bone, and to provide increased stability to the upper and lower portions of the bone while healing occurs.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings.

FIGS. 31-33 are schematic views showing an alternative wedge-shaped implant also formed in accordance with the present invention.

FIGS. 80-81 show an implant for performing a spherical osteotomy.

DETAILED DESCRIPTION OF THE PREFERRED EMBODIMENTS

In the following detailed description, reference is made to the accompanying drawings, which form a part hereof and illustrate specific embodiments of the invention. These embodiments are described in sufficient detail to enable those skilled in the art to make and use them. It is to be understood that structural, logical, or procedural changes may be made to the specific embodiments disclosed without departing from the spirit and scope of the invention.

Overview of an Open Wedge, High Tibial Osteotomy

Figure 1:
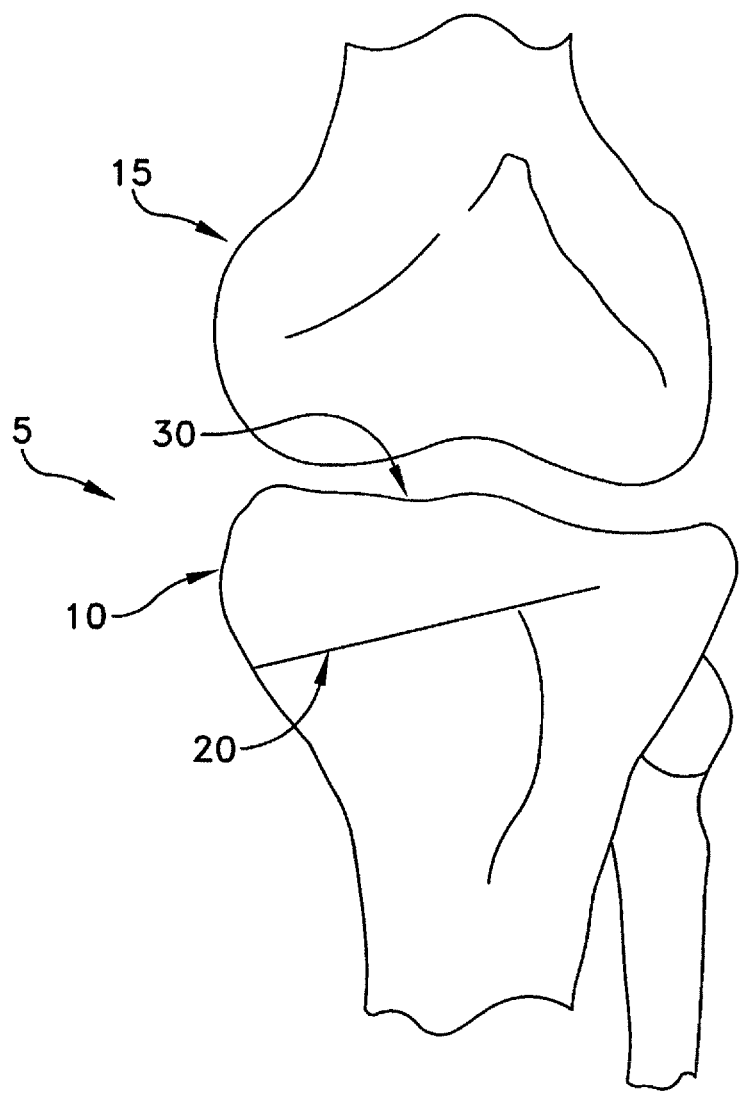
FIGS. 1-3 are schematic views showing the formation of a wedge-like opening in the tibia for an open wedge, high tibial osteotomy, and positioning of a wedge-shaped implant into the wedge-like opening in the tibia.
Figure 2:
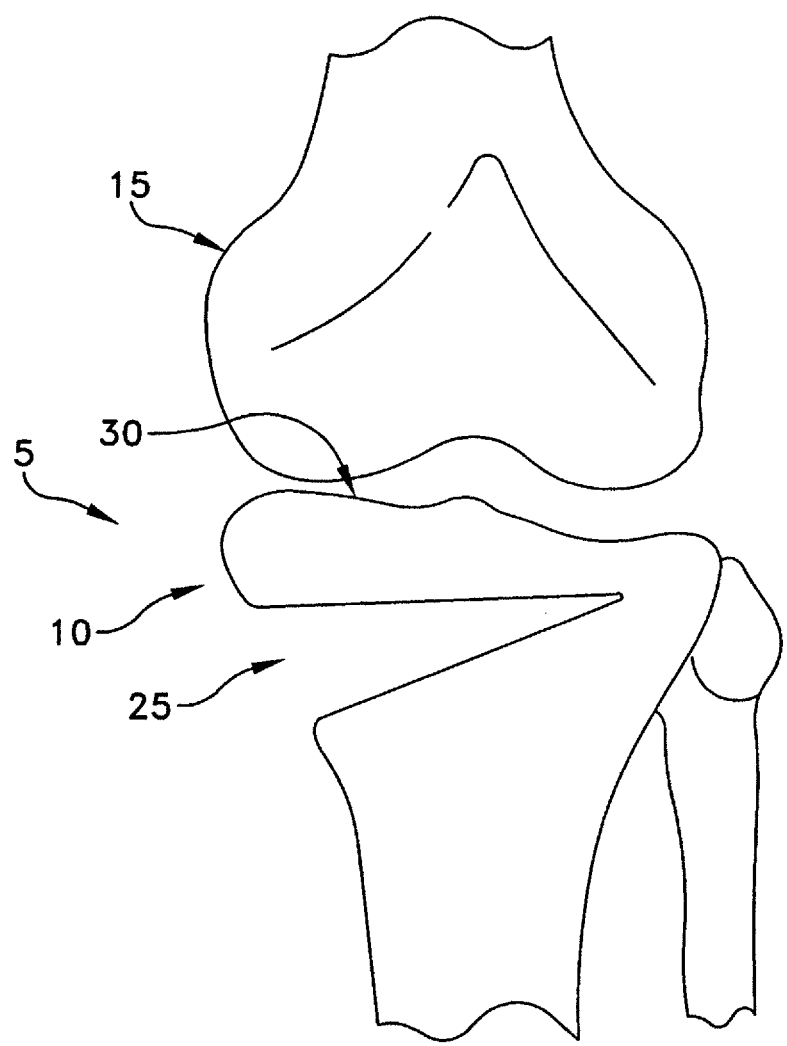
Figure 3:
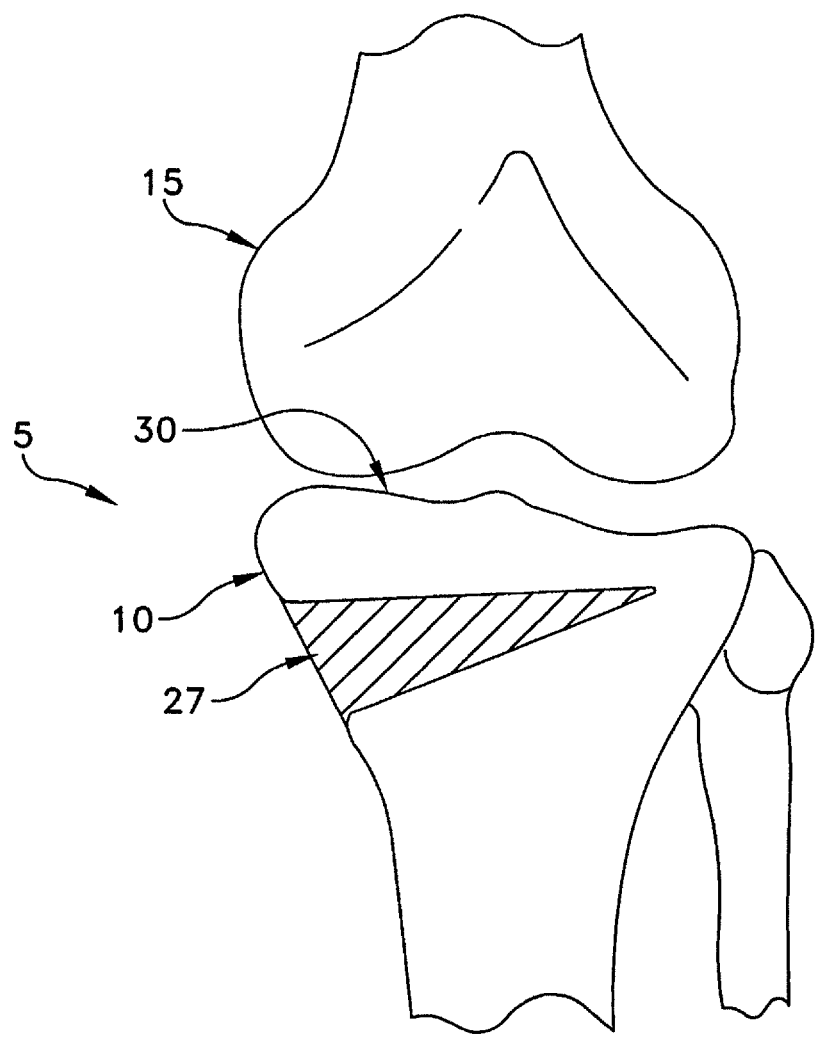

Looking first at FIGS. 1-3, there is shown a knee joint 5 upon which an open wedge osteotomy is to be performed. Knee joint 5 generally comprises a tibia 10 and a femur 15. In accordance with the present invention, the open wedge osteotomy is effected by first making a cut 20 (FIG. 1) into the upper tibia, and then manipulating the lower portion of the tibia so as to open a wedge-like opening 25 (FIG. 2) in the bone, with the wedge-like opening 25 being configured so as to adjust the manner in which load is transferred from the femur to the tibia. In this respect, it should be appreciated that a variety of methods are well known in the art for determining the degree of correction necessary to correctly re-align the weight-bearing axis of the knee. Furthermore, cut 20 and wedge-like opening 25 may be formed in a variety of ways well known in the art.

Among other things, the present invention provides a new and improved method and apparatus for forming cut 20 and wedge-like opening 25, as will be discussed in detail below.

Once the desired wedge-like opening 25 has been formed in tibia 10 so as to reconfigure tibia 10 to the desired geometry, the bone may be secured in position in a variety of ways well known in the art (e.g., by screwing metal plates to the bone or by inserting a wedge-shaped implant into the opening in the bone), whereby to adjust the manner in which the load is transferred from the femur to the tibia. By way of example, FIG. 3 shows a wedge-shaped implant 27 inserted into the wedge-like opening 25 formed in the tibia, whereby to stabilize the tibia in its reconfigured geometry.

Among other things, the present invention also provides a new and improved implant, and an associated method and apparatus for deploying the same at the wedge-shaped opening in the tibia, as will be discussed in detail below.

Figure 3A:
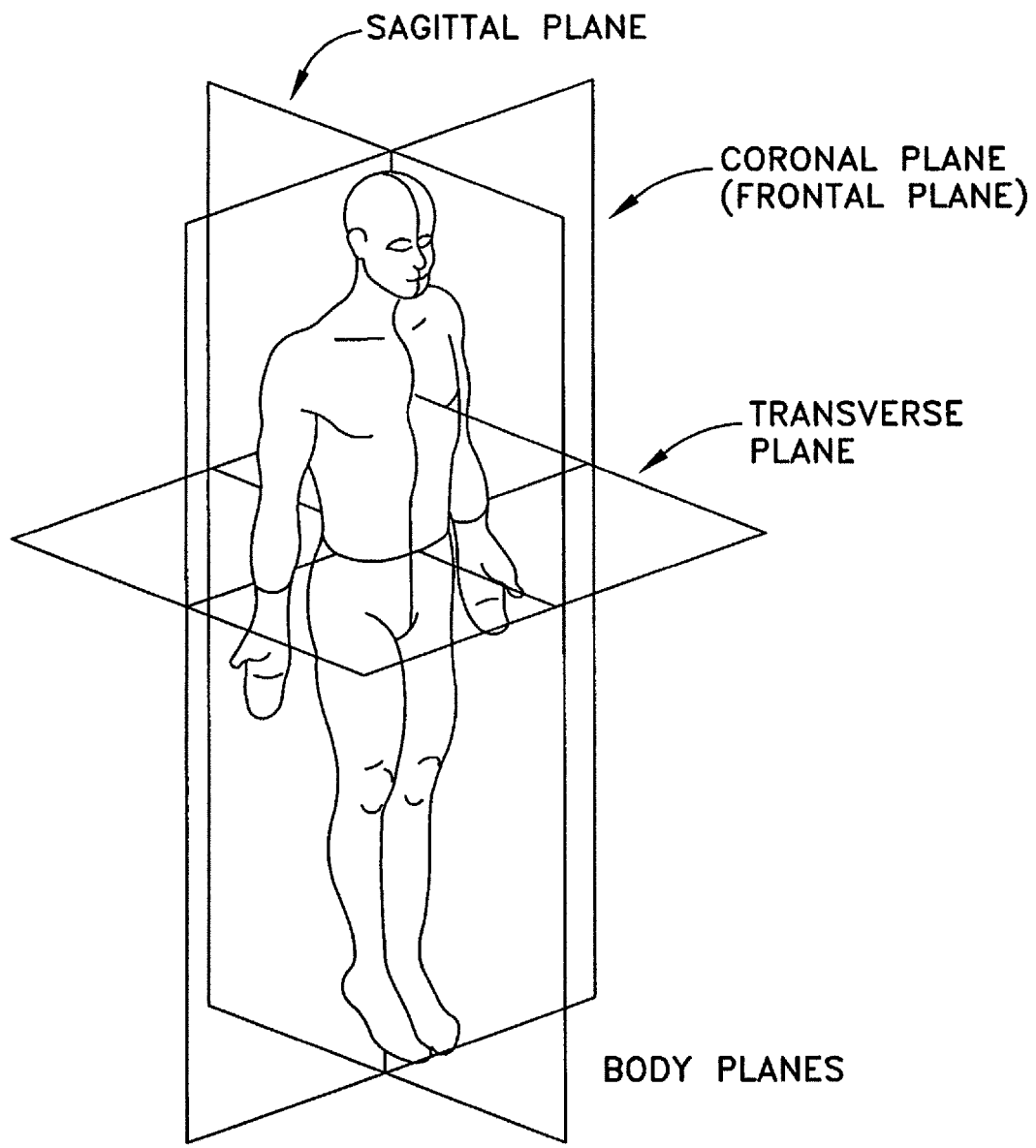
FIG. 3A is a schematic view showing selected anatomical planes.

Discussion of the Relevant Planar Surfaces in the Open Wedge, High Tibial Osteotomy of the Present Invention In order to appreciate certain aspects of the present invention, it is helpful to have a thorough understanding of the planar surfaces of the tibia that are relevant in performing the open wedge, high tibial osteotomy of the present invention. Thus, the following discussion presents a geometric description of the planar surfaces that are relevant to the open wedge, high tibial osteotomy of the present invention. For the purposes of the present discussion, it can sometimes be helpful to make reference to selected anatomical planes, e.g., the coronal plane, the sagittal plane and the transverse plane (FIG. 3A).

Figure 4:
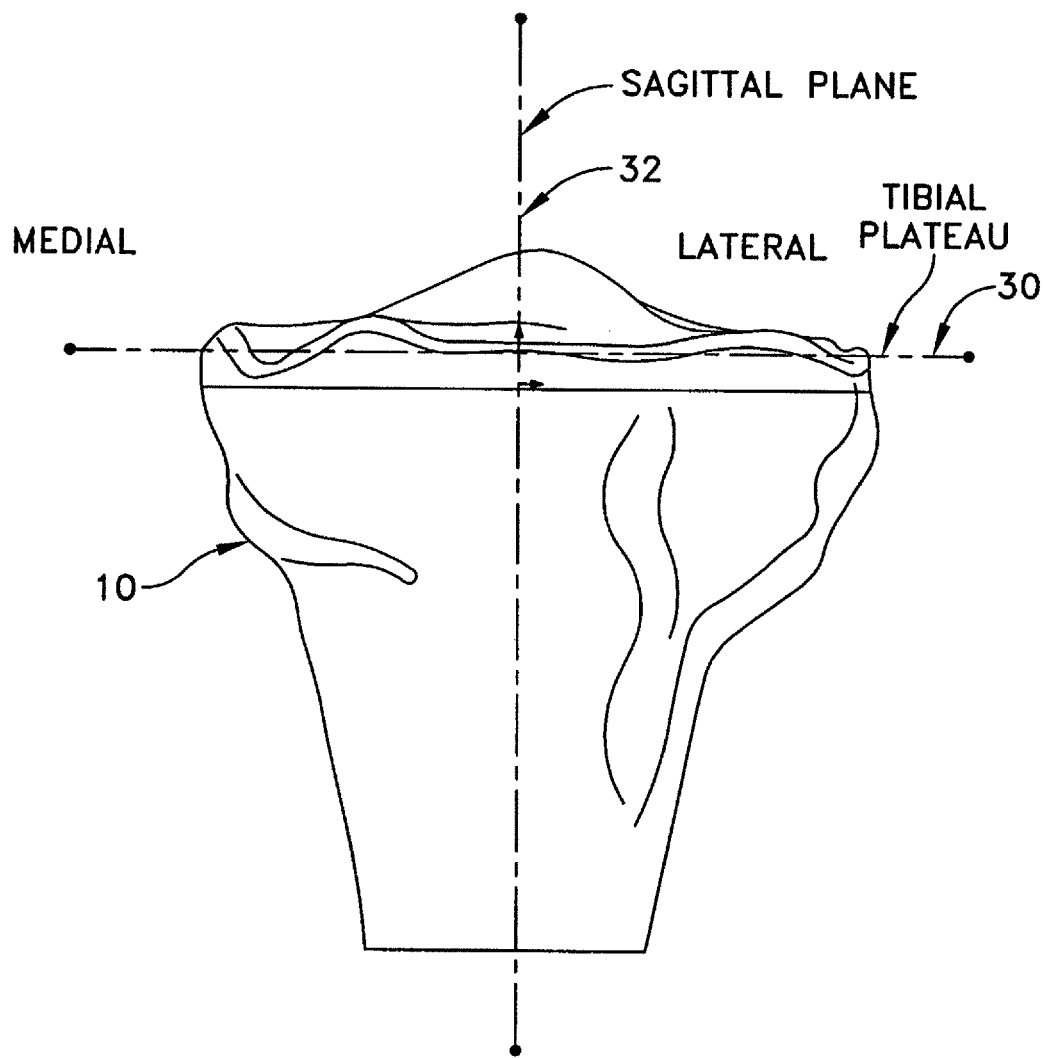
FIGS. 4-9 show the relevant planar surfaces in an open wedge, high tibial osteotomy conducted in accordance with the present invention.
Figure 5:
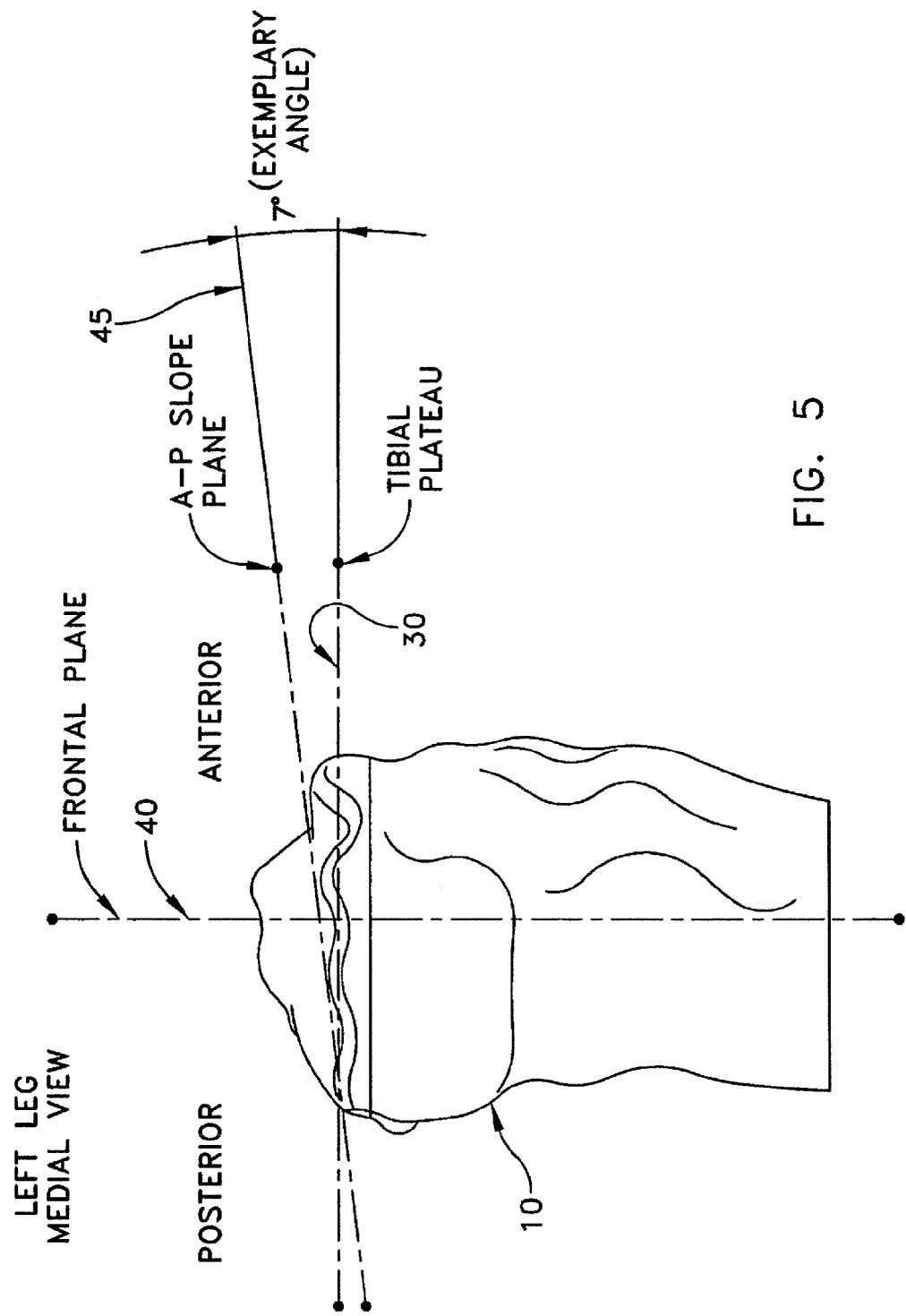

Looking now at FIGS. 1-4, for the purposes of the present invention, the tibial plateau 30 may be described as a horizontal (or transverse) plane that extends along the top surface of tibia 10. For reference, the sagittal plane 32 is also shown in FIG. 4. As seen in FIG. 5, tibial plateau 30 is also perpendicular to the frontal (or coronal) plane 40. The anterior-posterior (A-P) slope is defined by an anterior-posterior (A-P) slope plane 45 that extends along the sloping top surface of the tibia, from anterior-to-posterior. Published research has demonstrated that the anterior-posterior (A-P) slope typically extends at an angle of approximately 7° to 11° to the tibial plateau 30; however, the specific angle may vary from individual to individual.

Figure 6:
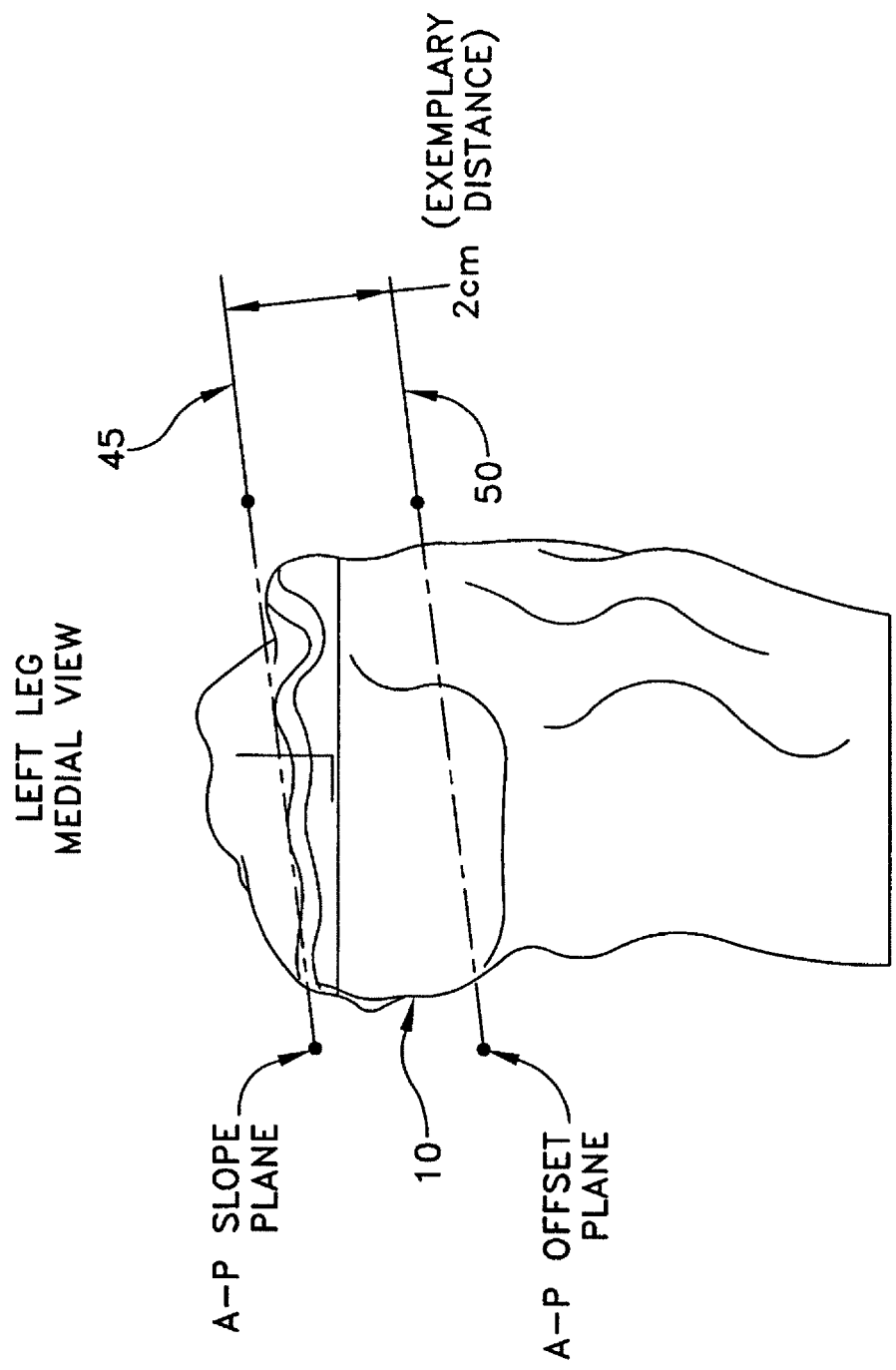

Looking next at FIG. 6, for the open wedge, high tibial osteotomy of the present invention, it is generally desirable to stay about 2 cm inferior to the A-P slope plane 45. This offset can be referred to as the A-P offset plane 50.

Figure 7:
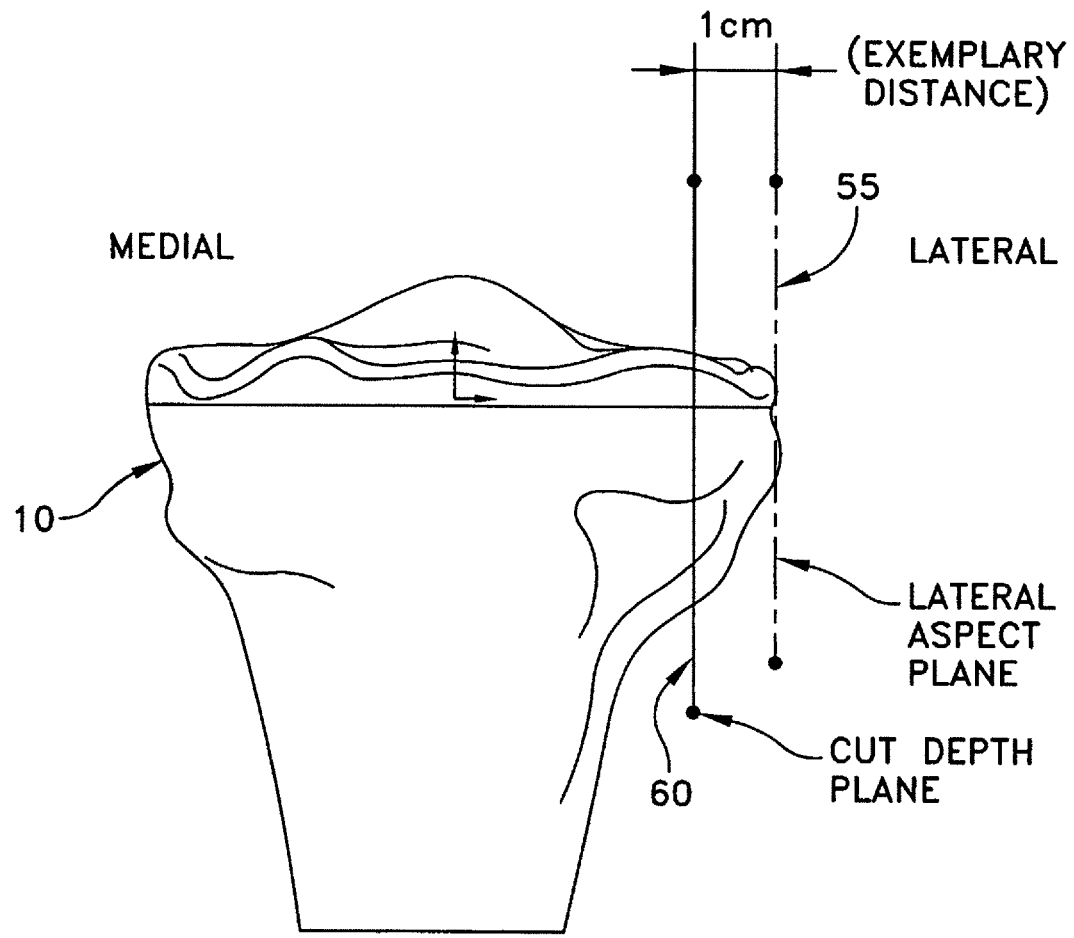

As seen in FIG. 7, the lateral aspect and cut depth of the cut 20 may be defined by a lateral aspect plane 55 and a cut depth plane 60, with the cut depth being about 1 cm medial to the lateral aspect of the tibia.

Figure 8:
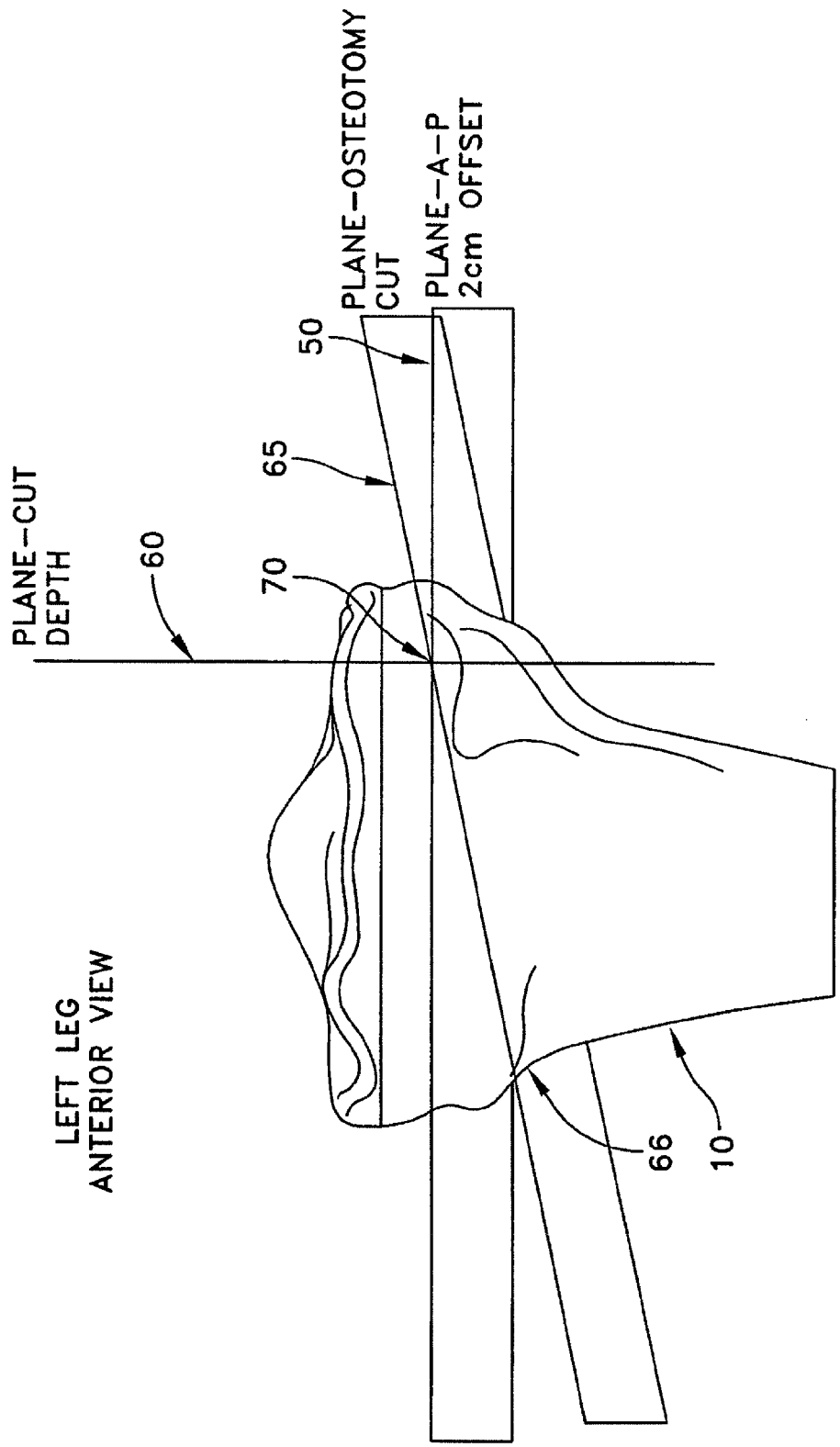

Looking next at FIG. 8, the osteotomy cut plane 65 (when seen from the direct frontal view of FIG. 8) is formed by a plane that is rotated away from the A-P offset plane 50 through an axis which is formed by the intersection of the cut depth plane 60 and the A-P offset plane 50. The degree of rotation is selected so as to be sufficient to place the entry of the osteotomy cut plane 65 at the medial neck 66 (FIG. 8) of the tibia. It should be noted that the A-P offset plane 50 and the osteotomy cut plane 65 are "tilted" slightly from anterior to posterior (but not seen in the direct frontal view of FIG. 8), since the A-P offset plane 50 and the osteotomy cut plane 65 follow the tilt of the A-P slope plane 45 (FIG. 6). The intersection of the A-P offset plane 50 and the cut depth plane 60 forms an axis 70 which, in accordance with the present invention, defines the lateral limit of the osteotomy cut 20. In other words, axis 70 defines a line through the tibia which is (i) parallel to A-P slope plane 45, and (ii) contained within osteotomy cut plane 65. Furthermore, in accordance with the present invention, axis 70 is used to define the lateral limit of the osteotomy cut 20 which is to be made into the tibia.

Figure 9:
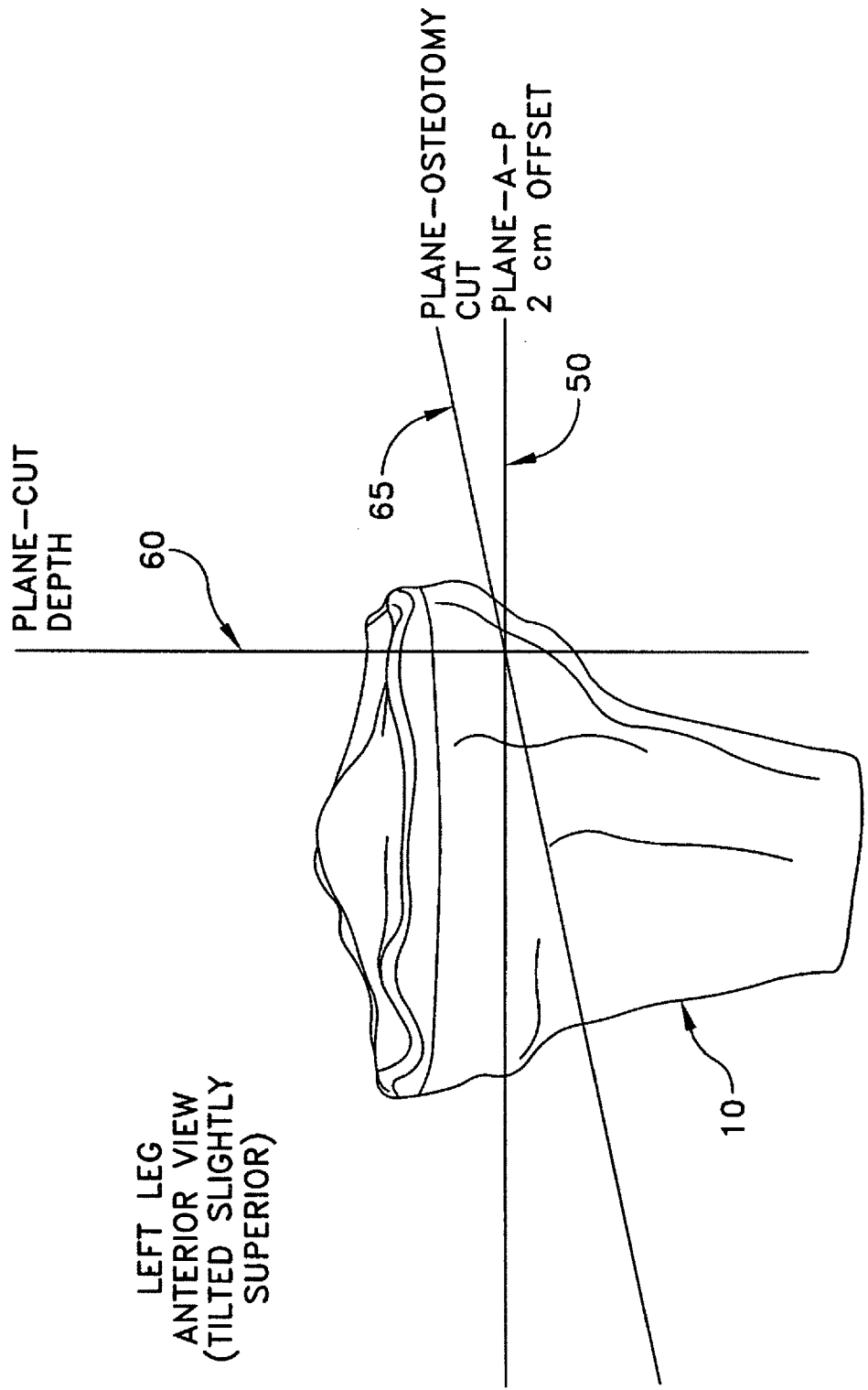

FIG. 9 is a direct view taken along the osteotomy cut plane. This view is tilted downward (e.g., at an angle of approximately 7°) from the direct frontal view of FIG. 8. Again, the angle of tilt downward is equal to the A-P slope. In other words, with the present invention, the osteotomy cut plane 65 extends parallel to the A-P slope plane 45 (in the anterior-to-posterior direction, although not in the medial-to-lateral direction), and typically slopes downward (e.g., at an angle of approximately 7-11°) when viewed in the anterior-to-posterior direction. Furthermore, with the present invention, the axis 70 (which defines the lateral limit to the osteotomy cut 20) is contained within the osteotomy cut plane 65.

Figure 16:
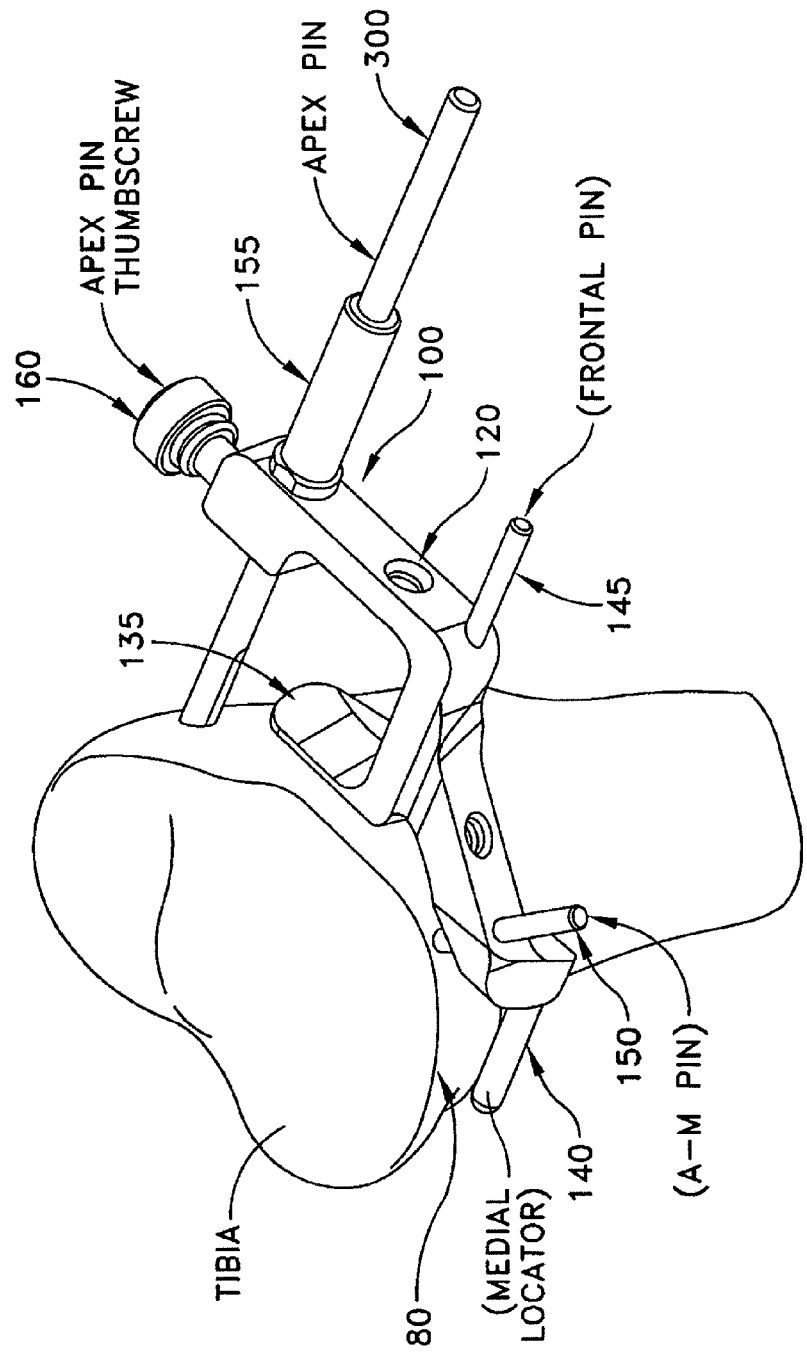

Novel Method and Apparatus for Performing the Open Wedge, High Tibial Osteotomy of the Present Invention In one preferred embodiment of the present invention, there is provided a novel osteotomy system which comprises instrumentation for use in making precise and repeatable osteotomy cuts for use in open wedge, high tibial osteotomies, preferably using an antero-medial approach. The novel osteotomy system generally comprises a positioning guide 100 (FIG. 16), a slope guide 200 (FIG. 11), an apex pin 300 (FIG. 16), a keyhole drill guide 400 (FIG. 18), a posterior protector 500 (FIG. 20), and a cutting guide 600 (FIG. 20), as will hereinafter be discussed in further detail.

The novel osteotomy system preferably also comprises a novel opening jack 700 (FIG. 22) for opening the cut 20 in the tibia so as to form the wedge-like opening 25 in the tibia, as will also hereinafter be discussed in further detail.

And the novel osteotomy system preferably also includes a novel implant 800 (FIG. 24) for positioning in the wedge-like opening in the tibia so as to stabilize the tibia in its corrected configuration, as will also hereinafter be discussed in further detail. Furthermore, in some instances, it may be advantageous to use an implant trial base 830 (FIGS. 27 and 28) in the course of preparing the tibia to receive implant 800, and in order to confirm proper fit of implant 800 in its seat, as will also hereinafter be discussed in further detail.

Thus, with the present invention, the surgeon first determines (using methods well known in the art) the degree of correction necessary to correctly re-align the weight-bearing axis of the knee; then the surgeon uses the system to make the appropriate cut 20 into the tibia; then the surgeon opens the bone cut to the extent required so as to form the desired wedge-like opening 25 in the tibia; and then the surgeon stabilizes the tibia in its corrected configuration (e.g., with the novel implant 800) while healing occurs.

In a preferred form of the invention, the novel osteotomy system is configured so that:

(i) the axis 70 (FIG. 8) formed at the lateral limit of the osteotomy cut 20 (which forms the lateral limit of the remaining bony hinge when the osteotomy cut 20 is thereafter opened) is parallel to the A-P tibial slope;

(ii) the axis of the lateral limit of the bony hinge created by the osteotomy cut lies in a plane that is perpendicular to the frontal (i.e., coronal) plane; and (iii) when the osteotomy cut 20 is completed and the wedge is opened, the distal (i.e., lower) tibia is rotated about the bony hinge so as to substantially maintain, in anatomical alignment, the A-P slope and the frontal plane.

In a preferred form of the invention, the novel osteotomy system is also configured so that:

(iv) the osteotomy can be performed less invasively; and (v) the osteotomy can be performed with minimum incising of soft tissue such as the medial collateral ligament, the lateral collateral ligament, and the hamstrings.

In a preferred form of the invention, the novel osteotomy system is also configured so that the delicate neurological and vascular tissues at the back of the knee are fully protected during the osteotomy procedure.

In one preferred form of the present invention, the novel osteotomy system is constructed and used as follows.

A vertical incision is first made on the antero-medial portion of the knee, approximately 1 cm from the medial edge of the patellar tendon, with the incision beginning approximately 2.5-3 cm superior to the anterior tibial tubercle, and extending approximately 6-10 cm in length.

The soft tissue between the patellar tendon and the proximal surface of the tibia is then dissected in order to make a small tunnel-like opening beneath the patellar tendon, just above the patellar tendon's insertion to the proximal tibia.

Figure 10:
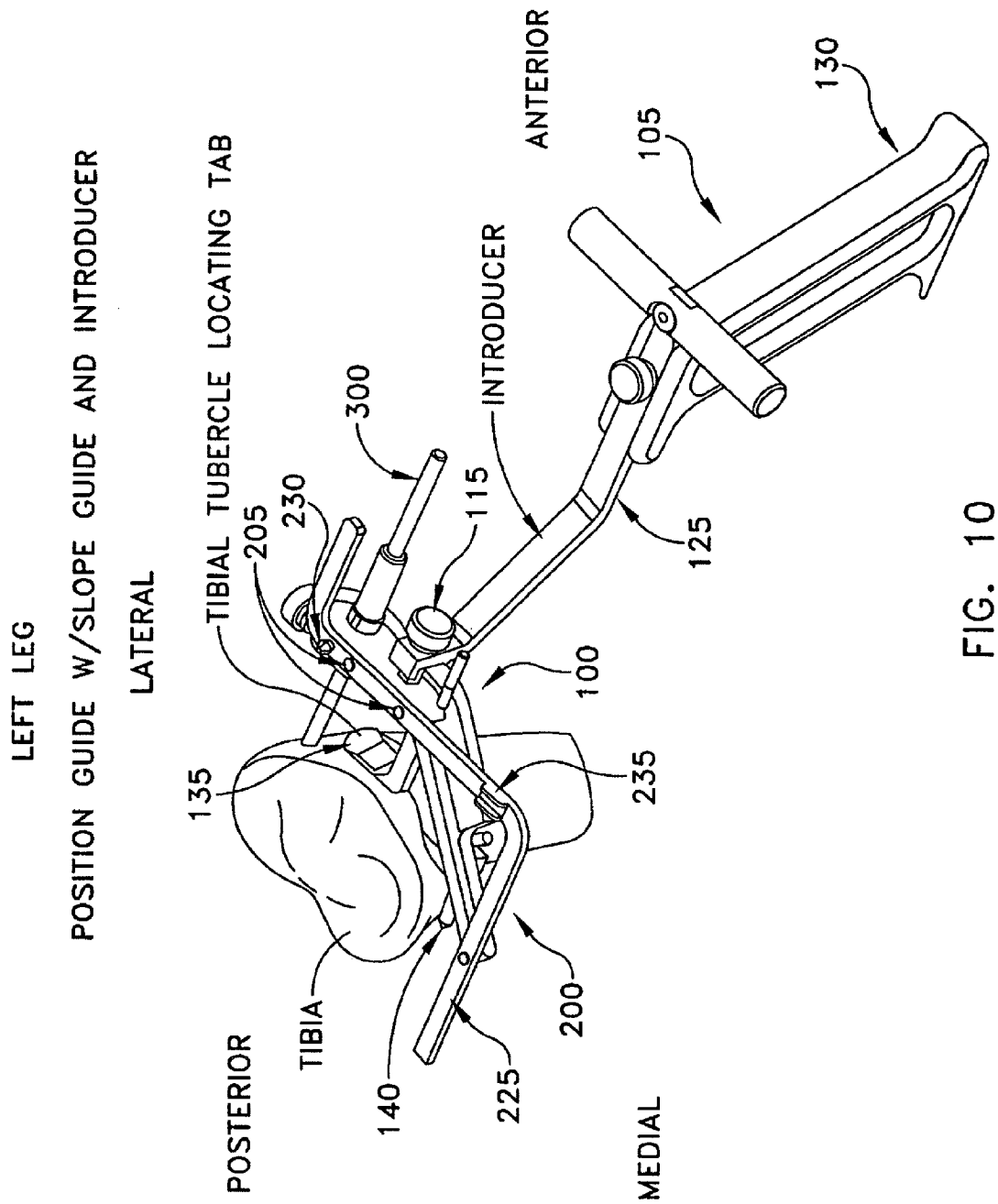
FIGS. 10-30 are schematic views showing a preferred method and apparatus for forming an appropriate osteotomy cut into the upper portion of the tibia, manipulating the tibia so as to open an appropriate wedge-like opening in the tibia, and then inserting an appropriate wedge-shaped implant into the wedge-like opening in the tibia.

Looking now at FIG. 10, an assembly comprising positioning guide 100 (FIGS. 10 and 16), slope guide 200 (FIGS. 10 and 11) and an introducer 105 (FIGS. 10 and 11) is advanced to the surgical site. Preferably the assembly of positioning guide 100, slope guide 200 and introducer 105 is pre-assembled prior to opening the skin. This assembly is assembled by first mounting slope guide 200 to positioning guide 100, and then mounting introducer 105 to both slope guide 200 and positioning guide 100 by using a screw 115 (FIG. 10) which passes through slope guide 200 and is received in a threaded bore 120 (FIG. 16) formed in positioning guide 100.

In one preferred form of the invention, slope guide 200 may comprise two separate elements which are secured together, e.g., a base 210 and a guide element 215 which are connected together by pins 205, with base 210 being formed out of a radio-translucent material (e.g., plastic) and guide element 215 being formed out of a radio-opaque material (e.g., stainless steel), whereby guide element 215 will be visible under fluoroscopy and base 210 will be effectively invisible under fluoroscopy, as will hereinafter be discussed.

In one preferred form of the invention, introducer 105 may comprise an arm 125 and a handle 130. Arm 125 and handle 130 may be formed as two separate elements secured together, or arm 125 and handle 130 may be formed as a singular construction.

Next, the foregoing assembly (of positioning guide 100, slope guide 200 and introducer 105) is maneuvered so that a tibial tubercle locating tab 135 (FIGS. 10 and 16) of positioning guide 100 is inserted between the patellar tendon (not shown) and the tibia, and so that tibial tubercle locating tab 135 is set against the superior margin of the tibial tubercle. In this way, the tibial tubercle provides a rough alignment guide for aligning positioning guide 100 with the tibia. If desired, the underside of tibial tubercle locating tab 135 may include serrations, ridges, ribs, etc. (FIG. 11E) so as to facilitate stabilization of tibial tubercle locating tab 135 (and hence the instrumentation) against the tibia.

Using a lateral fluoroscope view, taken from the medial side at the level of the tibial plateau, the assembly is then aligned so that the underside surface 220 (FIG. 11) of guide element 215 of slope guide 200 is aligned with the top of the medial condyle 75 of the tibia. Alternatively, if the surgeon prefers to shift the osteotomy slightly distally on the tibia, the top edge 225 of guide element 215 of slope guide 200 can be aligned with medial condyle 75, thereby offsetting the osteotomy by a fixed distance distally (e.g., 3 mm).

By forming the guide element 215 of slope guide 200 out of a radio-opaque material and by forming the base 210 of slope guide 200 out of a radio-translucent material, base 210 will be effectively invisible under fluoroscopy and guide element 215 will stand out in clear relief against the bone.

Figure 11:
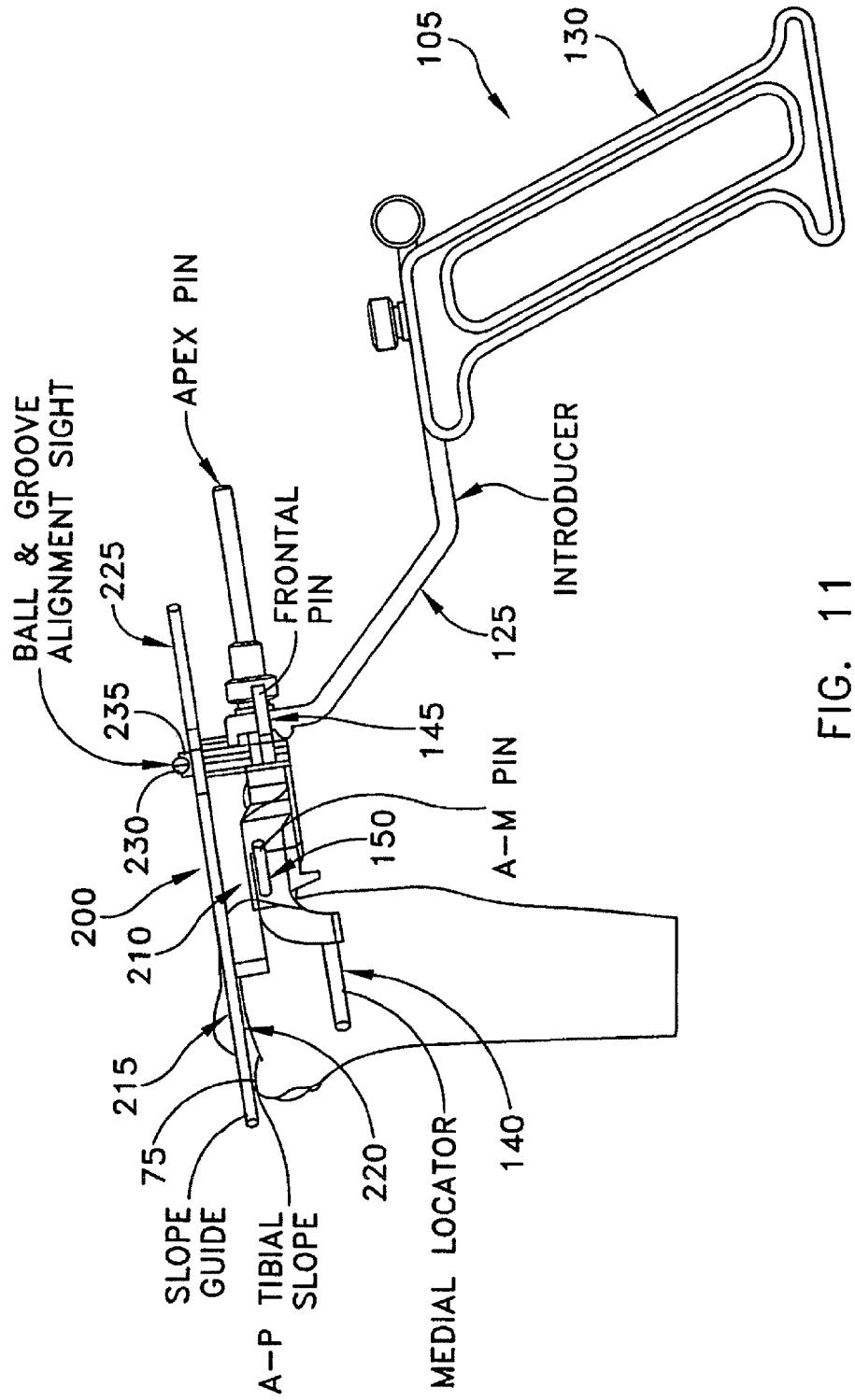
Figure 11A:
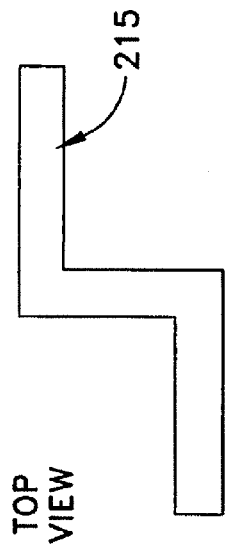
Figure 11B:
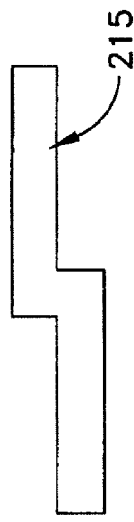
Figure 11C:
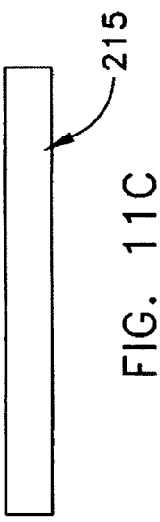

It should be noted that guide element 215 of slope guide 200 is preferably formed with a "Z shape" (FIGS. 10 and 11A) so as to provide additional functionality. More particularly, by forming guide element 215 with a "Z shape", several significant advantages are obtained. First, this construction permits guide element 215 to wrap around the perimeter of the tibia. Second, the "Z shape" of guide element 215 also operates to indicate if the slope guide is not vertically aligned with the level of the fluoroscope. More particularly, if slope guide 200 is not vertically aligned with the level of the fluoroscope, the "Z shape" of guide element 215 will appear as a jagged or zig-zag shape on the fluoroscope (FIG. 11B). However, if guide element 215 is vertically aligned with the level of the fluoroscope, then the guide element will appear as a straight line on the fluoroscope (FIGS. 11 and 11C). This vertical alignment is important, since it enables alignment of slope guide 200 (and hence positioning guide 100) with the medial condyle, i.e., with the A-P slope plane.

Figure 11D:
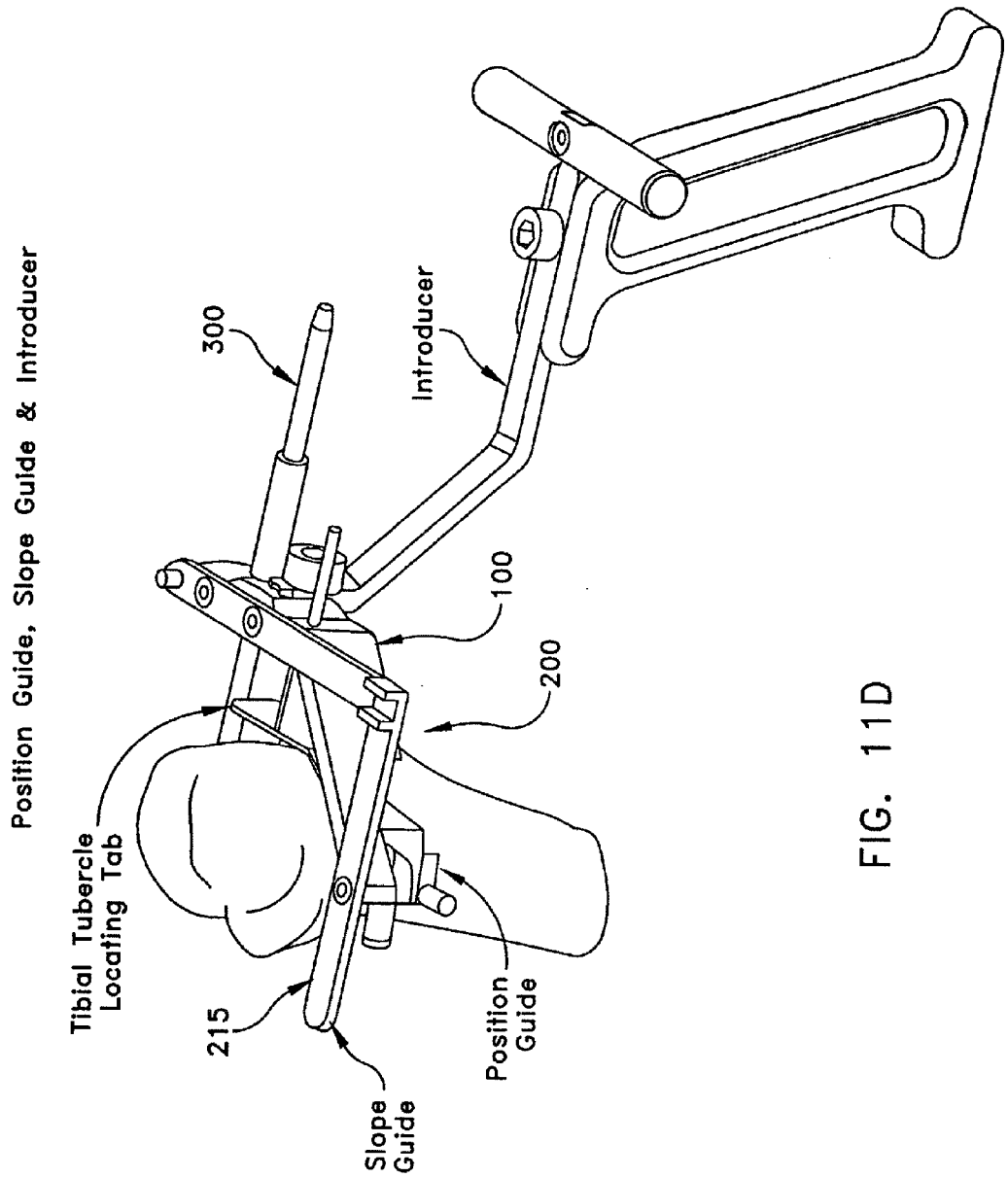
Figure 11E:
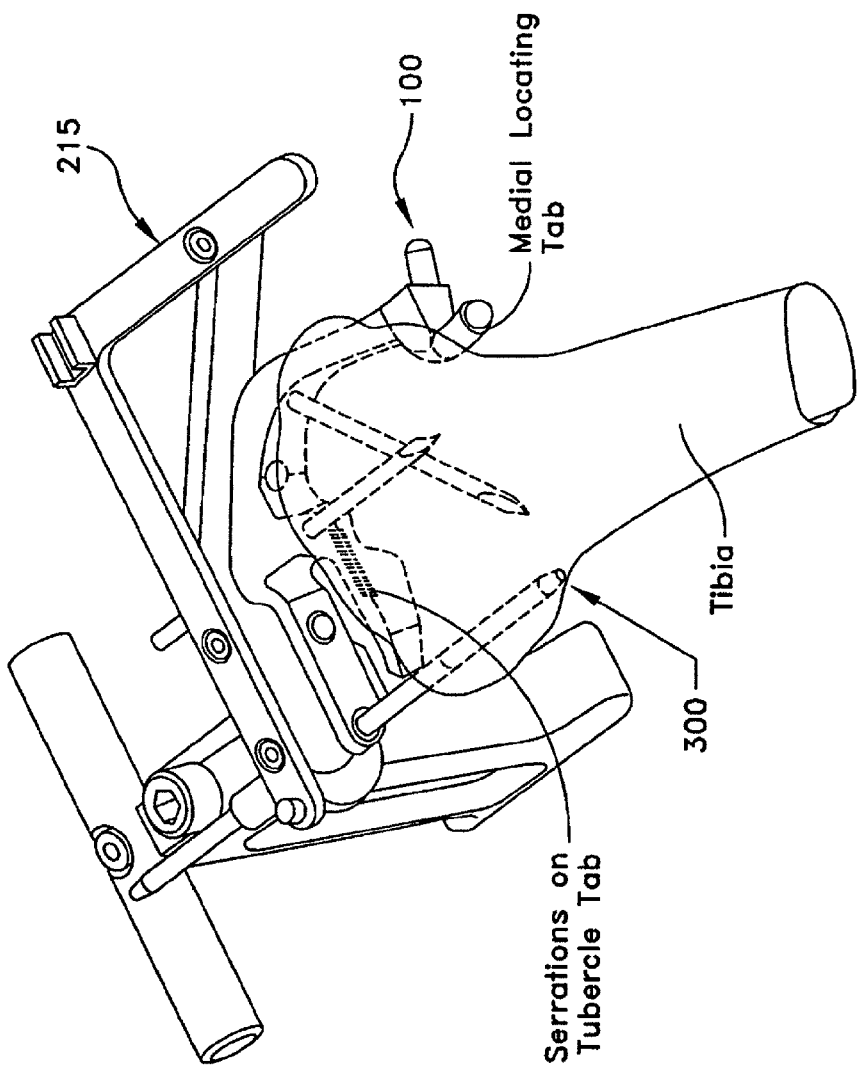
Figure 11F:
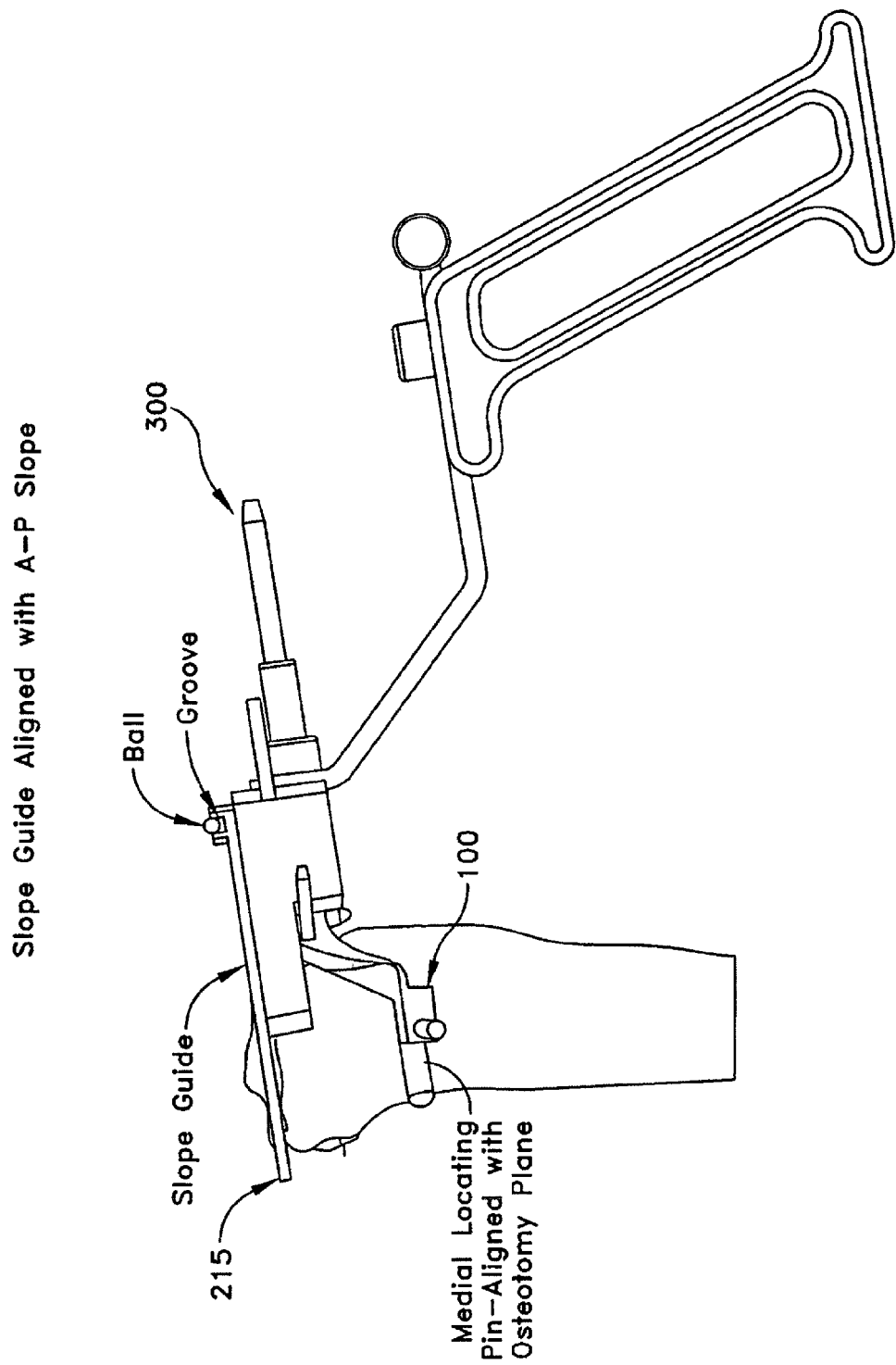

If desired, and looking now at FIGS. 11D, 11E and 11F, it is also possible to provide guide element 215 of slope guide 200 with an "L shape" configuration, rather than the "Z shape" configuration discussed above. Again, this construction provides several benefits. First, the "L shape" configuration permits guide element 215 to wrap around the perimeter of the tibia. Second, the "L shape" of guide element 215 also operates to indicate if the slope guide is not vertically aligned with the level of the fluoroscope. More particularly, if slope guide 200 is not vertically aligned with the level of the fluoroscope, the "L shape" of guide element 215 will appear as an "L shape" on the fluoroscope. However, if guide element 215 is vertically aligned with the level of the fluoroscope, then the guide element will appear as a straight line on the fluoroscope. Again, this vertical alignment is important, since it enables alignment of slope guide 200 (and hence positioning guide 100) with the medial condyle, i.e., with the A-P slope plane.

The assembly is then maneuvered so that the medial locating pin 140 (FIGS. 10, 11 and 16), preferably formed as a pin although it could also be formed as a tab, fin, etc., is located against the medial aspect 80 (FIG. 16) of the tibia. As further adjustments in position are made, medial locating pin 140 is held in contact with the medial aspect of the tibia, thereby ensuring proper alignment of the instrumentation. Medial locating pin 140 references the medial aspect of the tibia, thus setting the distance from the medial aspect of the tibia to the apex pin 300 (FIG. 10), and hence the distance from the medial aspect of the tibia to the axis 70 which demarcates the far limit of the osteotomy cut, as will hereinafter be discussed. Where a wedge-shaped osteotomy implant 27 is to be deployed in the wedge-like opening 25 (e.g., such as is shown in the system of FIGS. 10-30), this reference distance is used in conjunction with the sizing of the osteotomy implant 27 (FIG. 3) so as to ensure a proper tibial reconstruction, e.g., the distance from the medial aspect of the tibia to the center of apex pin 300 may correspond to the distance from the medial aspect of the wedge-shaped osteotomy implant 27 to the vertex of the wedge angle of the implant.

In another form of the invention, the reference distance may be the distance from the medial aspect of the tibia to a neutral axis of rotation in the bony hinge, which could be estimated by calculation. In this case, the distance from the medial aspect of the tibia to the neutral axis of the bony hinge may correspond to the distance from the medial aspect of the implant to the vertex of the wedge angle of the implant.

The assembly is then rotated around the primary tibial anatomical axis, by sliding introducer handle 130 in a side-to-side motion, such that the instrumentation is aligned perpendicular to the frontal (coronal) plane, i.e., so that introducer 105 and apex pin 300 (see below) extend parallel to the sagittal plane of the patient. To this end, slope guide 200 is provided with a ball 230 and a groove 235 (FIGS. 10 and 11). With the fluoroscope arranged so that it is set in the lateral mode, with the image being taken from the medial side at the level of the tibial plateau (see FIG. 11), the assembly is maneuvered until ball 230 is centered in groove 235 (FIG. 11). When this occurs, the system is aligned with the sagittal plane (i.e., positioning guide 100 is disposed so that apex pin 300 will extend perpendicular to the frontal plane, as will hereinafter be discussed).

Thus, when slope guide 200 is aligned with the medial condyle 75, and when ball 230 is aligned with groove 235, the system is aligned with (i) the A-P slope, and (ii) the sagittal plane. In other words, when slope guide 200 is aligned with medial condyle 75, and when ball 230 is aligned with groove 235, the instrumentation is positioned so that apex pin 300 (see below) is aligned with both the A-P slope and the sagittal plane, as will hereinafter be discussed.

With all of the previous adjustments established, the positions of (i) tibial tubercle locating tab 135, (ii) slope guide 200, (iii) medial locating pin 140, and (iv) ball and groove sights 230, 235, are verified. With all positions confirmed, the frontal pin 145 (FIG. 16) and the antero-medial (A-M) pin 150 (FIG. 16) are inserted through positioning guide 100 and into the tibia. This secures positioning guide 100 to the tibia with the desired alignment.

Next, apex pin 300 is inserted through positioning guide 100 and into the tibia. An apex aimer 155 (FIGS. 14 and 16) serves to guide apex pin 300 into the tibia with the proper orientation, i.e., so that apex pin 300 is positioned along the axis 70 (FIG. 8) which is located at the lateral limit of the intended osteotomy cut, with apex pin 300 extending parallel to the A-P slope and perpendicular to the coronal plane, and with apex pin 300 being coplanar with the intended cutting plane 65. As a result, apex pin 300 can serve as the lateral stop for the osteotomy saw, whereby to clearly define the perimeter of the bony hinge, as will hereinafter be discussed. Apex pin 300 may be tapped or drilled into virgin bone, or it may be received in a pre-drilled hole (e.g., formed using apex aimer 155 and a standard surgical drill). A thumbscrew 160 (FIG. 16) may be used to secure apex pin 300 to positioning guide 100.

Figure 11G:
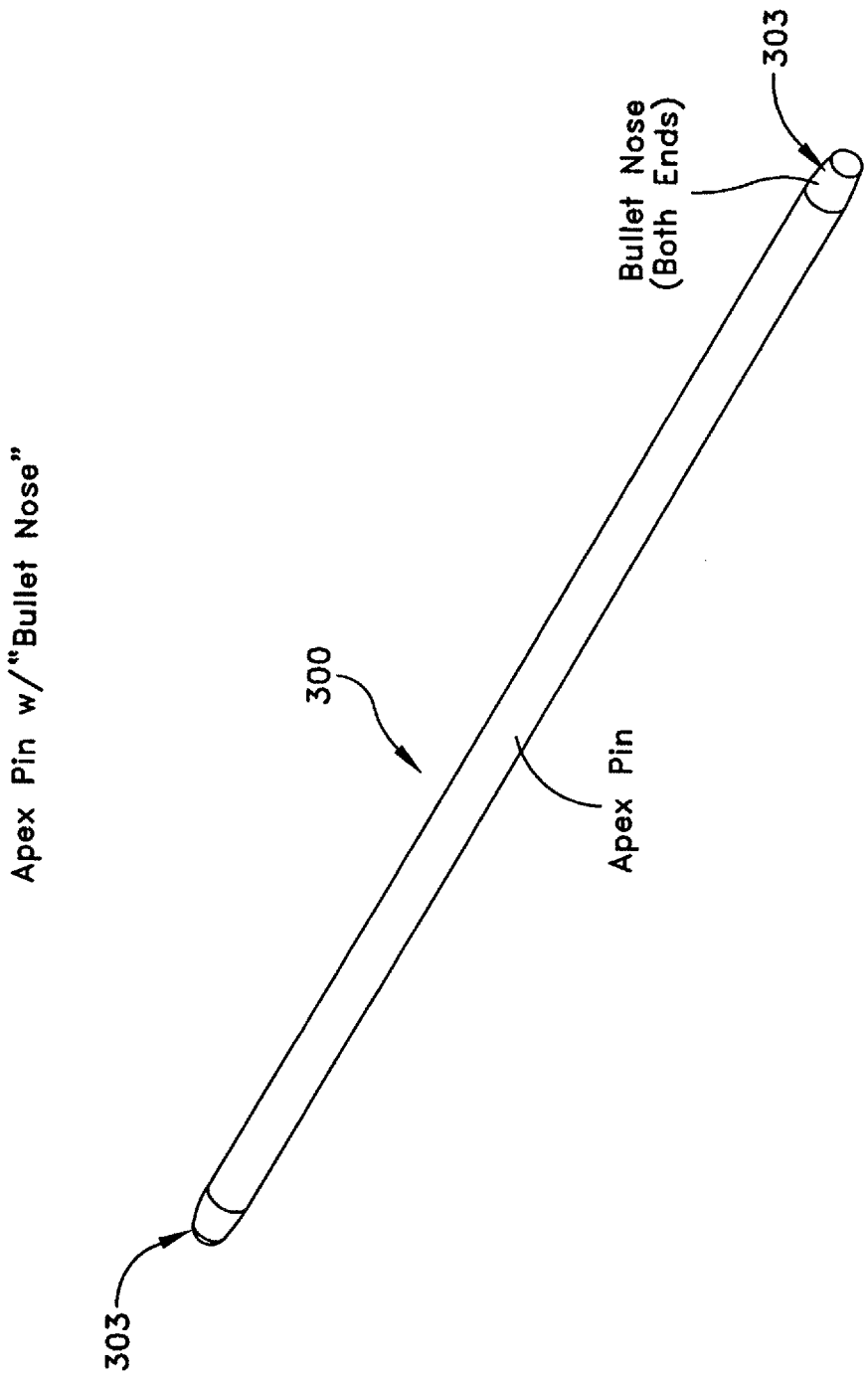
Figure 12:
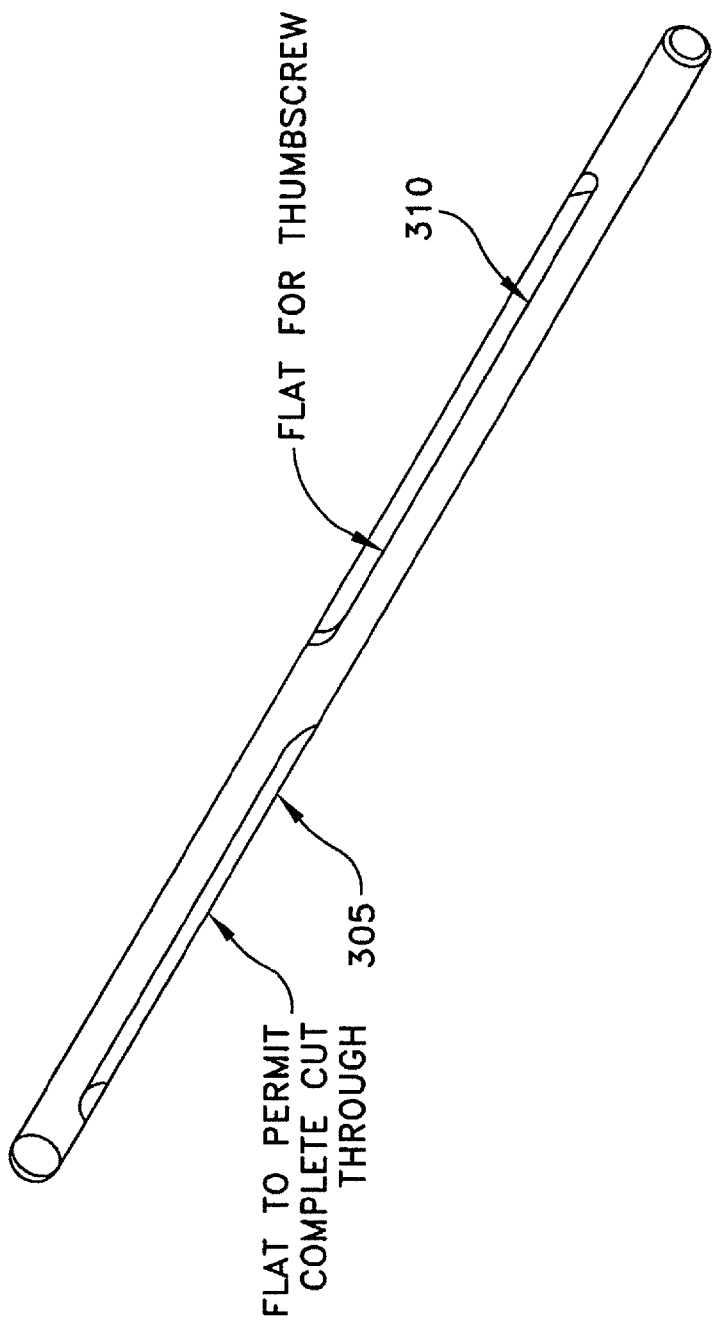
Figure 13:
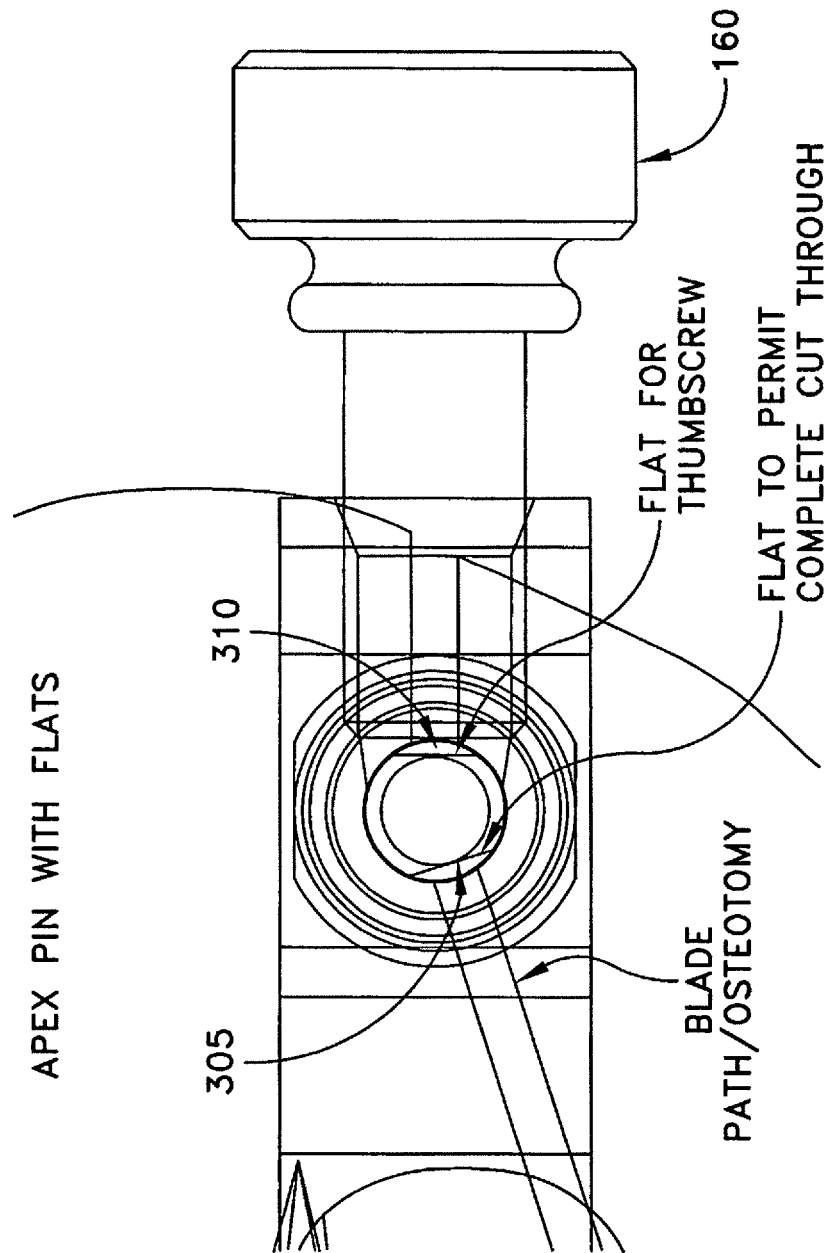
Figure 14:
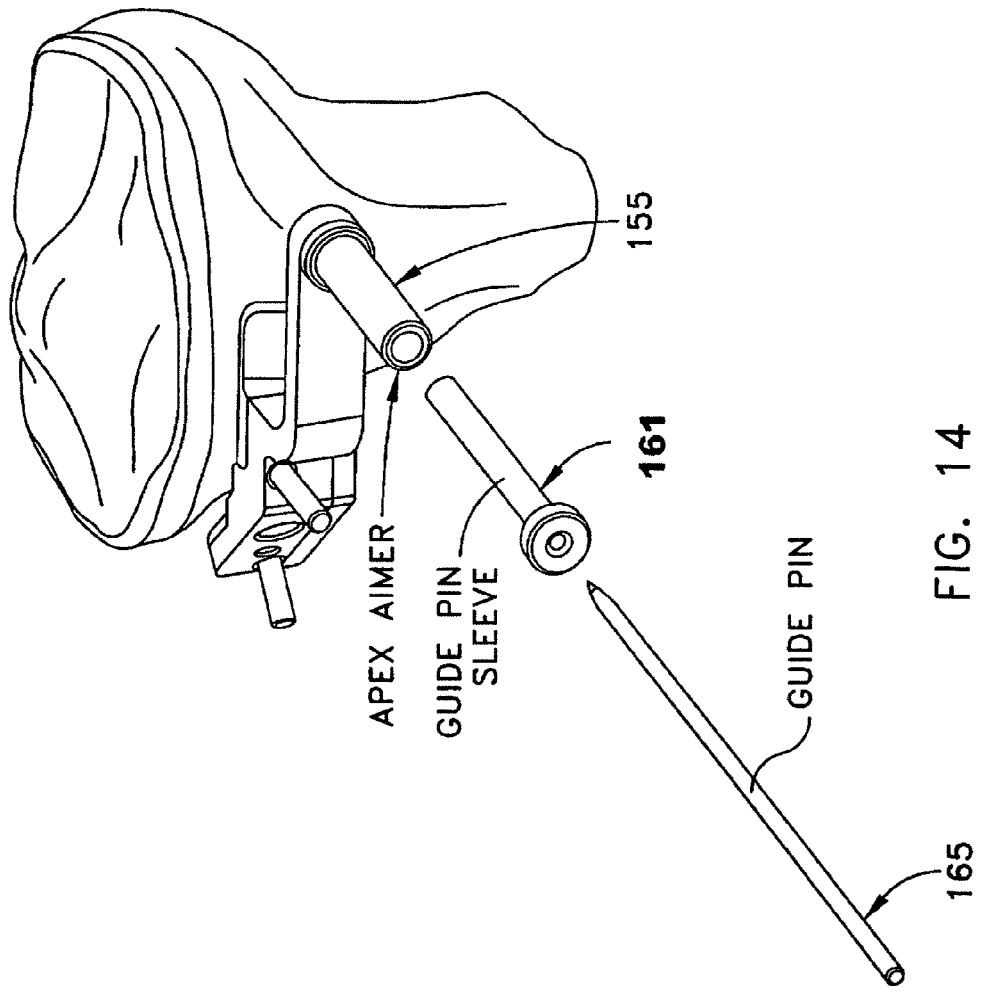

Apex pin 300 may be generally cylindrical in shape and, if desired, apex pin 300 may be provided with a rounded, or "bullet-shaped", nose 303 (FIG. 11G), or other tapered end configuration, so as to facilitate deployment into the tibia.

Furthermore, if desired, apex pin 300 may have a flat 305 (FIGS. 12 and 13) formed thereon to promote a complete cut-through of the osteotomy. Where apex pin 300 is provided with a distinct flat 305, it is preferably provided with a counterpart flat 310 (FIGS. 12 and 13), such that when apex pin 300 is positioned within the tibia and thumbscrew 160 is tightened against flat 310, the aforementioned flat 305 will be aligned with the osteotomy cut, whereby to ensure that the osteotomy blade cuts completely through the bone to reach the apex pin. See FIG. 13.

In another version of this construction (not shown), the flats 305, 310 may be diametrically opposed to one another, with thumbscrew 160 also being aligned with the osteotomy cut, whereby to make insertion of apex pin 300 less prone to error.

And in a preferred embodiment of the present invention, apex pin 300 may be necked down to a smaller diameter in the area of the osteotomy. As a result of this construction, a slight relief area exists to accommodate the saw blade so as to help promote a complete cut-through, but does not require any specific orientation of the apex pin with respect to the osteotomy plane, as is the case where the apex pin is formed with distinct flats.

And in another version of the present invention, apex aimer 155 may be used with a guide sleeve 161 (FIG. 14) and a small-diameter guide pin 165 in order to first check the position of the small-diameter guide pin 165 relative to the desired axis for the apex pin, before thereafter deploying the larger-diameter apex pin 300. In this respect, it will be appreciated that re-positioning a misdirected small-diameter guide pin 165 is easier and less traumatic to the host bone than re-positioning a misdirected larger-diameter apex pin 300.

Figure 15:
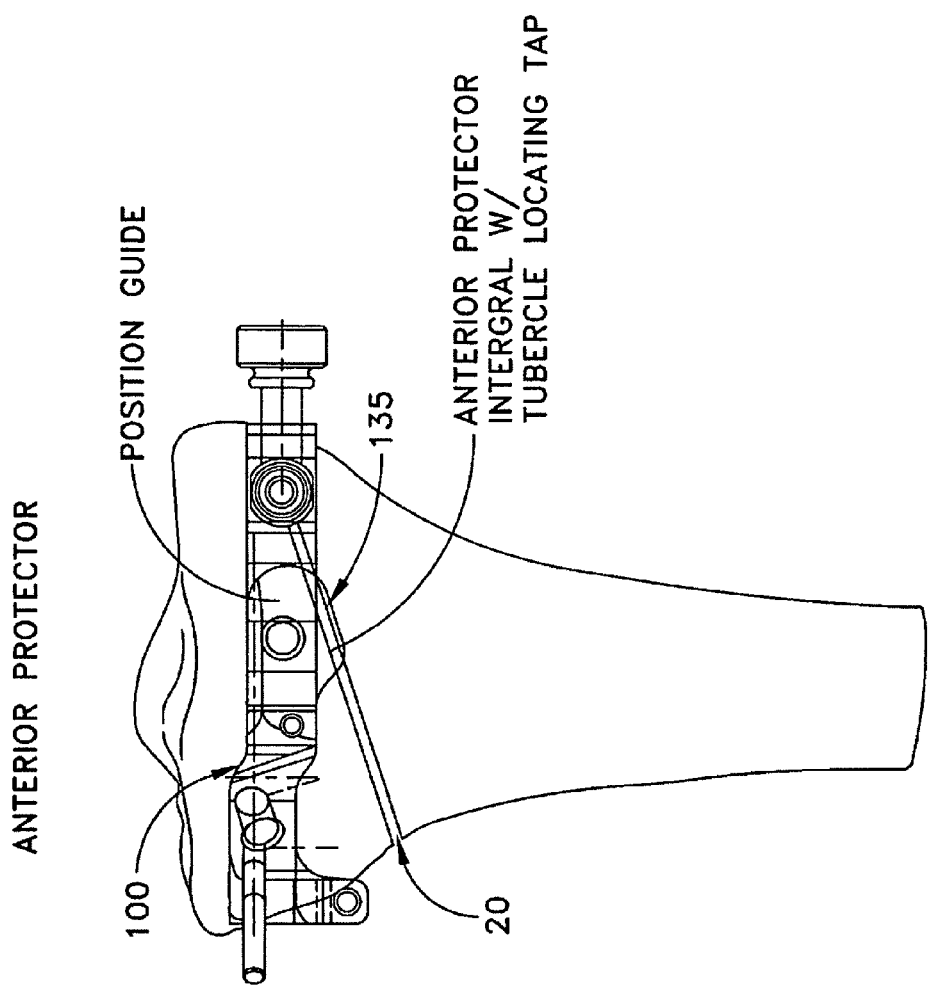

As seen in FIG. 15, tibial tubercle locating tab 135 is preferably sized so that it also functions as an anterior protector, by providing a protective shield between the oscillating saw blade (to be used later in the procedure to form the osteotomy cut 20) and the anterior soft tissue structures, e.g., the patellar tendon. In this respect it will be recalled that the tibial tubercle locating tab 135 is intended to be positioned between the face of tibia 10 and the backside of the patellar tendon. Thus, tibial tubercle locating tab 135 also functions as a patellar tendon protector.

By virtue of the foregoing, it will be seen that apex pin 300 is positioned in the patient's tibia so that the apex pin extends (i) parallel to the A-P slope of the tibia, and (ii) parallel to the sagittal plane of the patient. As a result, when the osteotomy cut 20 is subsequently formed in the bone (see below) by cutting along the osteotomy cut plane 65 (FIG. 8) until the apex pin is engaged by the bone saw, so that the perimeter of the bony hinge is defined by the location of the apex pin, the bony hinge will extend (i) parallel to the A-P slope of the tibia, and (ii) parallel to the sagittal plane of the patient. By ensuring that apex pin 300 is set in the aforementioned fashion, and hence ensuring that the bony hinge is so created, the final configuration of the tibia can be properly regulated when the bone cut is thereafter opened so as to form the open wedge osteotomy.

Once apex pin 300 has been properly positioned in the bone, slope guide 200 and introducer 105 are removed (FIG. 16), leaving positioning guide 100 properly aligned on, and secured to, the tibia, with apex pin 300 extending parallel to the A-P slope and parallel to the sagittal plane of the patient.

Figure 17:
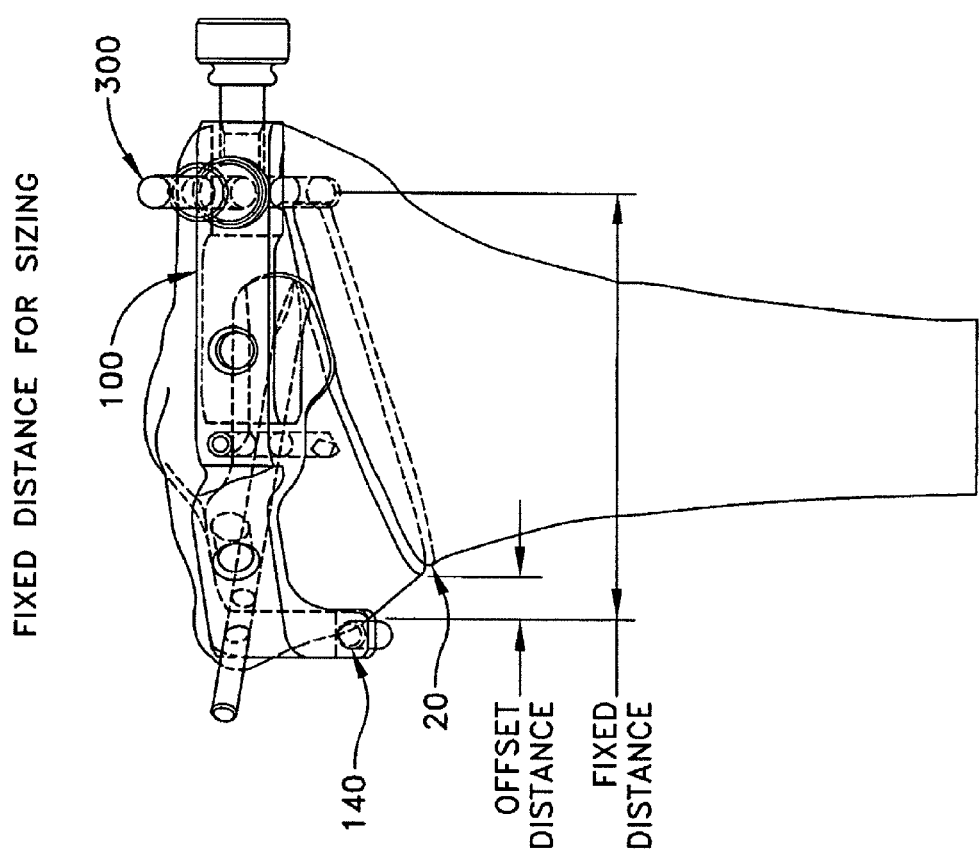

As will be discussed in further detail below, the system of FIGS. 10-30 utilizes a wedge-shaped implant to maintain the open wedge osteotomy. In this respect, the size of positioning guide 100 and the associated instrumentation are preferably used to prepare the osteotomy to fit a particular implant sizing of small, medium or large. More particularly, the medial locating pin 140, the size of positioning guide 100, and apex pin 300 all preferably combine to implement an implant sizing scheme of small, medium or large. As seen in FIG. 17, medial locating pin 140, positioning guide 100 and apex pin 300 combine to provide a known, fixed distance from the medial aspect of the tibia to the apex pin. The size of the planned osteotomy is then set, allowing a specifically-sized implant (e.g., small, medium or large) to nominally fit between the medial aspect of the tibia and the apex pin.

In the embodiment shown in FIG. 17, there is a known lateral offset between medial locating pin 140 and the entry point of the osteotomy. The implant size is reduced slightly to factor in this offset distance so as to yield a proper fit.

Figure 17A:
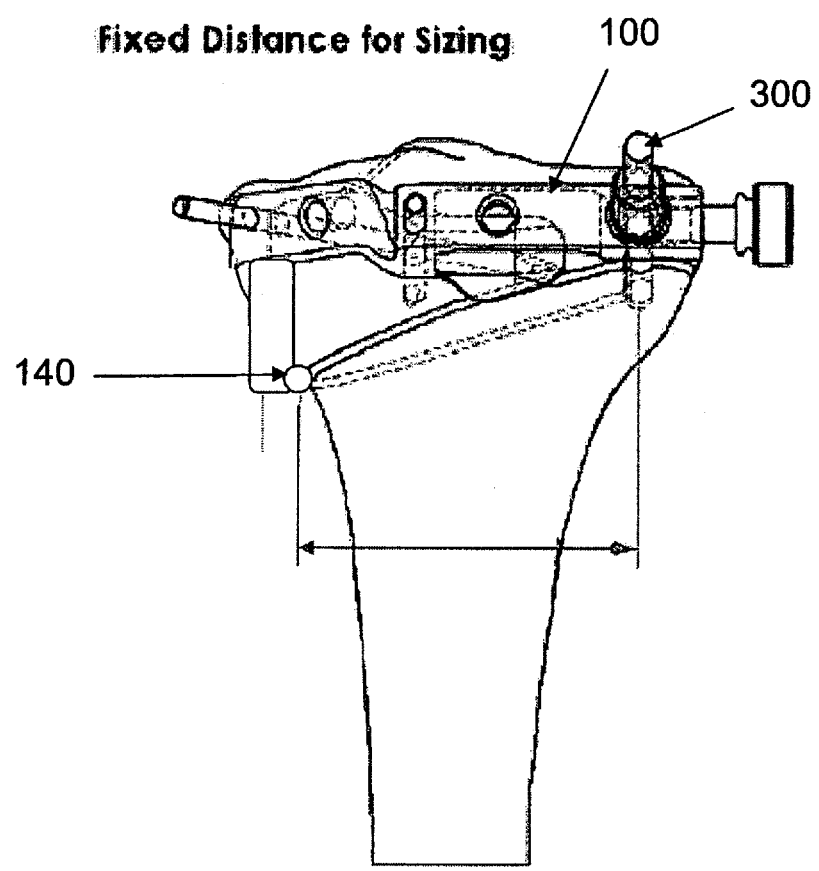

In a more preferred construction, and looking now at FIG. 17A, medial locating pin 140 is substantially aligned with the entry point of the planned osteotomy.

Figure 18:
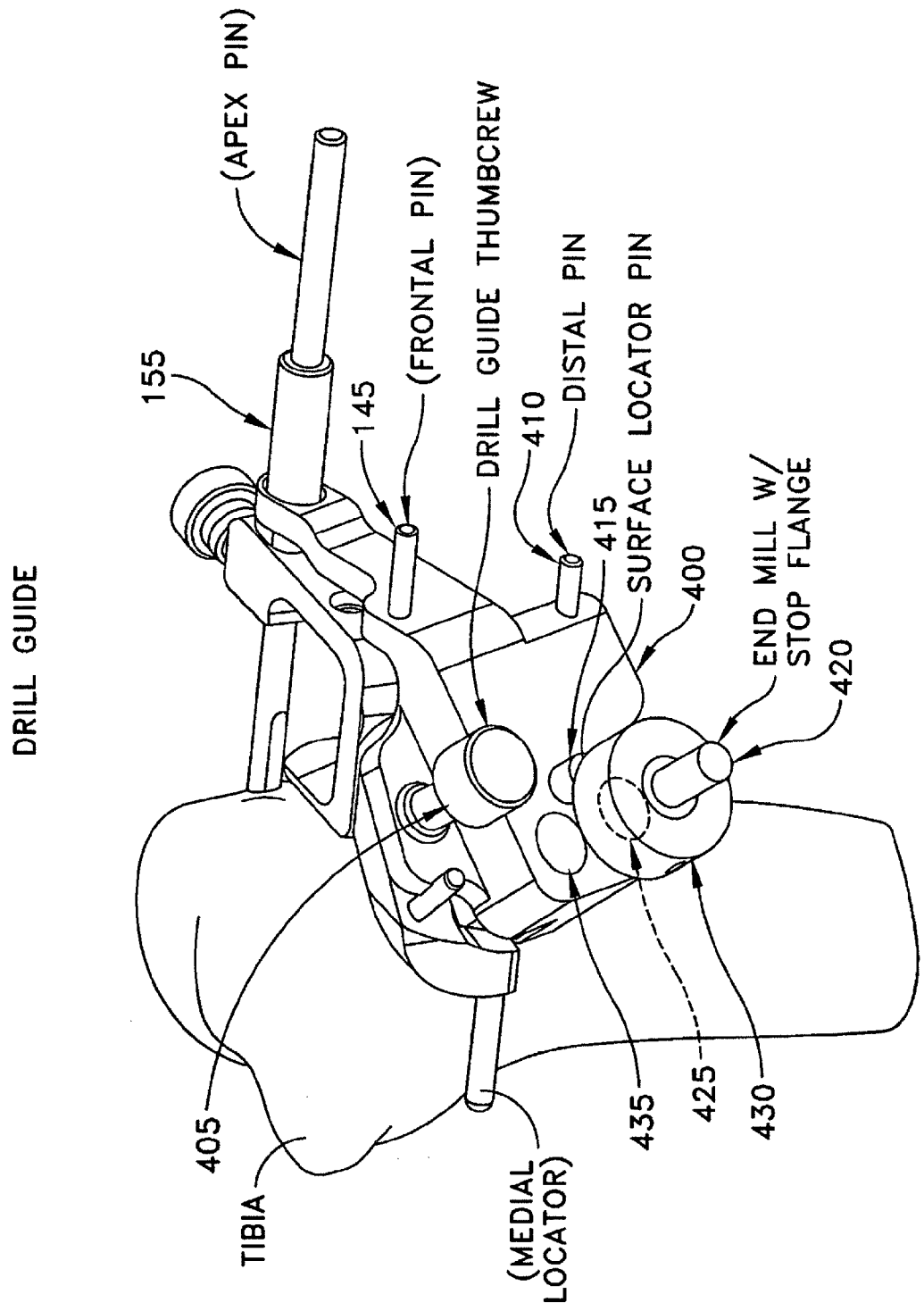

Looking next at FIG. 18, keyhole drill guide 400 is then attached to positioning guide 100 by passing keyhole drill guide 400 over frontal pin 145 and apex aimer 155. Keyhole drill guide 400 is then secured in this position with thumbscrew 405. At this point, a distal pin 410 is inserted through keyhole drill guide 400 and into the tibia. Distal pin 410 further secures the instrumentation to the tibia. Next, a surface locator pin 415 is inserted through keyhole drill guide 400. Surface locator pin 415 slides through keyhole drill guide 400 until the distal tip of surface locator pin 415 contacts the surface of the tibia. For the purposes of the present invention, this surface may be referred to as the "antero-medial surface" or the "A-M surface", which is the anatomical surface of the tibia corresponding to the antero-medial approach of the osteotomy. When surface locator pin 415 contacts the A-M surface, the surface locator pin can act as an indicator as to the location of the A-M surface. This information can then be used to set the depth of the keyholes which are to be formed in the tibia (see below) for an improved implant fit.

Figure 29:
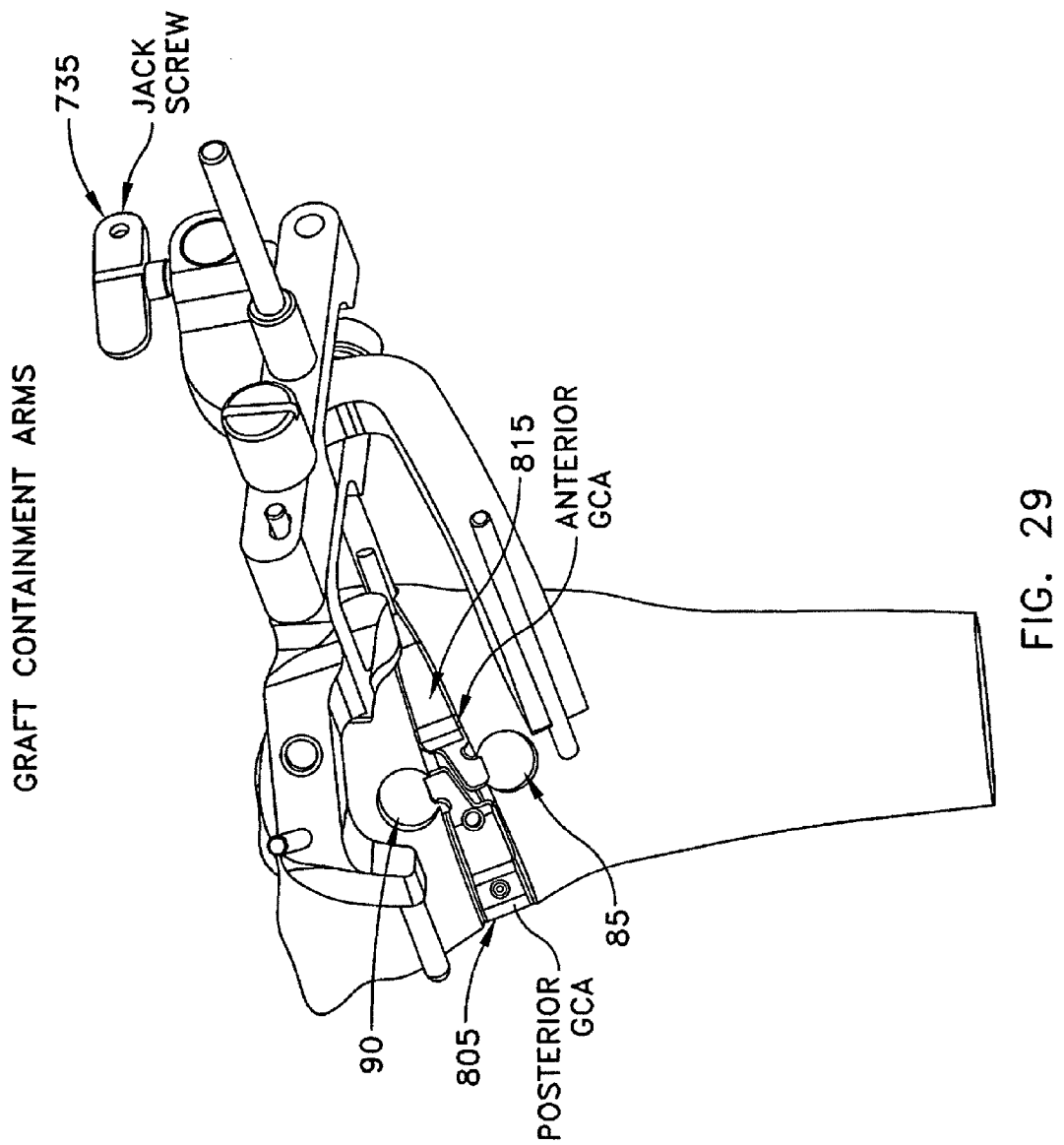
Figure 30:
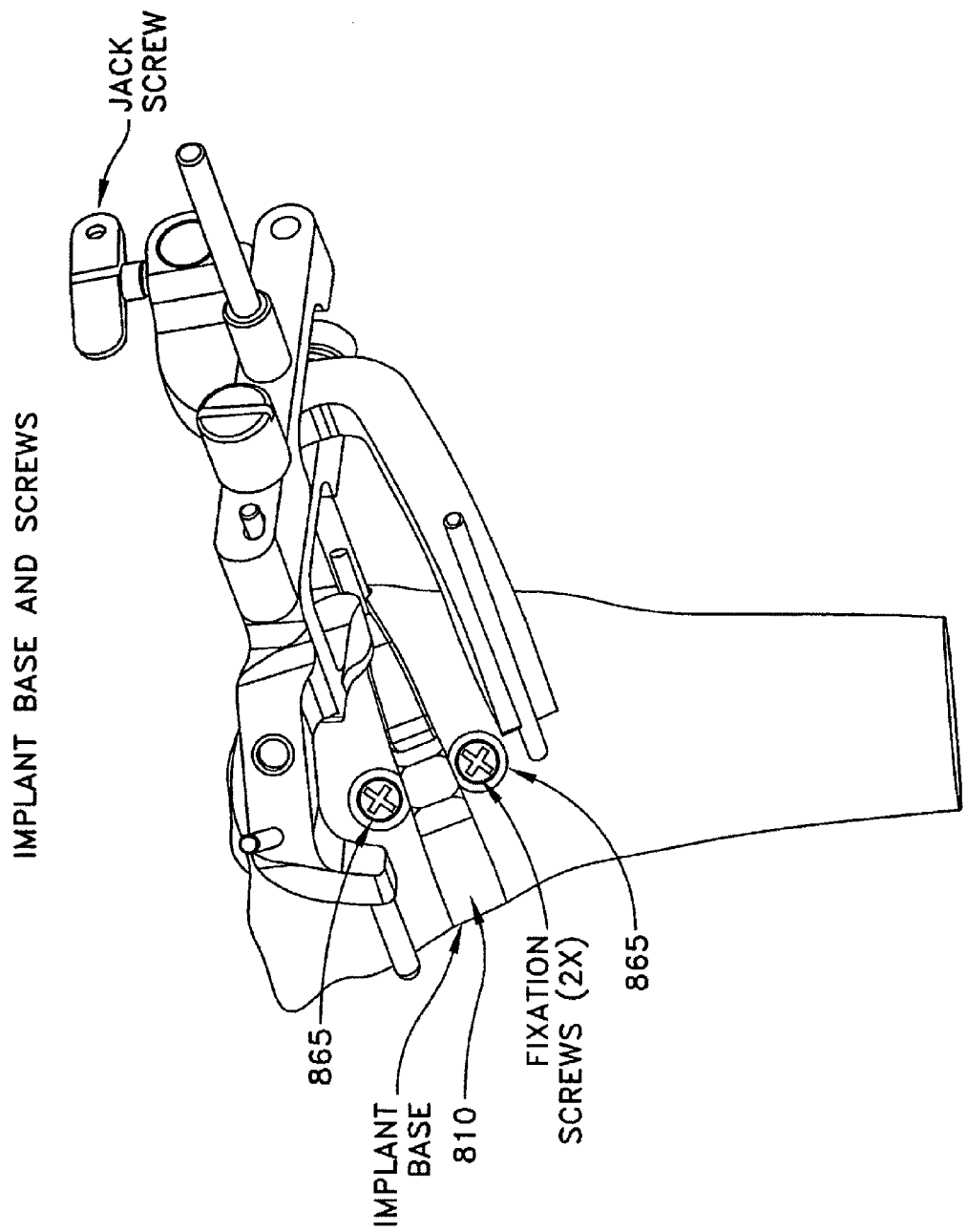

Next, an end mill 420 is inserted into the distal hole 425 (i.e., the bottom hole 425) of keyhole drill guide 400 and drilled until a stop flange 430 on end mill 420 contacts the proximal end of surface locator pin 415, whereby to form the distal keyhole 85 (FIG. 21) in the tibia. The drilling procedure is then repeated for the proximal hole 435 (i.e., the top hole 435), whereby to form the proximal keyhole 90 (FIG. 21) in the tibia. Thus, keyholes 85 and 90 are formed so that one keyhole (i.e., proximal keyhole 90) sits above the other keyhole (i.e., distal keyhole 85), in a so-called "over-under" configuration. While it is possible to drill the proximal keyhole before the distal keyhole, it is generally preferable to drill the distal keyhole first. This is because drilling the distal keyhole before the proximal keyhole reduces the possibility that the sloping nature of the bone will cause a later-drilled keyhole to slip into an earlier-drilled keyhole. It should be appreciated that keyhole drill guide 400 is configured so that distal hole 425 and proximal hole 435 will overlap the osteotomy cutting plane 65 to some extent (FIG. 21), so that when osteotomy cut 20 is thereafter formed and the tibia subsequently opened so as to create the wedge-like opening 25, distal keyhole 85 and proximal keyhole 90 will overlap, and communicate with, the wedge-like opening 25 (FIG. 29).

Once the two implant keyholes have been drilled into the tibia, end mill 420 is removed, thumbscrew 405 is loosened, and then keyhole drill guide 400 is removed.

Figure 19:
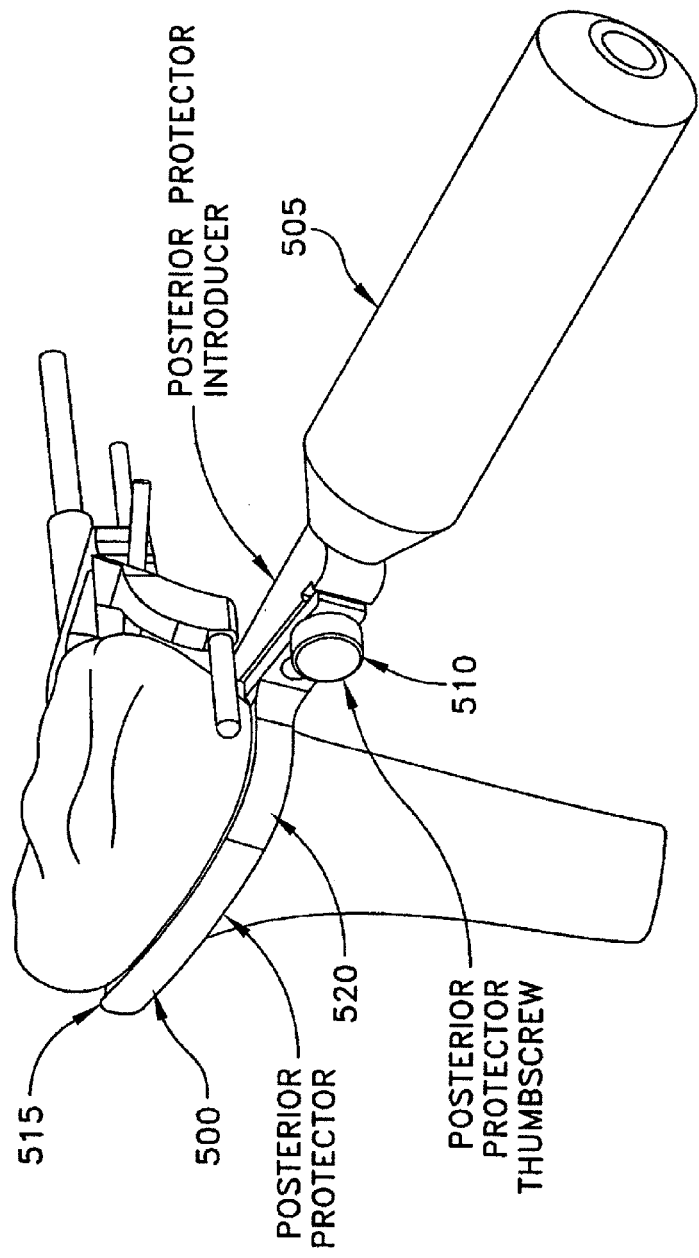
Figure 21:
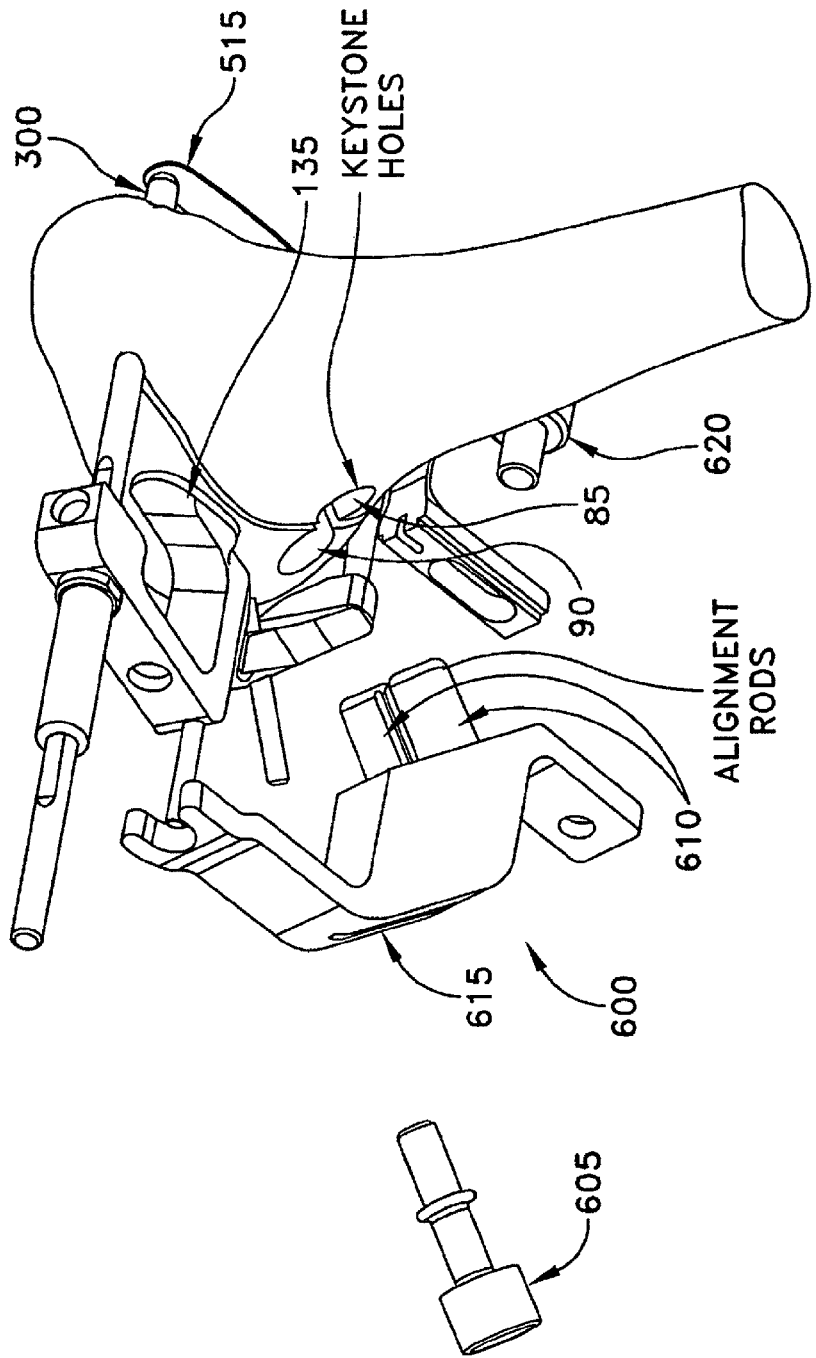

Next, and looking now at FIG. 19, posterior protector 500 is attached to an introducer 505 with a thumbscrew 510. Posterior protector 500 preferably comprises a far tip 515 and a curved portion 520. Far tip 515 is preferably formed out of a flexible material so as to facilitate passage of the posterior protector along the surface of the posterior cortex and beneath overlying soft tissue. Curved portion 520 comprises a relatively stiff material which provides support for far tip 515. Far tip 515 of posterior protector 500 is inserted into the incision and worked along the posterior cortex of the tibia until far tip 515 of posterior protector 500 substantially crosses the axis of, and in some cases actually engages, apex pin 300 (FIG. 21). Once posterior protector 500 has been properly positioned, the thumbscrew 510 is unscrewed, and introducer handle 505 is removed, leaving posterior protector 500 extending along the posterior cortex of the tibia, interposed between the tibia and the delicate neurological and vascular structures located at the back of the knee.

Figure 20:
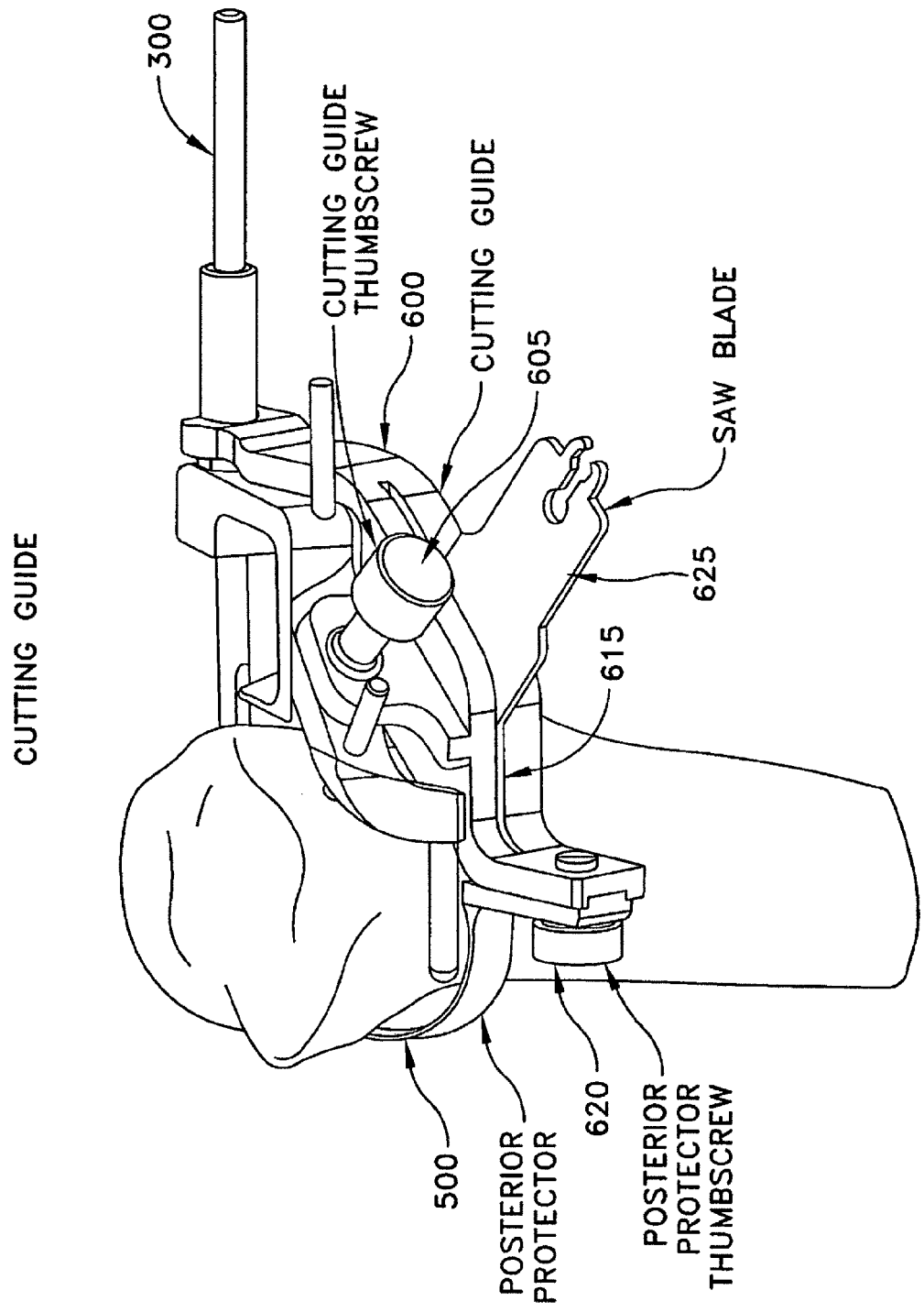

Looking next at FIG. 20, cutting guide 600 is then attached to positioning guide 100 and secured in place using cutting guide thumbscrew 605. Cutting guide 600 comprises alignment rods 610 (FIG. 21) that extend from the cutting guide into the pre-drilled keyholes 85, 90 (FIG. 21) to assist with cutting alignment. More particularly, alignment rods 610 ensure proper alignment between cutting guide 600, its cutting slot 615 (FIGS. 20 and 21) and the pre-drilled keyholes 85, 90 previously formed in the tibia with end mill 420 and, ultimately, ensure the desired fit between the implant and the tibia.

Then, posterior protector 500 is attached to cutting guide 600 using thumbscrew 620 (FIG. 20).

At this point, the instrumentation is ready to form the osteotomy cut, with cutting slot 615 of cutting guide 600 properly aligned with the osteotomy cut plane, apex pin 300 properly positioned at the far (lateral) limit of the osteotomy cut, tibial tubercle locating tab 135 forming a protective shield for the patellar tendon, and with posterior protector 500 forming a protective shield for the vascular and neurological structures at the back of the knee. In this respect it should be appreciated that cutting guide 600 is sized and shaped, and cutting slot 615 is positioned, so that, in addition to being aligned with the apex pin 300, the entry point of the cutting plane into the tibia is located at an appropriate location on the tibia's medial neck 66.

Next, a saw blade 625 (attached to an oscillating saw, not shown) is inserted into cutting slot 615 of cutting guide 600. The osteotomy cut is then made by plunging the oscillating saw blade through cutting slot 615 and into the bone (FIG. 20). The saw blade is used to cut completely through the medial and posterior cortices. The saw is operated until saw blade 625 contacts posterior protector 500 and apex pin 300. As the saw blade cuts through the tibia, it is constrained by cutting slot 615, apex pin 300 and posterior protector 500, so that the saw blade may only cut bone along the osteotomy plane, up to (but not beyond) the desired location of the bony hinge, and does not cut soft tissue. During cutting, tibial tubercle locating tab 135 also ensures that the saw blade will not inadvertently cut the patellar tendon. Thus, cutting slot 615, apex pin 300, posterior protector 500 and tibial tubercle locating tab 135 effectively define a "safe cutting zone" for saw blade 625.

After saw blade 625 forms the desired osteotomy cut 20 along the cutting plane, the saw blade is removed, and a hand osteotome (not shown) of the sort well know in the art is inserted through cutting slot 615 and into the osteotomy cut 20, and then the cut is completed through the posterior cortical bone near apex pin 300 and posterior protector 500. Then the hand osteotome is removed.

At this point the osteotomy cut 20 has been completed, with the osteotomy cut terminating on the lateral side at apex pin 300, so that the bony hinge is properly positioned at the desired location, i.e., parallel to the A-P slope and perpendicular to the coronal plane.

Next, thumbscrew 620 is loosened and posterior protector 500 removed. Then thumbscrew 605 is loosened and cutting guide 600 is removed. See FIG. 21.

At this point, the desired osteotomy cut 20 has been formed in the tibia, with keyholes 85 and 90 formed below and above, respectively, the osteotomy cut.

In order to complete the procedure, the bone must now be opened so as to reconfigure the tibia to the desired geometry, and then the tibia stabilized with the desired configuration, e.g., by inserting a wedge-shaped implant 27 into wedge-like opening 25.

Figure 22:
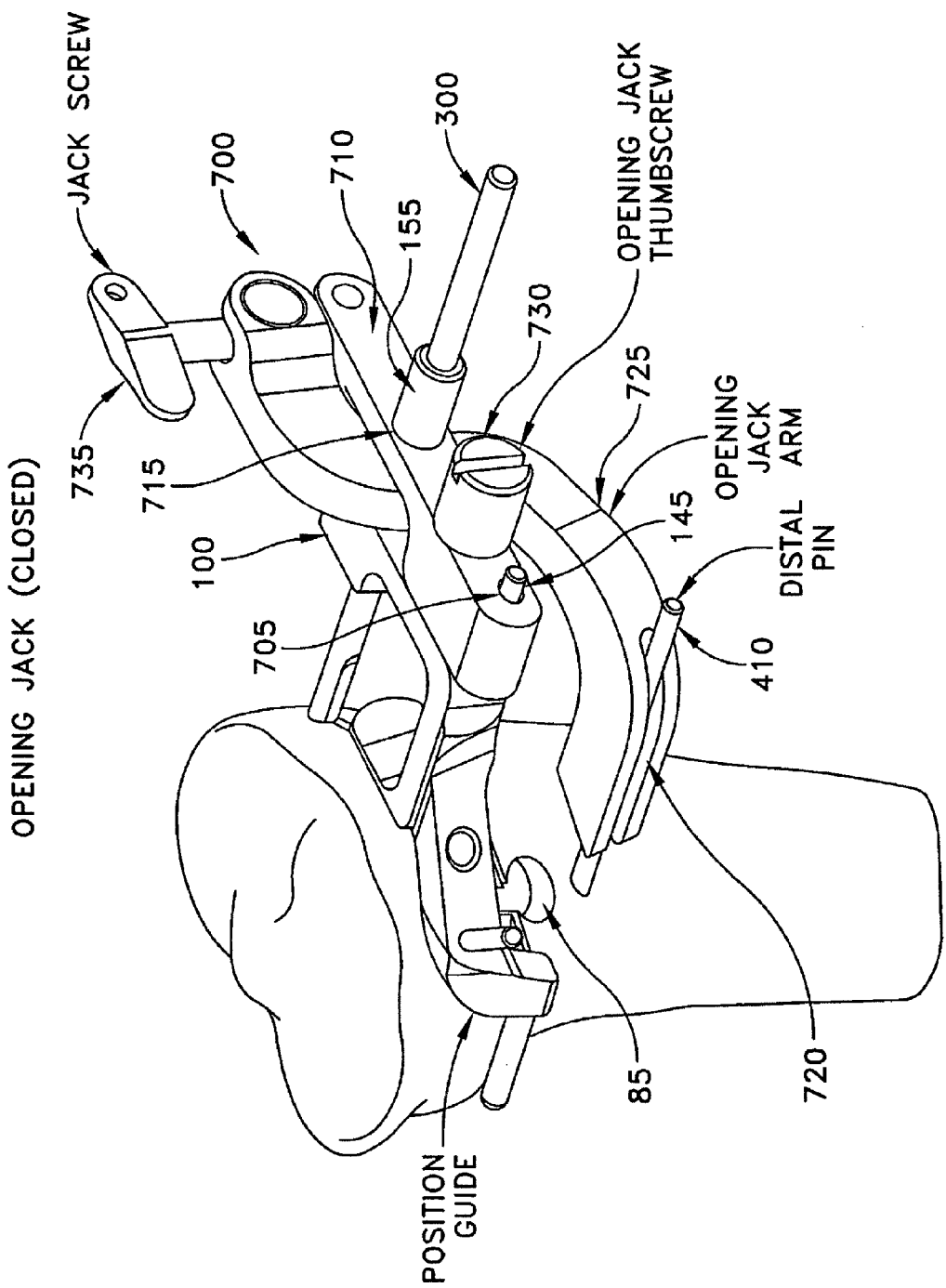

Looking next at FIG. 22, opening jack 700 is assembled onto the instrumentation by receiving frontal pin 145 in a hole 705 formed in jack arm 710, by receiving apex aimer 155 in another hole 715 formed in jack arm 710 and jack arm 725, and by receiving distal pin 410 in a slot 720 formed in jack arm 725. Opening jack 700 is secured to positioning guide 100 with a thumbscrew 730.

Figure 23:
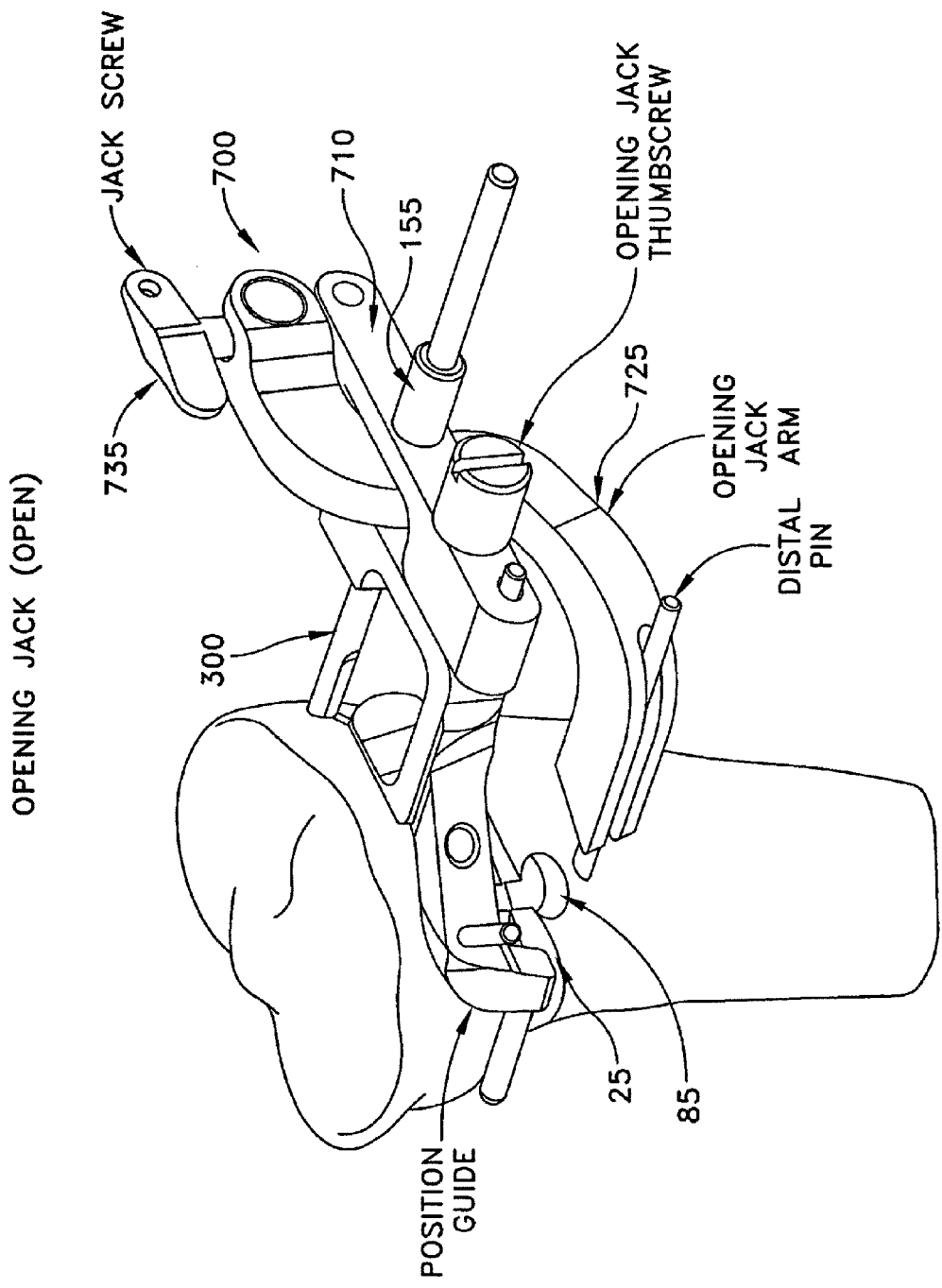
Figure 23A:
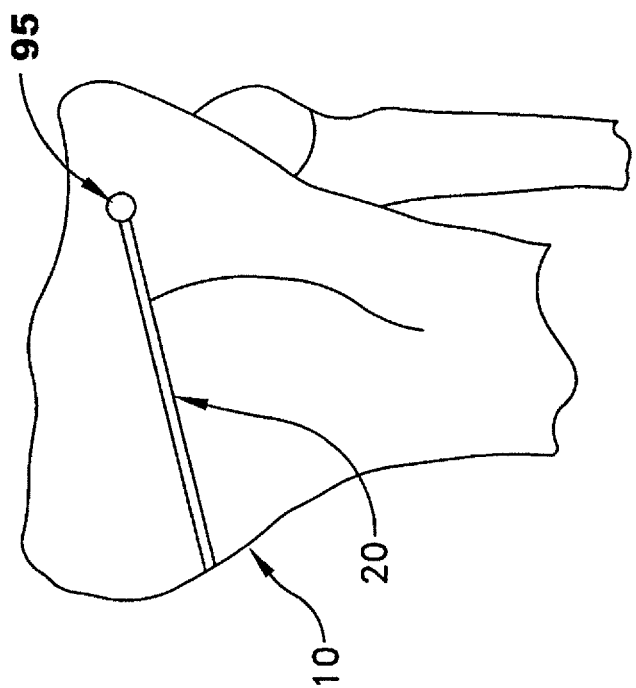

Once opening jack 700 is in place, the jack is opened by rotating jack screw 735. This causes jack arm 725 to pivot about apex aimer 155 so as to open the jack and thereby open the desired wedge-like opening 25 in the tibia. See FIG. 23. Preferably the patient's lower leg is manipulated as jack screw 735 is turned so as to assist in opening of the bone about the bony hinge. As the wedge-like opening 25 is created in the bone, the tibia will be reoriented in a highly controlled manner, due to the fact that the bony hinge is precisely positioned at axis 70 through the use of apex pin 300, i.e., the bony hinge extends parallel to the A-P slope and parallel to the sagittal plane. Furthermore, as the wedge-like opening 25 is created in the bone, the risk of bone cracking is minimized, due to the fact that apex pin 300 forms an oversized hole 95 (FIGS. 23A and 27) at the lateral end of the bone cut, i.e., "oversized" relative to the thickness of the osteotomy cut, whereby to reduce the occurrence of stress risers and the like as the bone is opened.

The surgeon uses opening jack 700 to open the bone to the extent necessary to correctly re-align the weight-bearing axis of the knee.

Then, with opening jack 700 still in place, an implant is positioned at the wedge-like opening 25 so as to hold the re-oriented bone with the desired orientation.

If desired, the implant may be a "generic" wedge-shaped implant such as the implant 27 shown in FIG. 3.

Figure 24:
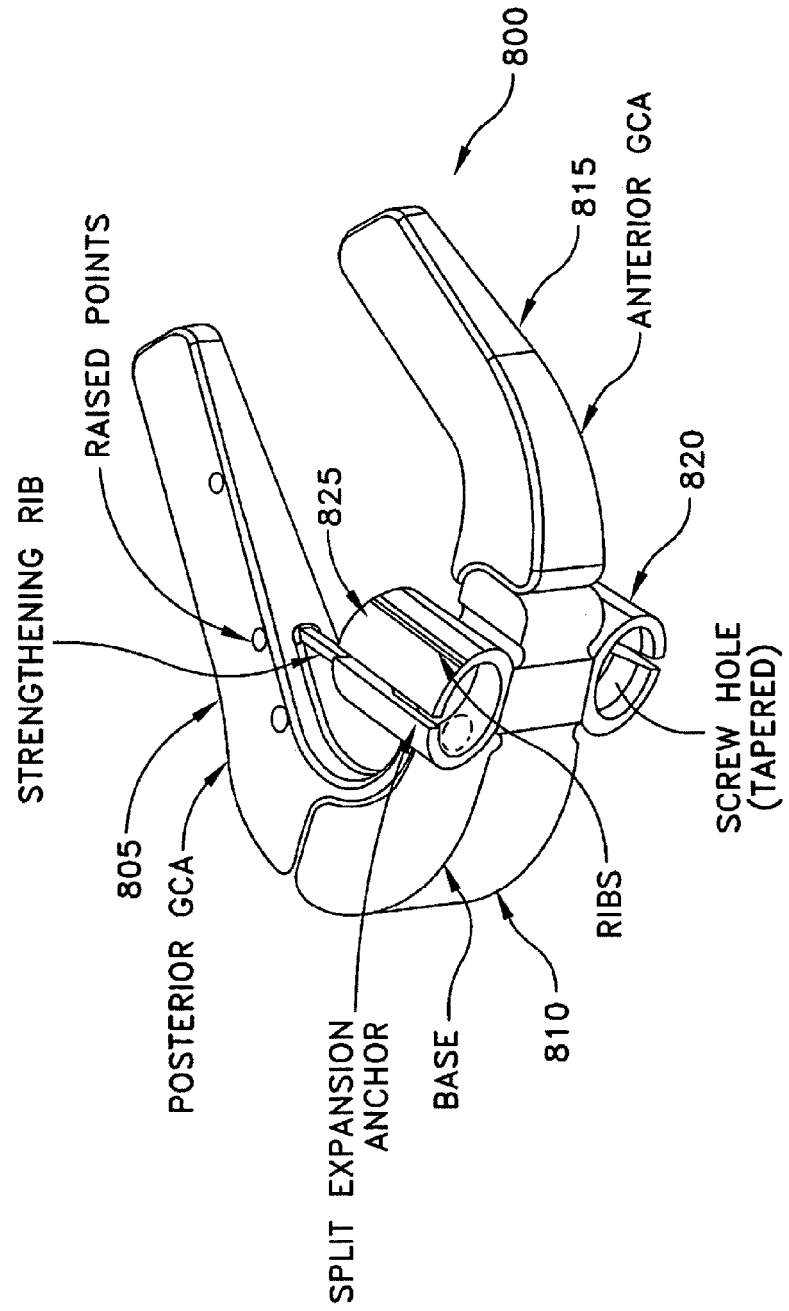

More preferably, however, and looking now at FIG. 24, there is shown a wedge-shaped implant 800 formed in accordance with the present invention. Wedge-shaped implant 800 is characterized by a wedge-like side profile configured to match the geometry of the wedge-like opening 25 (i.e., to match the prescribed correction angle of the open wedge, high tibial osteotomy). Preferably, wedge-shaped implant 800 is also formed so as to have a U-shaped top profile, such that it can form a barrier about the perimeter of the wedge-like opening 25, with the open end of the U-shaped implant positioned against the bony hinge, whereby to contain graft material (e.g., bone paste, bone cement, etc.) which may be positioned within the interior of the wedge-like opening 25. In one preferred form of the present invention, wedge-shaped implant 800 is formed so as to have an asymmetric configuration when viewed in a top view, so as to mate with the geometry of the tibia when the implant is positioned using an antero-medial approach. Wedge-shaped implant 800 is sized so as to match the known distance from the medial aspect of the tibia to the axis 70 of the bony hinge, which is set by the position of apex pin 300. Wedge-shaped implant 800 may be formed out of absorbable material or non-absorbable material, as desired.

Figure 25:
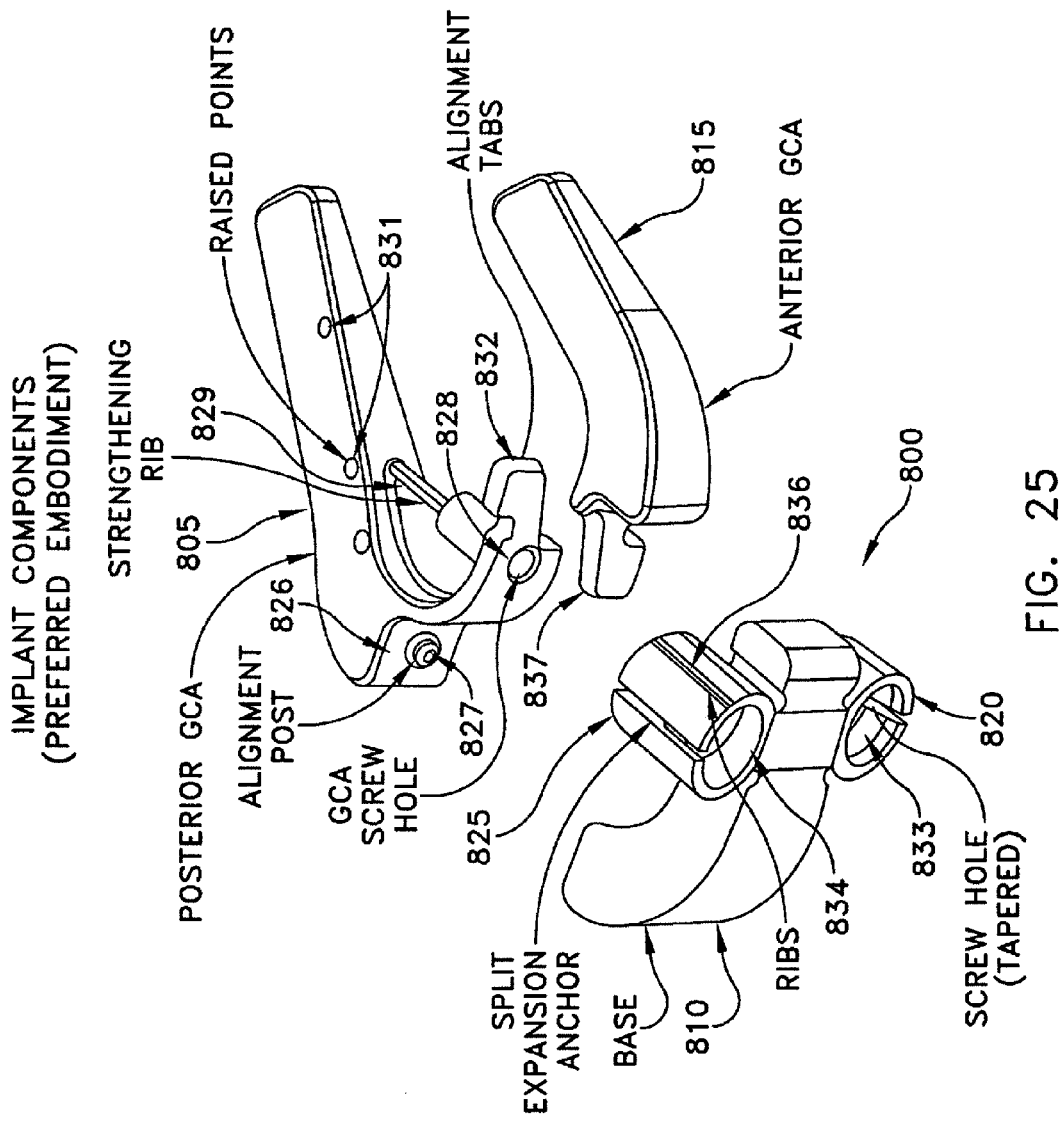
Figure 26:
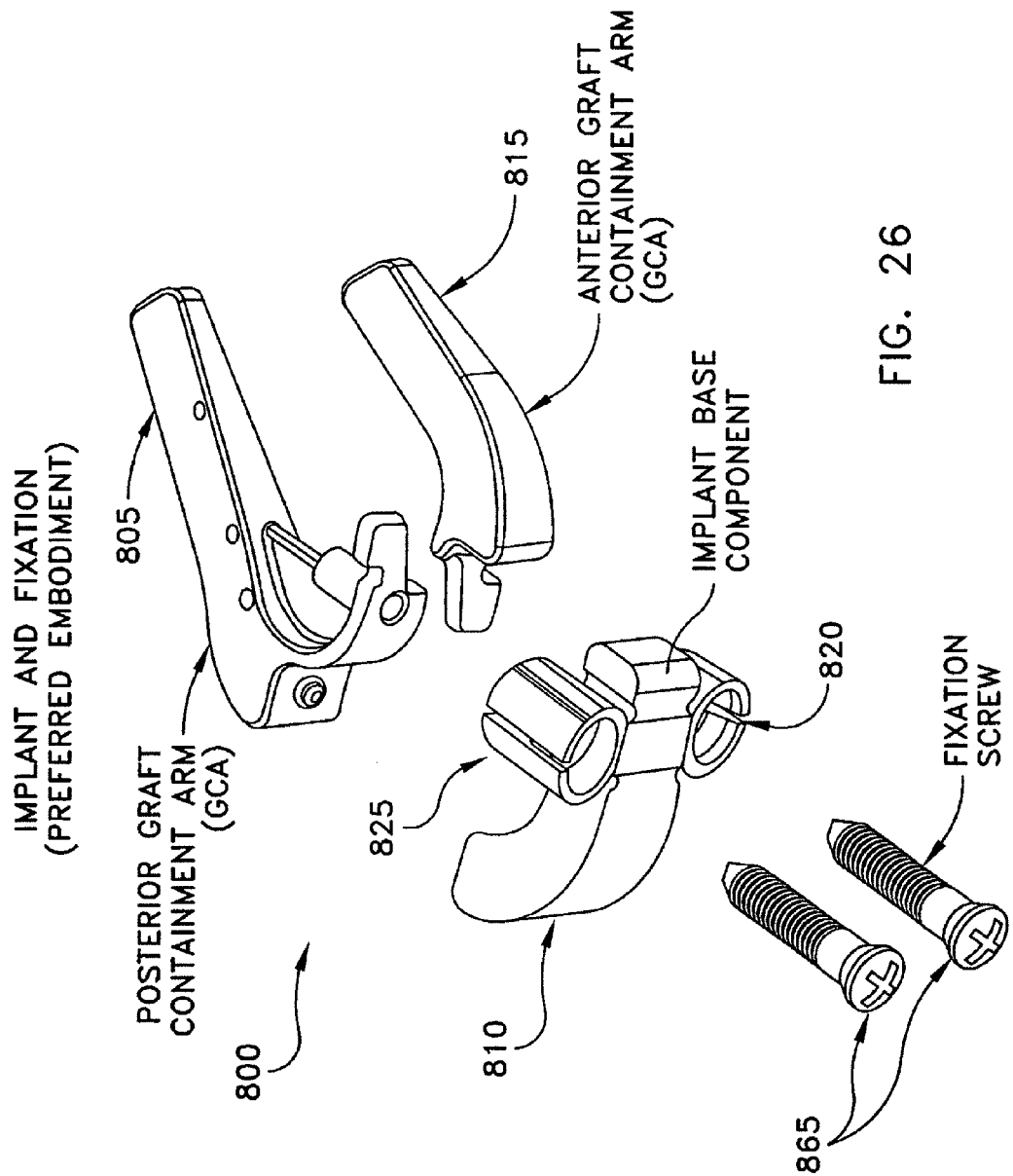

In one preferred form of the invention, and looking now at FIGS. 25 and 26, implant 800 preferably comprises a three-part assembly, comprising posterior graft containment arm (GCA) 805, a base 810 and an anterior graft containment arm (GCA) 815. The individual components of implant 800 may each be formed out of absorbable material and/or non-absorbable material, as desired. Furthermore, where one or more of the implant components is formed out of an absorbable material, the absorption characteristics of the material may vary as desired. By way of example but not limitation, base 810 may be formed out of a relatively slowly-absorbing material, while posterior graft containment arm (GCA) 805 and anterior graft containment arm (GCA) 815 may be formed out of a relatively faster-absorbing material. Base 810 preferably comprises a pair of keys 820, 825. Keys 820, 825 have a disposition which is complementary to the disposition of the keyholes 85, 90, i.e., where keyholes 85, 90 have an "over-under" configuration, keys 820, 825 also have an "over-under" configuration, as will hereinafter be discussed in further detail.

In one preferred form of the invention, implant 800 is formed so that posterior graft containment arm (GCA) 805 has a generally wedge-shaped profile including an engagement seat 826 comprising an alignment post 827, and an introducer hole 828 opening on the antero-medial side of the component for engagement with introducer 845 (see below). A strengthening rib 829 is preferably provided as shown.

Additionally, raised points or dimples 831 may be provided to help fix posterior graft containment arm (GCA) 805 to the bone. An alignment tab 832 is provided for extension into upper keyhole 90 (FIG. 29) when posterior graft containment arm (GCA) 805 is positioned in the wedge-shaped opening 25.

And in one preferred form of the invention, base 805 is formed so that its keys 820, 825 each includes a bore 833, 834, respectively, with the keys being slotted longitudinally so as to permit expansion of the keys when screws 865 are thereafter deployed in the bores, whereby to help lock the implant against the hard cortical bone of the tibia. External ribs 836 may be provided on the outer surfaces of keys 820, 825 so as to help fix keys 820, 825 in keyholes 85, 90, respectively, when keys 820, 825 are expanded, as will hereafter be discussed in further detail. External ribs 836 may extend longitudinally (FIG. 25) or circumferentially (not shown). Keys 820, 825 protrude from the upper and lower surfaces of base implant 810, and accommodate shear loads which may be imposed across the implant. Furthermore, expansion of keys 820, 825 creates an interference fit with the cortical bone of the tibia, and can help support tensile loads which may be imposed across the implant. An alignment mechanism, e.g., a bore (not shown), is provided for mating with alignment post 827 of posterior graft containment arm (GCA) 805.

The bores 833, 834 may be axially aligned with the longitudinal axes of keys 820, 825, respectively. Alternatively, the bores 833, 834 may be arranged so that they diverge from one another, downwardly and upwardly, respectively, so as to direct screws 865 deeper into the adjacent portions of the tibia.

Anterior graft containment arm (GCA) 815 also comprises a generally wedge-shaped profile, and an alignment tab 837 is provided for extension into lower keyhole 85 when GCA 815 is positioned in the wedge-shaped opening 25.

Implant 800 is preferably assembled in situ.

In some instances, it may be advantageous to use an implant trial base 830 (FIGS. 27 and 28) in the course of preparing the tibia to receive implant 800, and in order to confirm proper fit of implant 800 in its seat.

More particularly, a pre-assembled assembly comprising posterior graft containment arm (GCA) 805, an implant trial base 830 and two guide sleeves 835, 840 are first inserted into wedge-like opening 25 in the bone using an introducer 845. See FIGS. 27 and 28.

Figure 27:
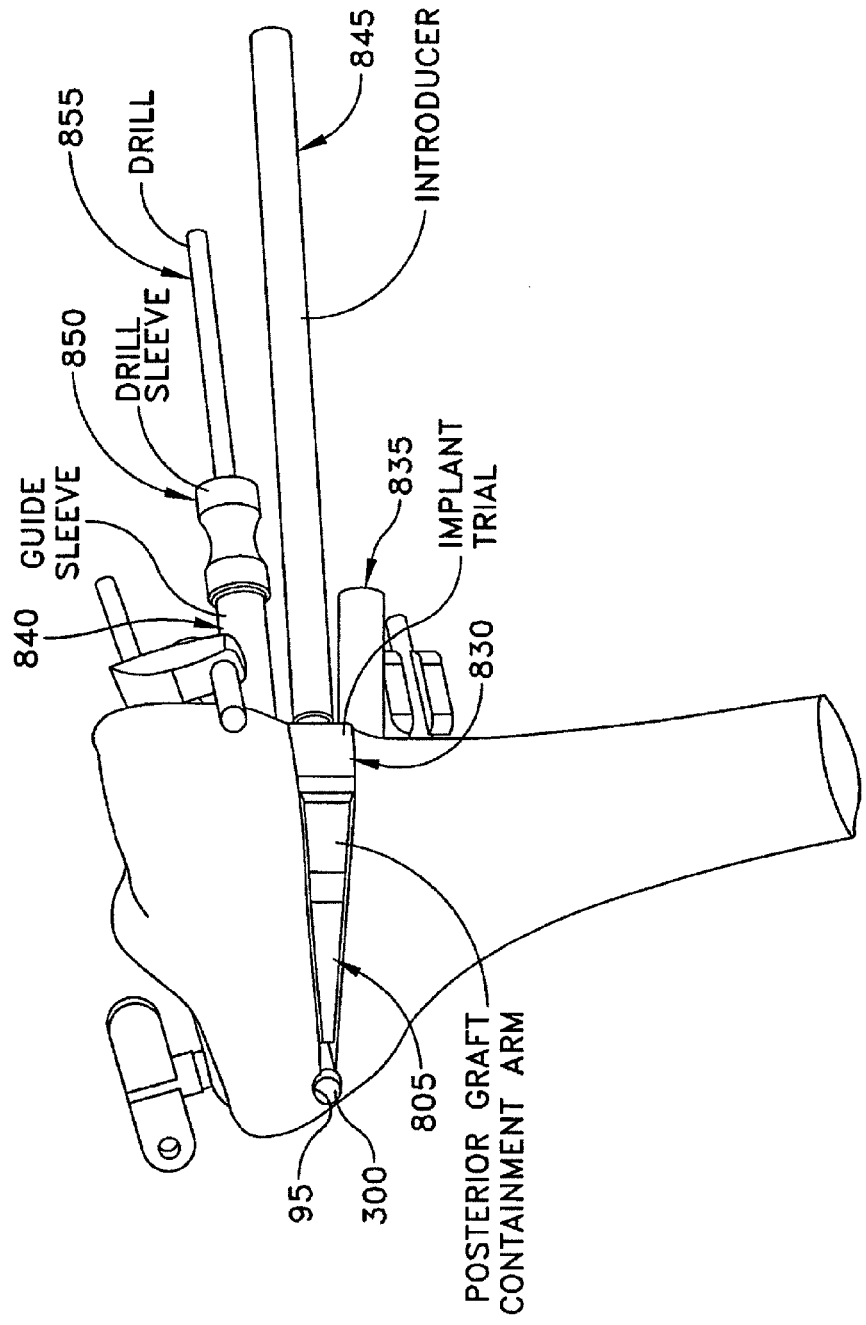
Figure 28:
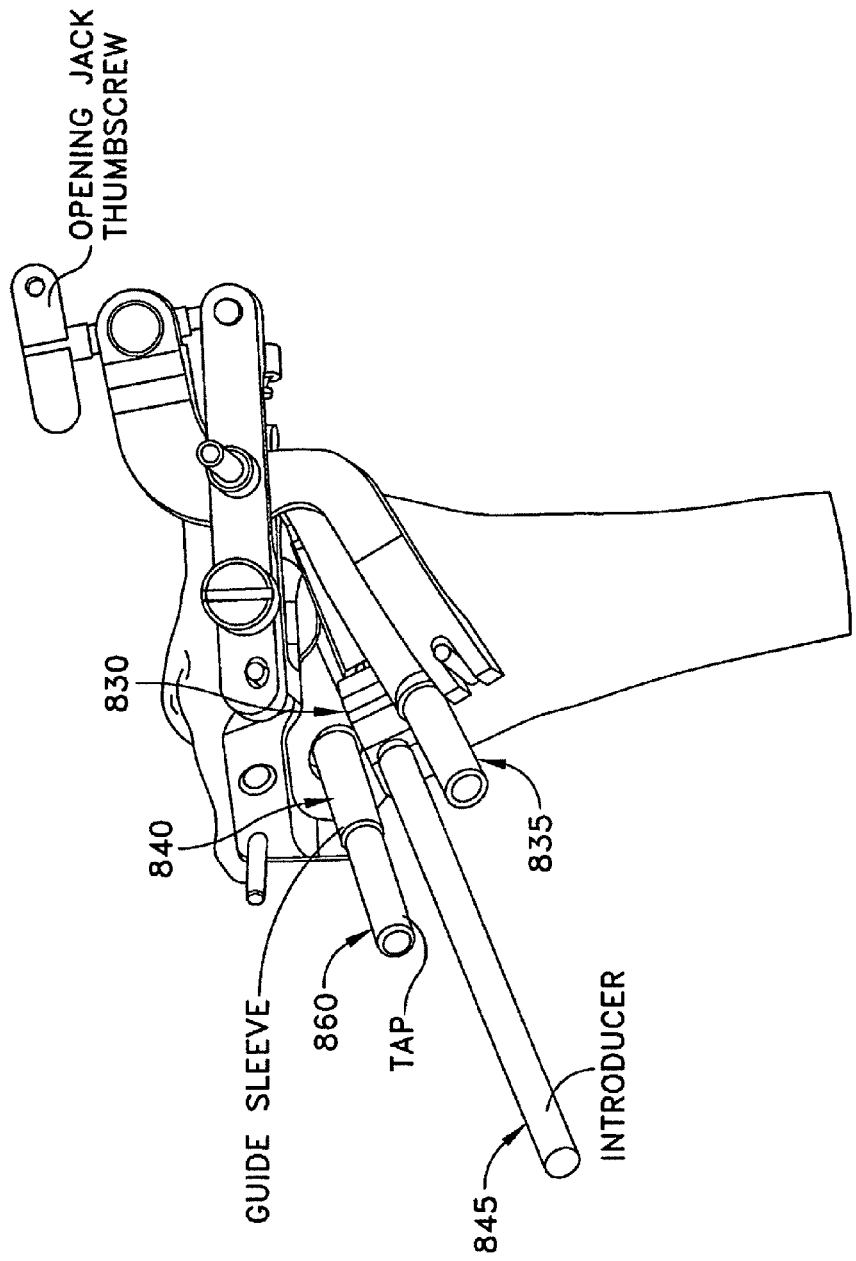

Next, a drill sleeve 850 and a drill 855 are inserted into guide sleeve 840 (FIG. 27). An upper hole is drilled into the tibia with the drill. The drilling procedure is then repeated for guide sleeve 835 so as to create a lower hole. Then drill sleeve 850 and drill 855 are removed from the surgical site. Next, a tap 860 is inserted into guide sleeve 840 and the upper hole is tapped. See FIG. 28. Then the tap is inserted into guide sleeve 835 and the lower hole is tapped. Then tap 860 is removed from the surgical site.

Next, posterior graft containment arm (GCA) 805 is released from introducer 845, and then introducer 845 and implant trial base 830 are removed. Posterior graft containment arm (GCA) 805 remains in wedge-like opening 25.

Then, if desired, graft material is packed into the osteotomy opening.

Next, anterior graft containment arm (GCA) 815 is placed into the osteotomy opening and aligned with the prepared implant holes. See FIG. 29. If necessary, jack screw 735 is rotated as needed so as to facilitate insertion of anterior GCA 815. At this point in the procedure, posterior graft containment arm (GCA) 805 and anterior graft containment arm (GCA) 815 are positioned in wedge-like opening 25.

Then implant base 810 is inserted into the prepared osteotomy, with keys 820 and 825 seated in tibial holes 85 and 90, respectively, and with base 810 capturing posterior graft containment arm (GCA) 805 and anterior graft containment arm (GCA) 815 against the bony hinge. Keys 820 and 825, seating in keyholes 85 and 90, help ensure a precise fit of the implant to the bone. As this is done, jack screw 735 is adjusted as necessary so as to facilitate insertion of the base into the osteotomy. Then jack screw 735 is tightened slightly so as to ensure that the implant components are fully seated into the osteotomy wedge, with at least implant base 810, and preferably also posterior graft containment arm (GCA) 805 and anterior graft containment arm (GCA) 815, providing load bearing support to the tibia. Next, fixation screws 865 are inserted through keys 820 and 825 in base 810 and into the tapped holes in the tibia, and then tightened into place. As this occurs, fixation screws 865 expand keys 820, 825 within keyholes 85, 90 so as to lock keys 820, 825 to the adjacent cortical bone, and fixation screws 865 extend into the tibia, so as to further lock the implant in position. See FIG. 30. Finally, opening jack 700, positioning guide 100, apex pin 300, distal pin 410, frontal pin 145 and A-M pin 150 are removed from the surgical site, and the incision closed.

Providing implant 800 with two graft containment arms, e.g., posterior graft containment arm (GCA) 805 and anterior graft containment arm (GCA) 815, is frequently preferred. However, in some circumstances, it may be desirable to omit one or both of posterior graft containment arm (GCA) 805 and anterior graft containment arm (GCA) 815. Thus, in one preferred form of the invention, implant 800 comprises only base 810 and omits both posterior graft containment arm (GCA) 805 and anterior graft containment arm (GCA) 815.

Providing implant 800 with a pair of keys 820, 825 is generally preferred. However, in some circumstances, it may be desirable to omit one or the other, or both, of keys 820, 825. Furthermore, in other circumstances, it may be desirable to provide more than two keys, e.g., to provide three keys.

Furthermore, each of the keys 820, 825 may include more than one bore 833, 834. Thus, for example, a key may include two bores, one angled leftwardly so as to direct a fixation screw leftwardly into the tibia to the left of the key, and/or one angled rightwardly so as to direct a fixation screw rightwardly into the tibia to the right of the key.

The use of apex pin 300 is significant for a number of reasons:

(1) the oversized, circular diameter hole 95 (FIG. 23A) formed in the tibia by apex pin 300, which forms the limit of bone cut 20, effectively displaces the stress forces created at the edge of the bony hinge when the cut is opened to form the wedge-like opening 25, thereby adding significantly to the effective strength of the bony hinge;

(2) by using apex pin 300 to control the length of bone cut 20 (as measured from the medial aspect of the tibia to the apex pin), the seat for the implant is always of known size, thereby simplifying proper fitting of the implant to its seat in the bone, and also reducing the inventory of different-sized implants which must be on hand during the surgery;

(3) with apex pin 300 in place, bone resecting tools can be used with increased confidence, without fear of inadvertently cutting into, or even through, the bony hinge; and (4) since apex pin 300 controls the depth of bone cut 20, the implant can be reliably manufactured to appropriately address the required degree of correction needed to effect knee realignment (e.g., a 4 degree implant slope will always provide a 4 degree angle of correction).

Furthermore, the provision of (i) apex pin 300, posterior protector 500 and tibial tubercle locating tab 135 creates a "protection zone", and (ii) cutting guide 600 creates a closely constrained cutting path for saw blade 625, thereby together ensuring that only the desired portion of the bone is cut. Among other things, the provision of posterior protector 500 ensures that the delicate neurological and vascular tissues at the back of the knee are protected during cutting of the tibia.

The provision of keyholes 85, 90 in the tibia, and the provision of keys 820, 825 in the implant, is significant inasmuch as they provide improved stabilization of the implant, particularly against rotational and shearing forces. This is particularly true inasmuch as keyholes 85, 90 extend through the hard cortical bone at the periphery of the tibia.

Implant with "Side-by-Side" Key Configuration

Figure 31:
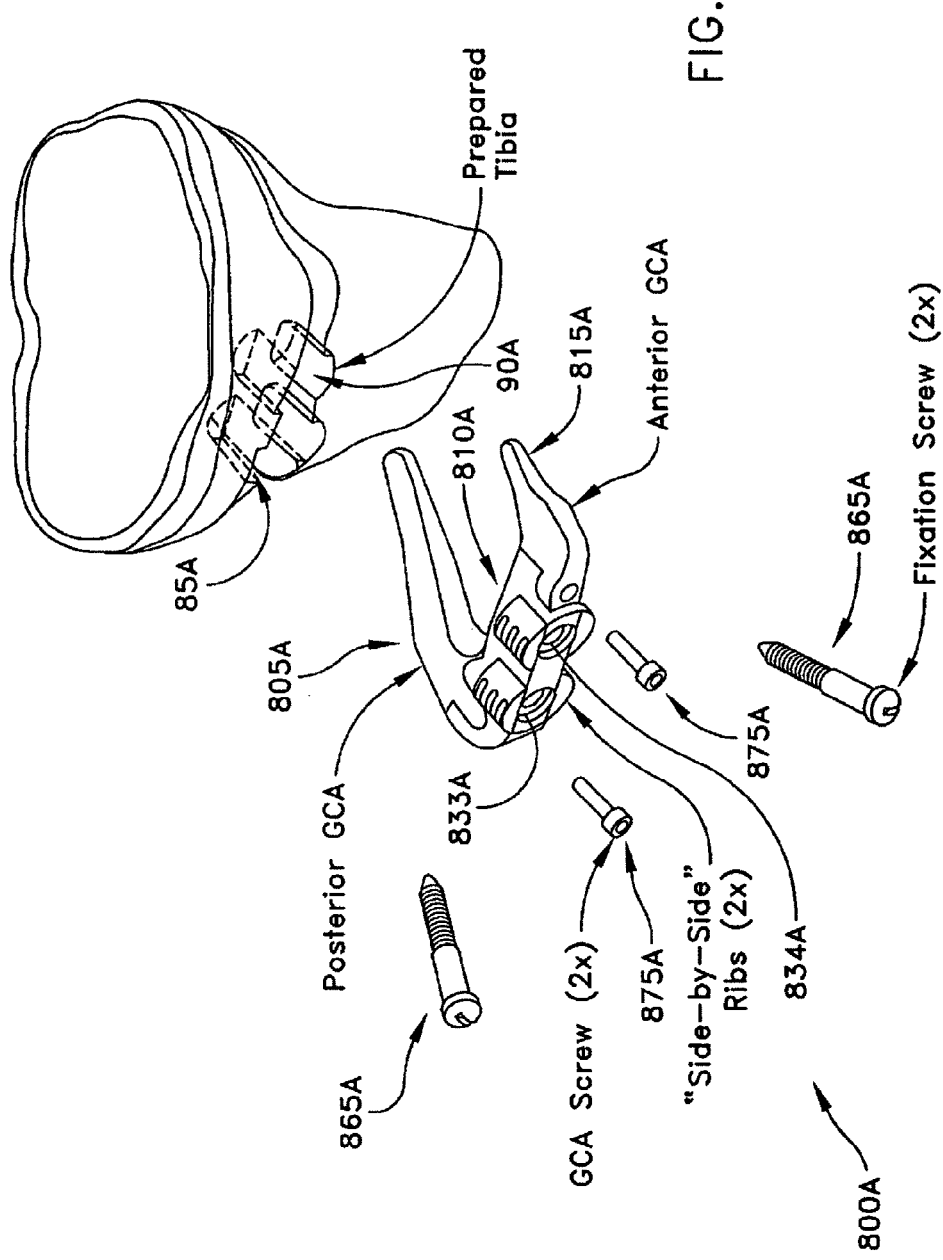
Figure 33:
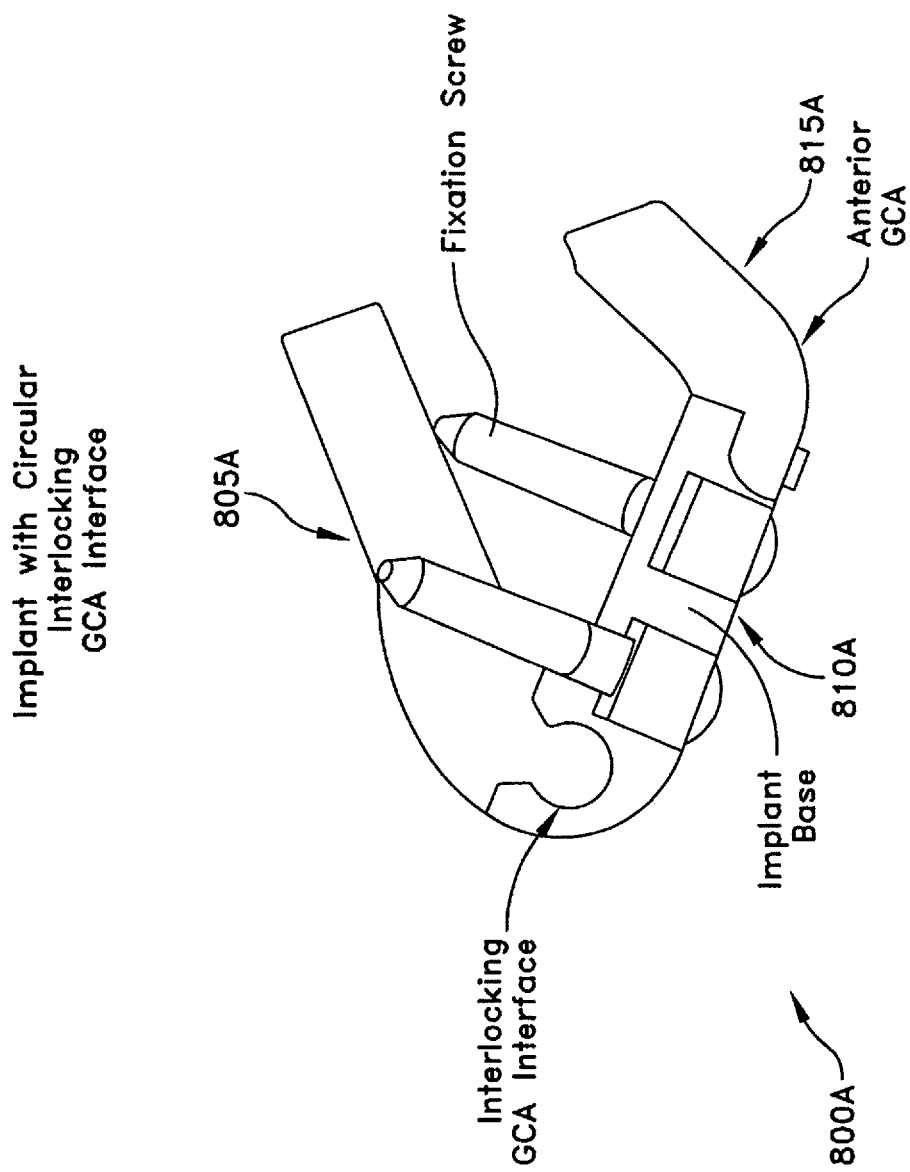

Looking next at FIGS. 31-33, there is shown an implant 800A also formed in accordance with the present invention. Implant 800A is generally similar to the implant 800 disclosed above, except that implant 800A has its keys disposed in a "side-by-side" configuration, rather than the "over-under" key configuration of implant 800, as will hereinafter be discussed in further detail. Furthermore, implant 800A also provides an alternative approach for joining the posterior graft containment arm (GCA) to the base, and an alternative approach for joining the anterior graft containment arm (GCA) to the base, as will hereinafter also be discussed in further detail.

More particularly, and still looking now at FIGS. 31-33, implant 800A comprises a posterior graft containment arm (GCA) 805A, a base 810A and an anterior graft containment arm (GCA) 815A. Base 810A preferably comprises a pair of keys 820A, 825A. Keys 820A, 825A are laterally displaced along the width of base 810A, in a "side-by-side" configuration. This is in contrast to the construction of implant 800, which uses an "over-under" configuration for its keys 820, 825 (FIG. 24). Among other things, it has been found that the "side-by-side" configuration provides, at the base of the implant, excellent load-bearing characteristics and substantial resistance to rotational and shear forces.

Posterior graft containment arm (GCA) 805A includes a tab 870A, and base 810A includes a groove 873A, whereby posterior graft containment arm (GCA) 805A can mate with base 810A. A screw 875A is used to secure tab 870A in groove 873A, and hence posterior graft containment arm (GCA) 805 to base 810. Anterior graft containment arm (GCA) 815A includes a flange 878A, and implant base 810A includes a recess 881A, whereby anterior graft containment arm (GCA) 815A can mate with base 810A. Another screw 875A is used to secure flange 878A in recess 881A, and hence anterior graft containment arm (GCA) 815 to base 810.

Posterior graft containment arm (GCA) 805A, and/or anterior graft containment arm (GCA) 815A, may include raised points or dimples 831A.

Keys 820A, 825A each include a bore 833A, 834A, respectively. Bores 833A, 834A receive fixation screws 865A for fixing implant 800A to the tibia. Bores 833A, 834A preferably diverge from the longitudinal axes of keys 820A, 825A, respectively, so as to direct fixation screws 865A downwardly or upwardly into the adjacent portions of the tibia. Keys 820A, 825A may also include external ribs 836A. External ribs 836A may extend longitudinally (not shown) or circumferentially (FIG. 32). Keys 820A, 825A may also be slotted (i.e., in a manner analogous to the slots provided in keys 820, 825 of implant 800), whereby to permit keys 820A, 825A to expand when fixation screws 865A are received in bores 833A, 834A.

Figure 34:
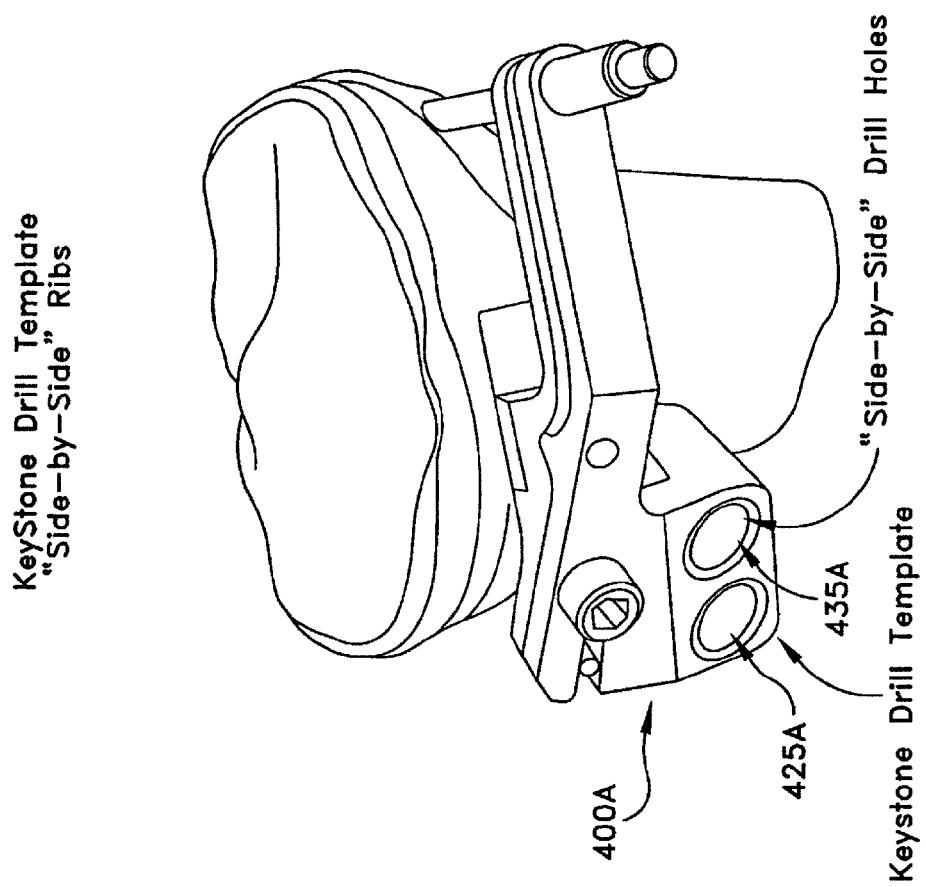
FIG. 34 is a schematic view showing a keyhole drill guide which may be used in conjunction with the wedge-shaped implant shown in FIGS. 31-33.

In order to provide appropriate keyholes 85A, 90A (FIG. 31) for receiving keys 820A, 825A, a keyhole drill guide 400A (also sometimes referred to as a "keystone drill template") may be used (FIG. 34). Keyhole drill guide 400A is generally similar to the keyhole drill guide 400 disclosed above, except that keyhole drill guide 400A has its two guide holes 425A, 435A disposed in a "side-by-side" disposition, rather than the "over-under" disposition of the two guide holes 425, 435 of drill guide 400.

Implant 800A (and drill guide 400A) may be used in an open wedge, high tibial osteotomy in a manner which is generally similar to that previously described with respect to implant 800 (and drill guide 400).

Providing implant 800A with two graft containment arms, e.g., posterior graft containment arm (GCA) 805A and anterior graft containment arm (GCA) 815A, is frequently preferred. However, in some circumstances, it may be desirable to omit one or both of posterior graft containment arm (GCA) 805A and anterior graft containment arm (GCA) 815A. Thus, in one preferred form of the invention, implant 800A comprises only base 810A and omits both posterior graft containment arm (GCA) 805A and anterior graft containment arm (GCA) 815A.

Providing implant 800A with a pair of keys 820A, 825A is generally preferred. However, in some circumstances, it may be desirable to omit one or the other, or both, of keys 820A, 825A. Furthermore, in other circumstances, it may be desirable to provide more than two keys, e.g., to provide three keys.

Furthermore, each of the keys 820A, 825A may include more than one bore 833A, 834A. Thus, for example, a key may include two bores, one angled upwardly so as to direct a fixation screw upwardly into the tibia above the key, and/or one angled downwardly so as to direct a fixation screw downwardly into the tibia below the key.

Figure 35:
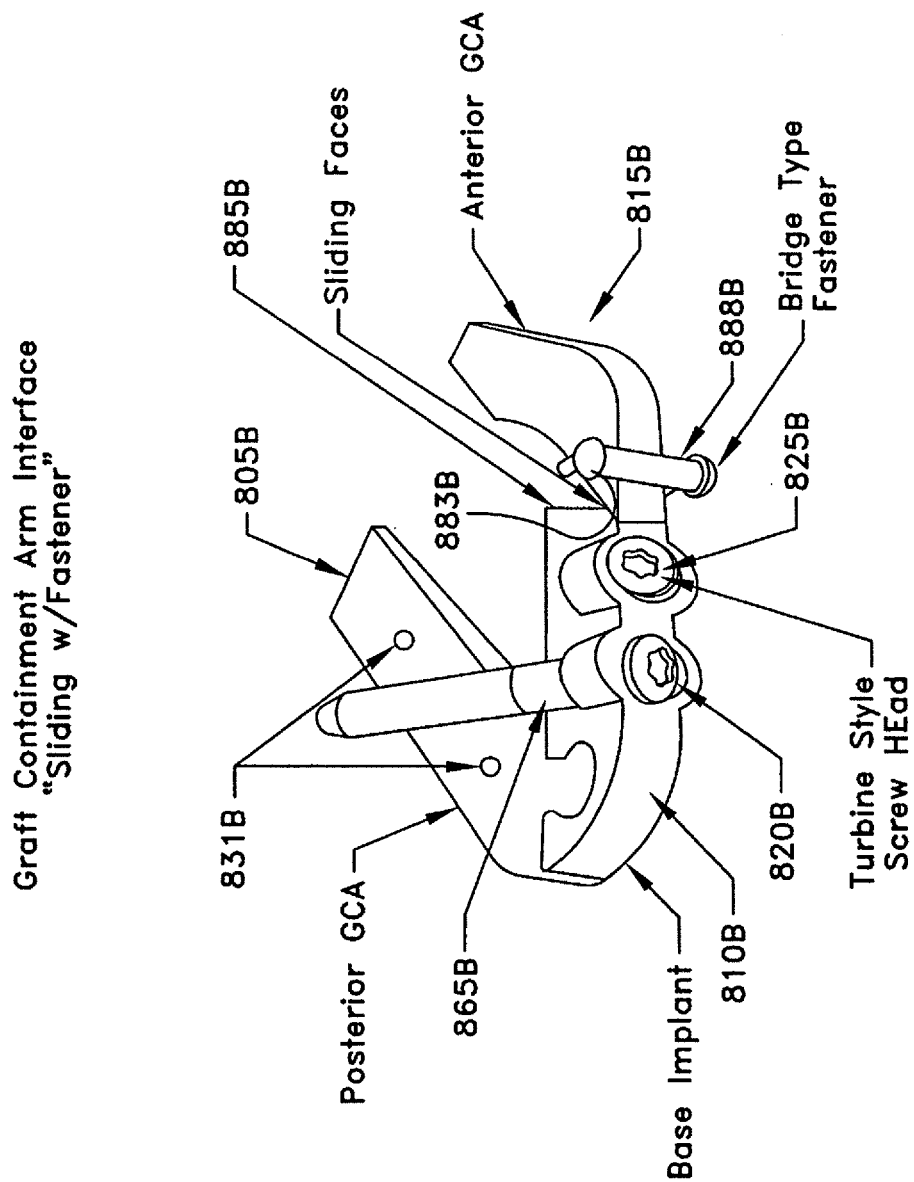
FIG. 35 is a schematic view showing another wedge-shaped implant formed in accordance with the present invention.

Implant with Alternative Approach for Joining Anterior Graft Containment Arm (GCA) to Implant Base Looking next at FIG. 35, there is shown another implant 800B also formed in accordance with the present invention. Implant 800B is generally similar to the implant 800A disclosed above, except that implant 800B provides an alternative approach for joining the anterior graft containment arm (GCA) to the implant base, among other things.

More particularly, and still looking now at FIG. 35, implant 800B comprises a posterior graft containment arm (GCA) 805B, a base 810B and an anterior graft containment arm (GCA) 815B. Base 810B preferably comprises a pair of keys 820B, 825B. Keys 820B, 825B are laterally displaced along the width of base 810B, in a "side-by-side" configuration. Again, this is in contrast to the construction of implant 800, which uses an "over-under" configuration for its keys 820, 825 (FIG. 24).

Posterior graft containment arm (GCA) 805B includes a tab 870B, and base 810B includes a groove 873B, whereby posterior graft containment arm (GCA) 805B can mate with base 810B. Anterior graft containment arm (GCA) 815A includes a slide face 883B, and implant base 810B includes an opposing slide face 885B, whereby anterior graft containment arm (GCA) 815B can mate with base 810B. A bridge-type fastener 888B is used to secure anterior graft containment arm (GCA) 815B in position, with arm slide face 883B engaging base slide face 885B, after the implant is positioned within positioned within the wedge-like opening 25.

Posterior graft containment arm (GCA) 805B, and/or anterior graft containment arm (GCA) 815B, may include raised points or dimples 831B.

Keys 820B, 825B each include a bore 833B, 834B, respectively. Bores 833B, 834B receive fixation screws 865B for fixing implant 800B to the tibia. Bores 833B, 834B preferably diverge from the longitudinal axes of keys 820B, 825B, respectively, so as to direct fixation screws 865B downwardly or upwardly into the adjacent portions of the tibia. Keys 820B, 825B may also include external ribs 836B. External ribs 836B may extend longitudinally or circumferentially. Keys 820B, 825B may also be slotted (i.e., in a manner analogous to the slots provided in keys 820, 825 of implant 800), whereby to permit keys 820B, 8258 to expand when fixation screws 865B are received in bores 833B, 834B.

Implant 800B may be used in an open wedge, high tibial osteotomy in a manner which is generally similar to that previously described with respect to implant 800.

Providing implant 800B with two graft containment arms, e.g., posterior graft containment arm (GCA) 805B and anterior graft containment arm (GCA) 815B, is frequently preferred. However, in some circumstances, it may be desirable to omit one or both of posterior graft containment arm (GCA) 805B and anterior graft containment arm (GCA) 815B. Thus, in one preferred form of the invention, implant 800B comprises only base 810B and omits both posterior graft containment arm (GCA) 805B and anterior graft containment arm (GCA) 815B.

Providing implant 800B with a pair of keys 820B, 825B is generally preferred. However, in some circumstances, it may be desirable to omit one or the other, or both, of keys 820B, 825B. Furthermore, in other circumstances, it may be desirable to provide more than two keys, e.g., to provide three keys.

Furthermore, each of the keys 820B, 825B may include more than one bore 833B, 834B. Thus, for example, a key may include two bores, one angled upwardly so as to direct a fixation screw upwardly into the tibia above the key, and/or one angled downwardly so as to direct a fixation screw downwardly into the tibia below the key.

Implant with Shear Rib

Figure 36:
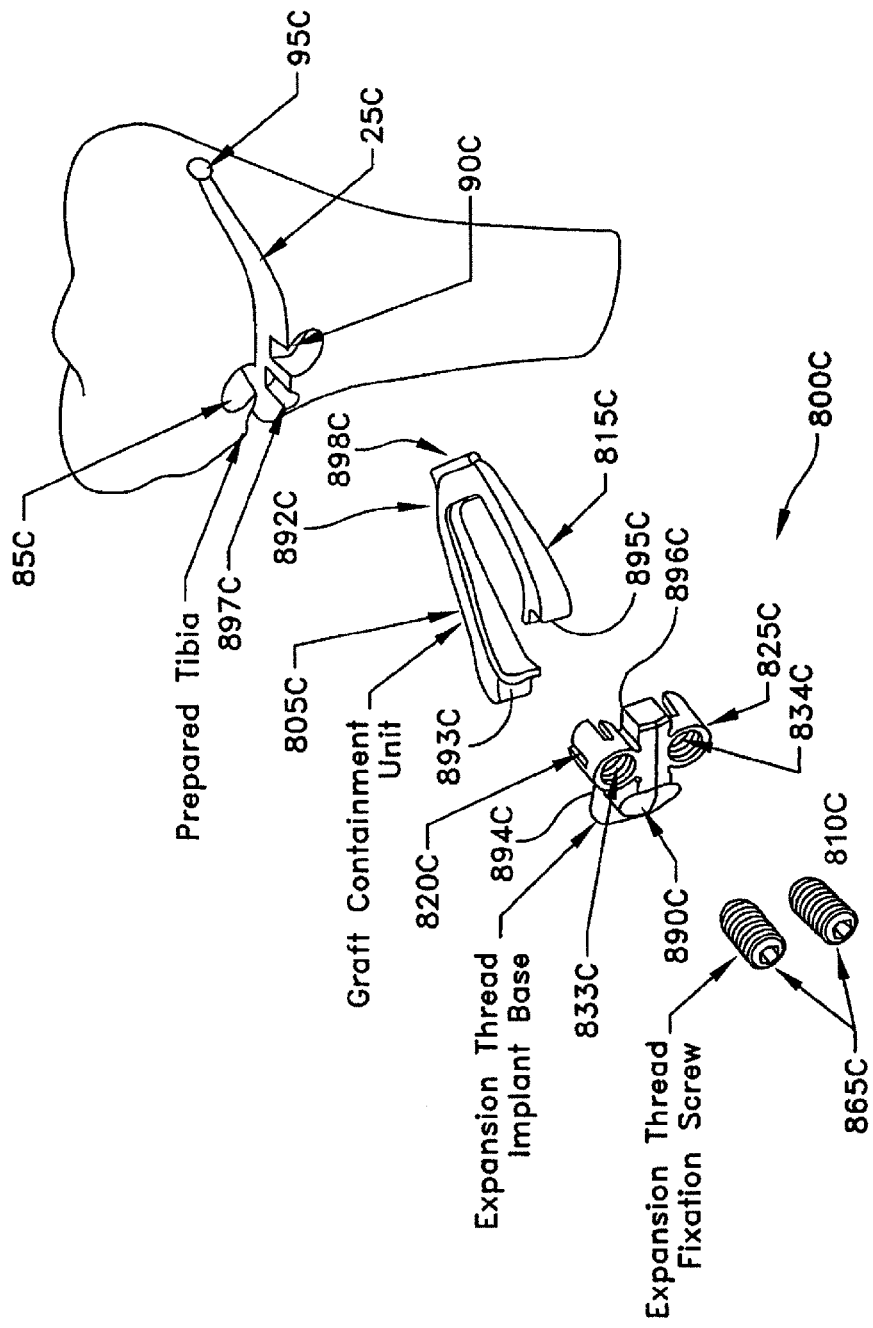
FIGS. 36-38 are schematic views showing still another wedge-shaped implant formed in accordance with the present invention.
Figure 37:
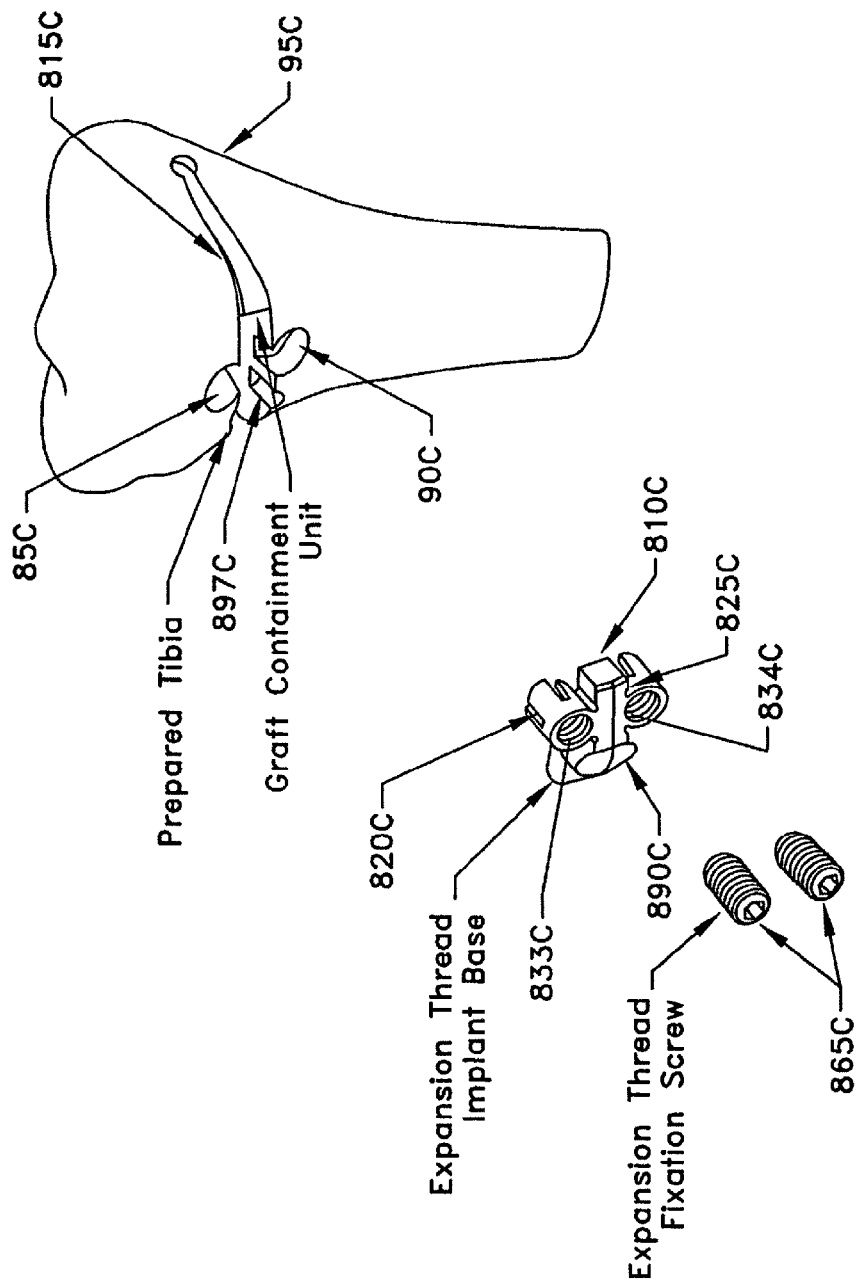
Figure 38:
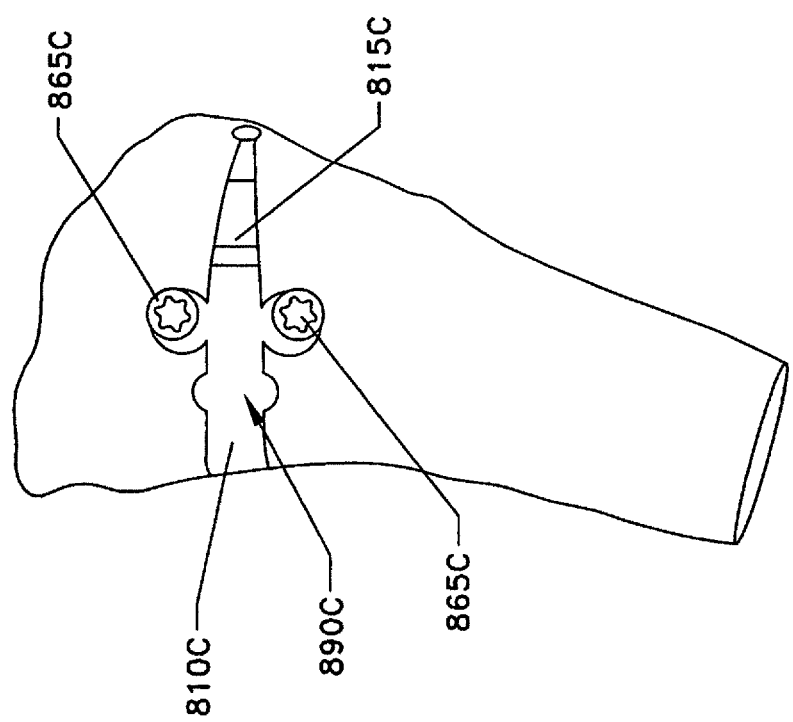

Looking next at FIGS. 36-38, there is shown an implant 800C also formed in accordance with the present invention. Implant 800C is generally similar to the implant 800 disclosed above, except that implant 800C has a shear rib 890C on its base, laterally displaced from the two keys (which are themselves arranged in an "over-under" configuration), as will hereinafter be discussed in further detail. Furthermore, implant 800C also provides an alternative approach for joining the posterior graft containment arm (GCA) to the base, and an alternative approach for joining the anterior graft containment arm (GCA) to the base, as will hereinafter also be discussed in further detail. Furthermore, implant 800C also provides a means for joining the distal end of posterior graft containment arm (GCA) 805C to the distal end of anterior graft containment arm (GCA) 815C, as will hereinafter also be discussed in further detail.

More particularly, and still looking now at FIGS. 36-38, implant 800C comprises a posterior graft containment arm (GCA) 805C, a base 810C and an anterior graft containment arm (GCA) 815C. Preferably a bridge 892C connects the distal end of posterior graft containment arm (GCA) 805C with the distal end of anterior graft containment arm (GCA) 815C. If desired, bridge 892C may be provided with a distal tab 898C to be received in oversized hole 95C. Distal tab 898C serves to improve the alignment and stability of implant 800C when seated in wedge-like opening 25C. A shear rib 890C is formed in base 810C, laterally displaced from the two keys 820C, 825C, which are arranged in an "over-under" configuration.

Posterior graft containment arm (GCA) 805C includes a recess 893C, and base 810C includes a shoulder 894C, whereby posterior graft containment arm (GCA) 805C can mate with base 810C. Anterior graft containment arm (GCA)

815C includes a recess 895C, and implant base 810C includes a shoulder 896C, whereby anterior graft containment arm (GCA) 815C can mate with base 810C.

Posterior graft containment arm (GCA) 805C, and/or anterior graft containment arm (GCA) 815C, may include raised points or dimples 831C.

Keys 820C, 825C each include a bore 833C, 834C, respectively. Bores 833C, 834C receive fixation screws 865C for fixing implant 800C to the tibia. The bores 833C, 834C may be axially aligned with the longitudinal axes of keys 820C, 825C, respectively. Alternatively, the bores 833C, 834C may be arranged so that they diverge from one another, downwardly and upwardly, respectively, so as to direct screws 865C deeper into the adjacent portions of the tibia. Keys 820C, 825C may also include external ribs 836C. External ribs 836C may extend longitudinally or circumferentially. Keys 820C, 825C may also be slotted (i.e., in a manner analogous to the slots provided in keys 820, 825 of implant 800), whereby to permit keys 820C, 825C to expand when fixation screws 865C are received in bores 833C, 834C.

Shear rib 890C is laterally offset from keys 820C, 825C. Shear rib 890C projects above and below the top and bottom surfaces of base 810C. Among other things, it has been found that the provision of shear rib 890C provides, at the base of the implant, excellent load-bearing characteristics and substantial resistance to rotational and shear forces.

Figure 39:
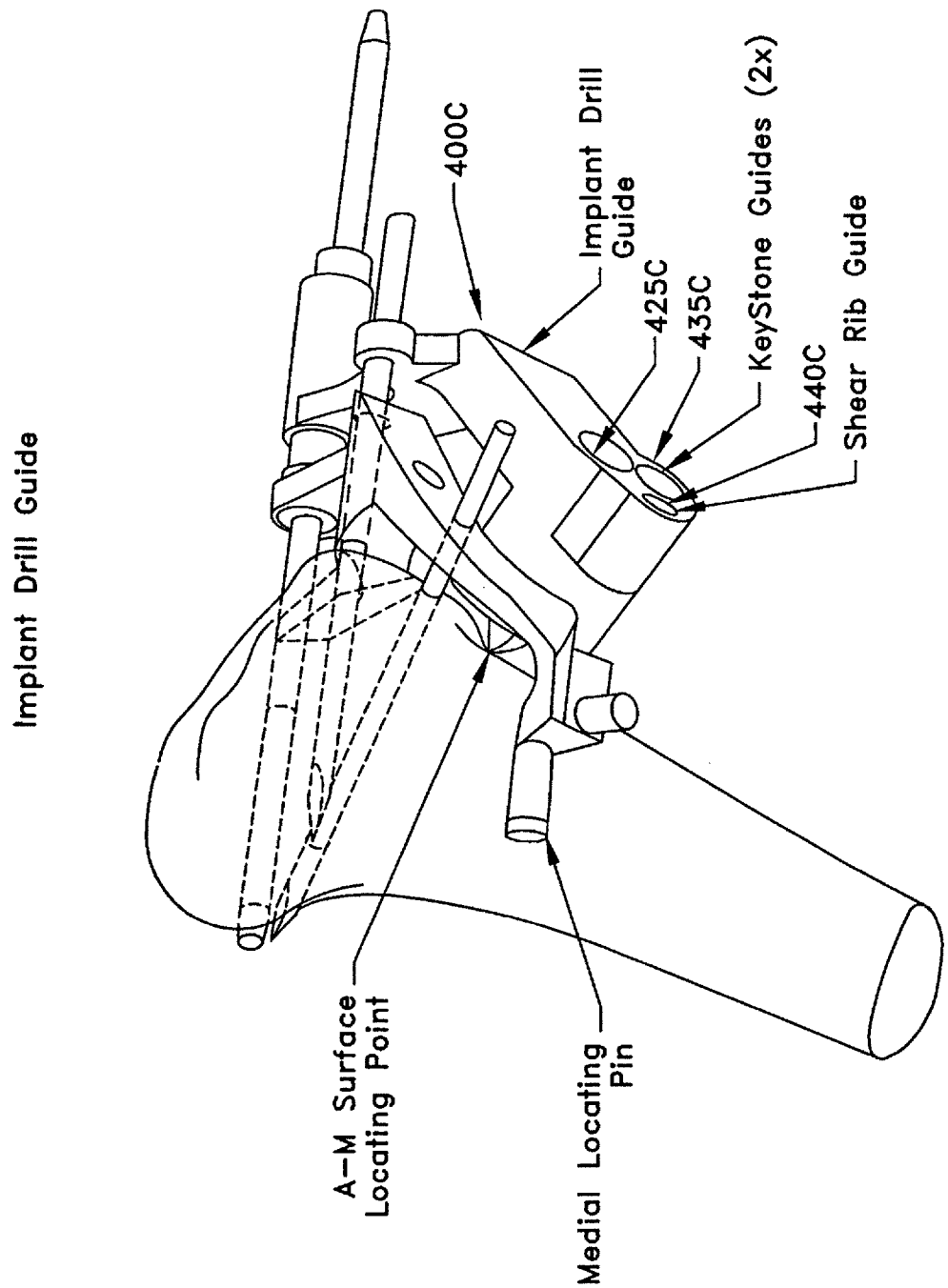
FIGS. 39-41 are schematic views showing a keyhole drill guide and an end mill which may be used in conjunction with the wedge-shaped implant shown in FIGS. 36-38.
Figure 40:
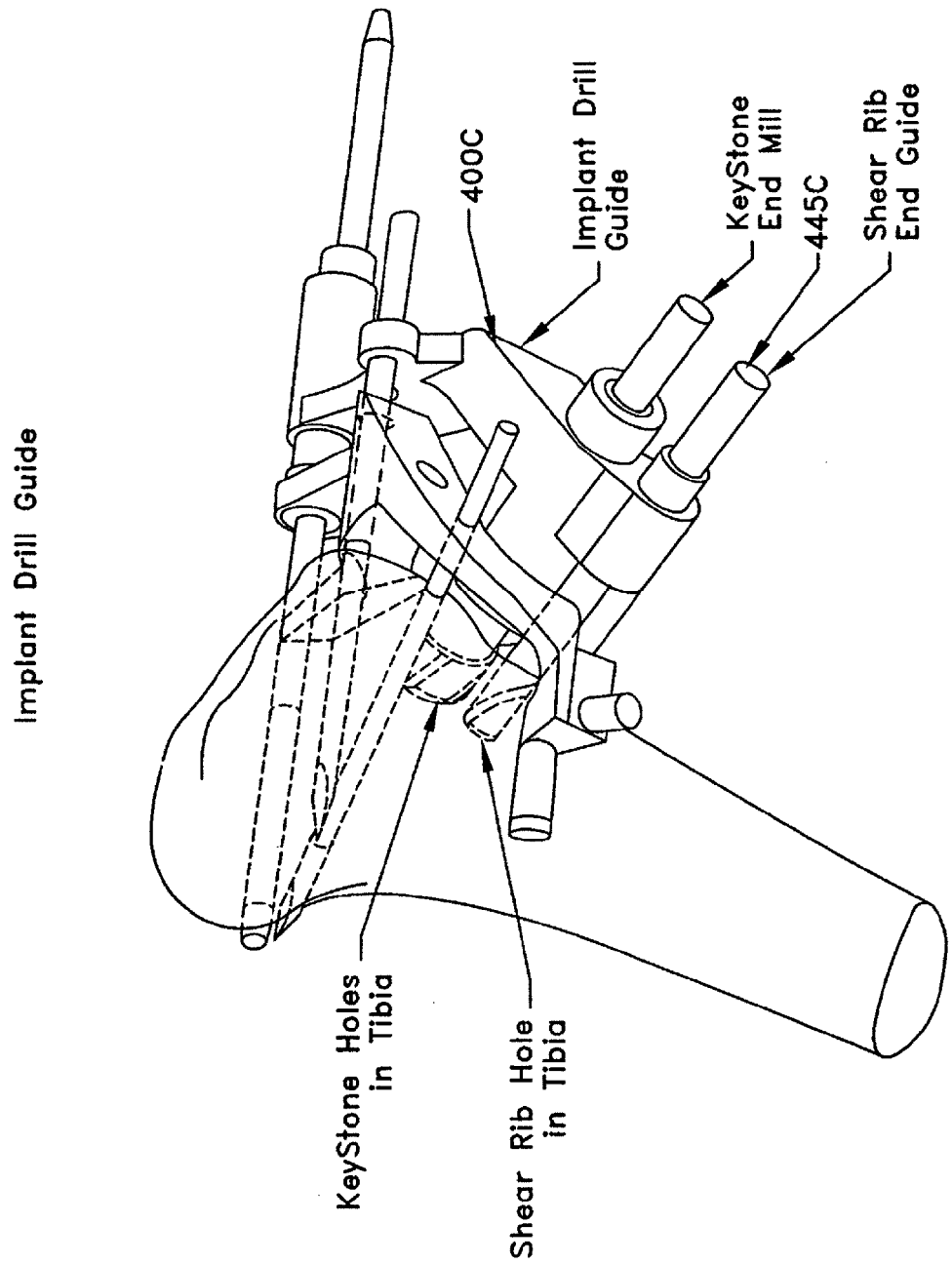

In order to provide appropriate keyholes 85C, 90C (FIG. 36) for receiving keys 820C, 825C, and also for providing a shear rib keyhole 897C for receiving shear rib 890C, a keyhole drill guide 400C (also sometimes referred to as a "keystone guide") may be used (FIGS. 39 and 40). Keyhole drill guide 400C is generally similar to the keyhole drill guide 400 disclosed above, except that keyhole drill guide 400C has, in addition to its two guide holes 425C, 435C, a shear rib guidehole 440C for forming shear rib keyhole 897C.

Implant 800C (and drill guide 400C) may be used in an open wedge, high tibial osteotomy in a manner which is generally similar to that previously described with respect to implant 800 (and drill guide 400), except that the bridged graft containment unit, i.e., posterior graft containment arm (GCA) 805C, bridge 892C and anterior graft containment arm (GCA) 815C, is installed as a single construction. Furthermore, when drill guide 400C is used to form keyholes 85C and 90C, it is also used to form shear rib keyhole 897C.

Providing implant 800C with two graft containment arms, e.g., posterior graft containment arm (GCA) 805C and anterior graft containment arm (GCA) 815C, is frequently preferred. However, in some circumstances, it may be desirable to omit one or both of posterior graft containment arm (GCA) 805C and anterior graft containment arm (GCA) 815C. Thus, in one preferred form of the invention, implant 800C comprises only base 810C and omits both posterior graft containment arm (GCA) 805C and anterior graft containment arm (GCA) 815C.

Providing implant 800C with a pair of keys 820C, 825C is generally preferred. However, in some circumstances, it may be desirable to omit one or the other, or both, of keys 820C, 825C. Furthermore, in other circumstances, it may be desirable to provide more than two keys, e.g., to provide three keys.

Furthermore, each of the keys 820C, 825C may include more than one bore 833C, 834C. Thus, for example, a key may include two bores, one angled leftwardly so as to direct a fixation screw leftwardly into the tibia to the left of the key, and/or one angled rightwardly so as to direct a fixation screw rightwardly into the tibia to the right of the key.

Figure 41:
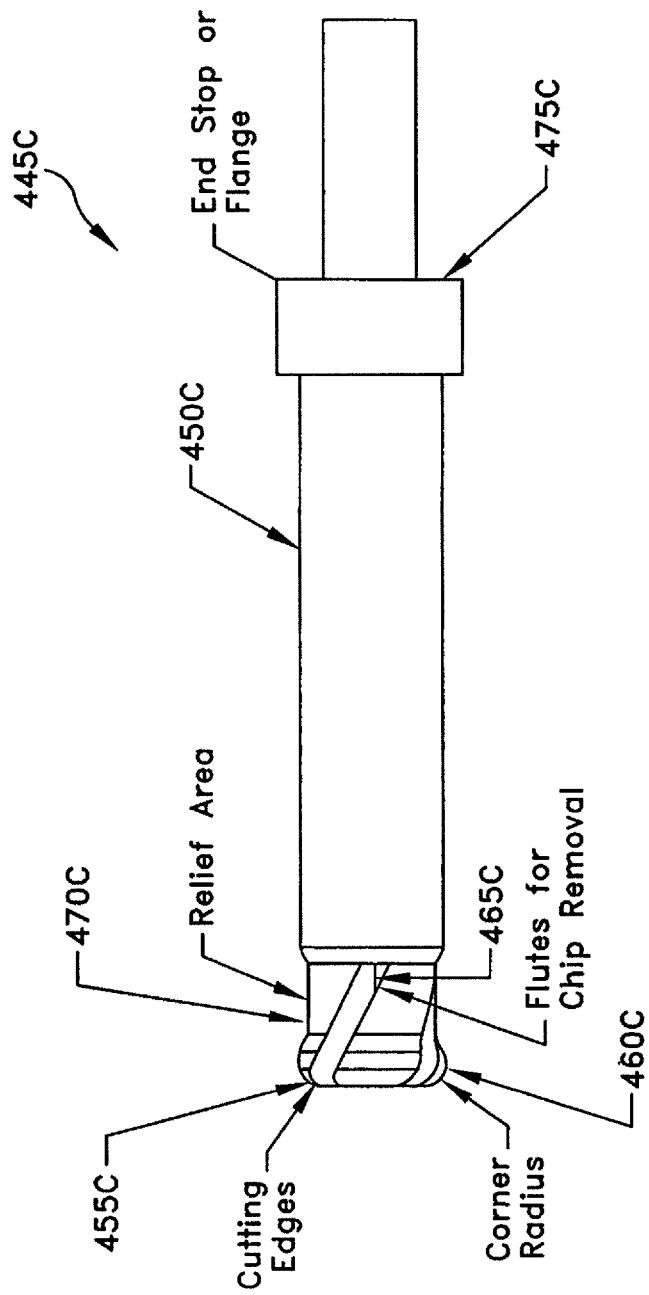

If desired, shear rib keyhole 897C can be formed using a conventional drill. More preferably, however, and looking now at FIGS. 40 and 41, shear rib keyhole 897C is formed using a shear rib end mill 445C. Shear rib end mill 445C generally comprises a shaft 450C having cutting edges 455C, a corner radius 460C and flutes 465C. A relief area 470C is formed just proximal to corner radius 460C. An end stop 475C limits, through engagement with drill guide 400C, the depth of shear rib keyhole 897C.

Implant with Expansion Thread Fixation Screws which Terminate within the Keys

Figure 42:
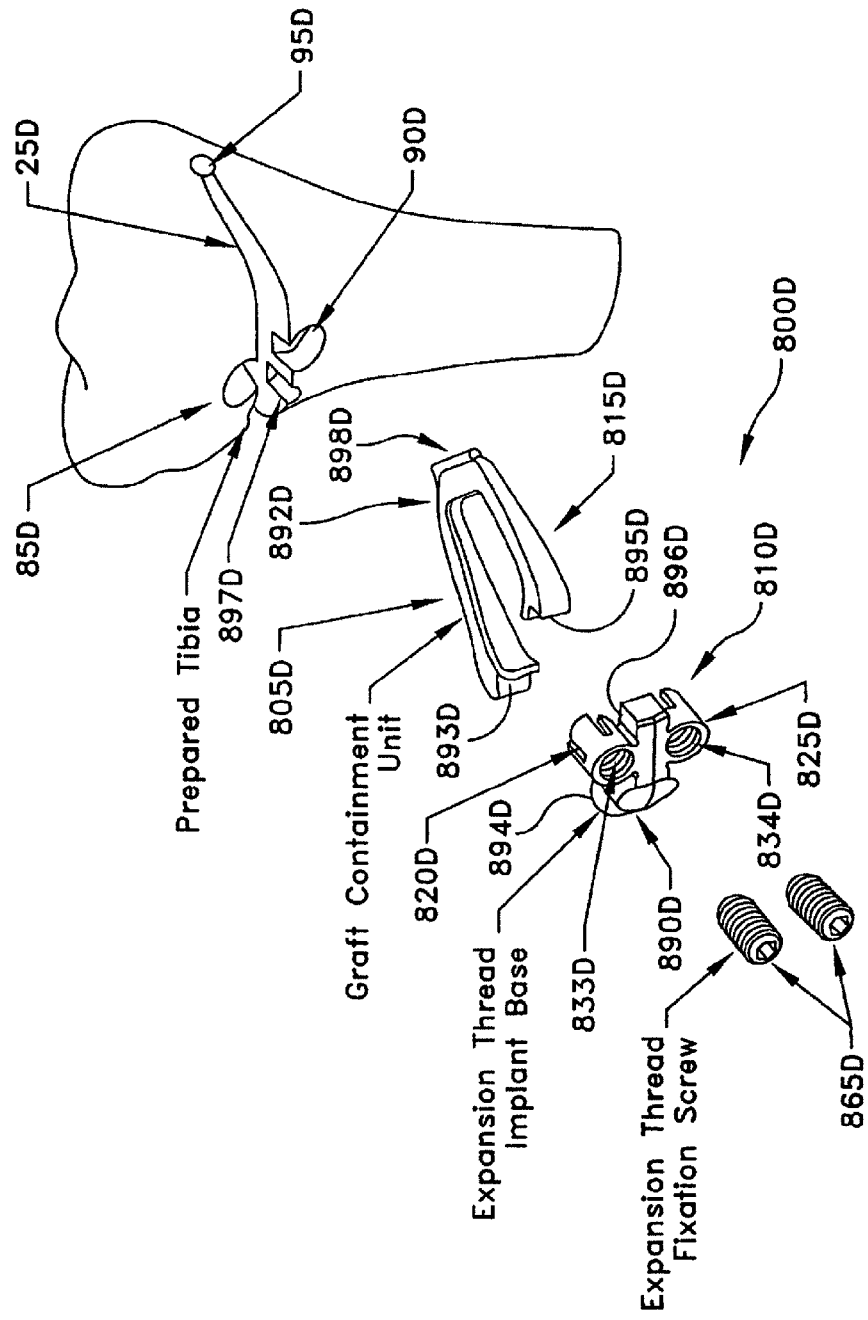
FIGS. 42-44 are schematic views showing yet another wedge-shaped implant formed in accordance with the present invention.
Figure 43:
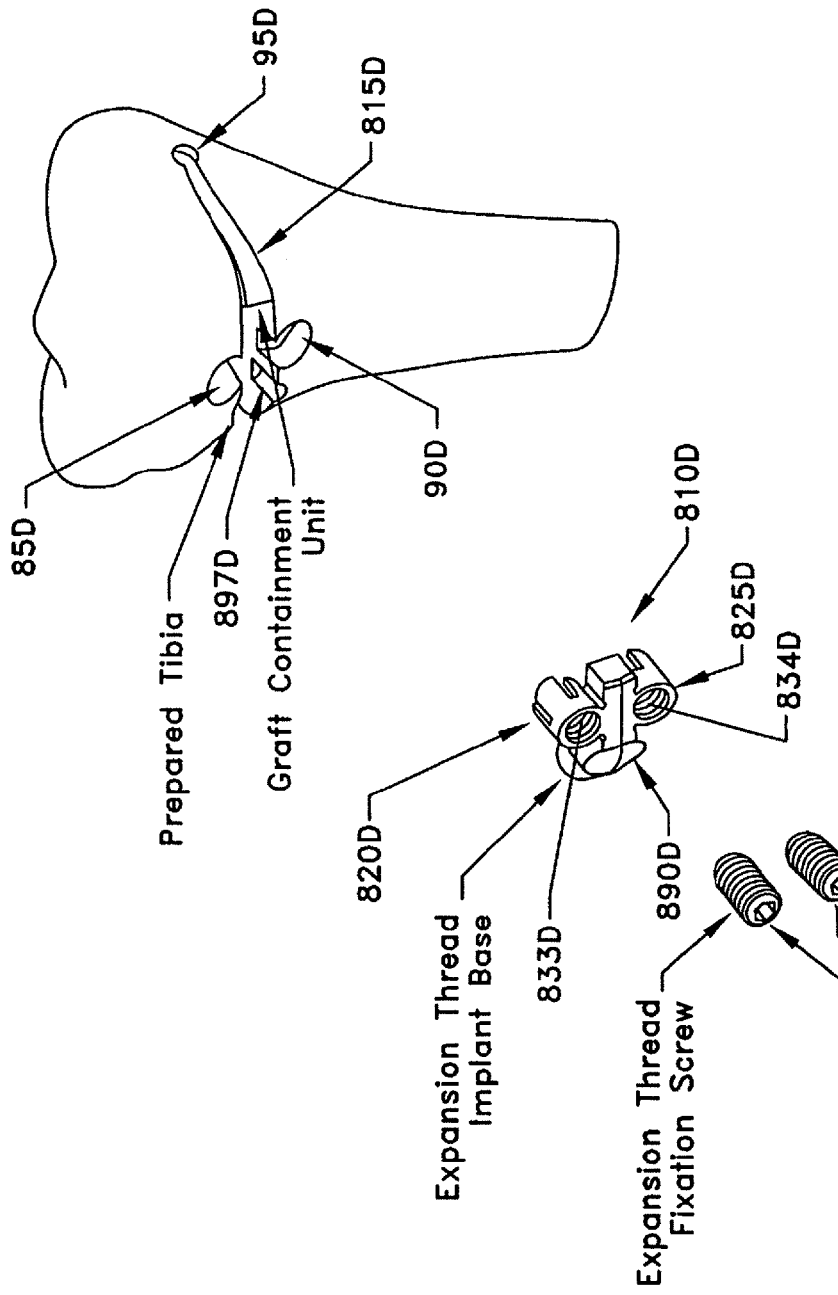
Figure 44:
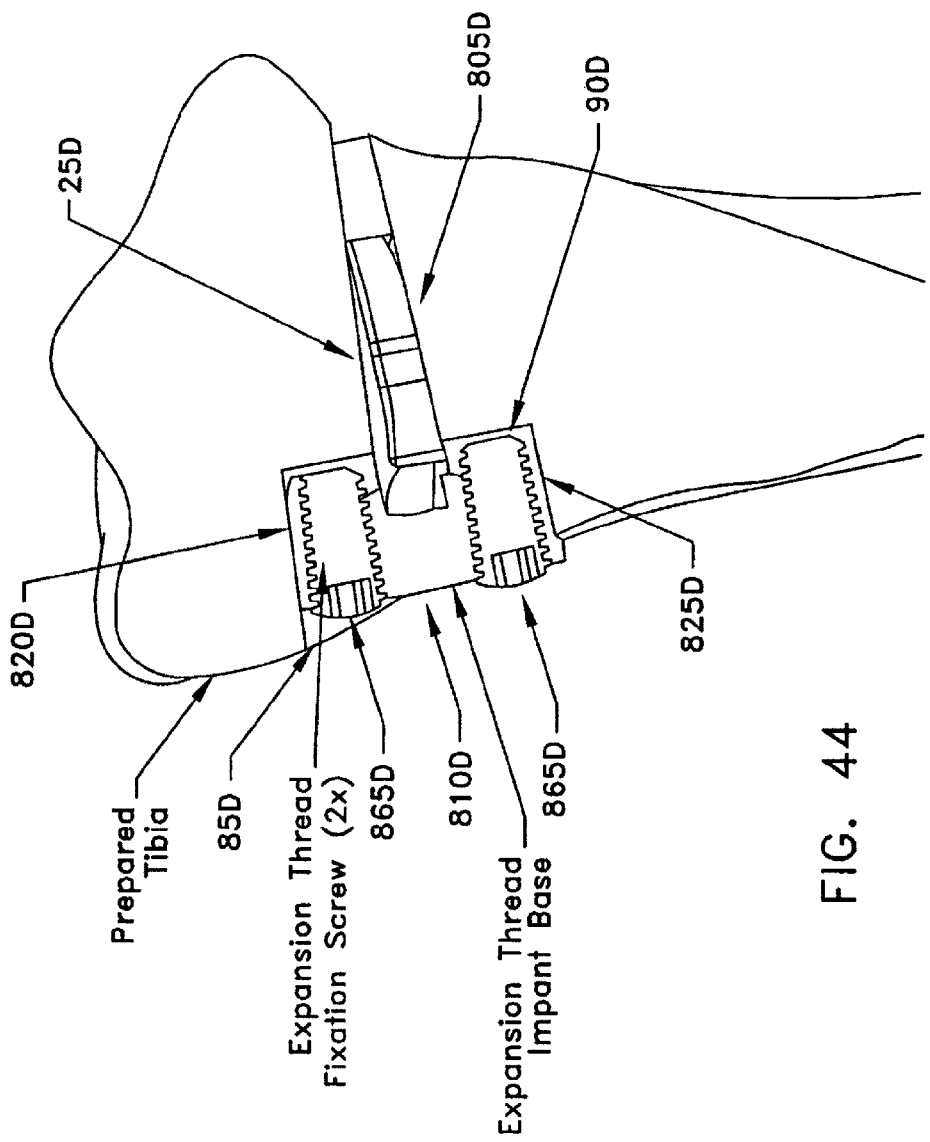

Looking next at FIGS. 42-44, there is shown an implant 800D also formed in accordance with the present invention. Implant 800D is generally similar to the implant 800C disclosed above, except that implant 800D is intended to be used with expansion thread fixation screws that terminate within the keys.

More particularly, and still looking now at FIGS. 42-44, implant 800D comprises a posterior graft containment arm (GCA) 805D, a base 810D and an anterior graft containment arm (GCA) 815D. Preferably a bridge 892D connects the distal end of posterior graft containment arm (GCA) 805D with the distal end of anterior graft containment arm (GCA) 815D. If desired, bridge 892D may be provided with a distal tab 898D to be received in oversized hole 95D. Distal tab 898D serves to improve the alignment and stability of implant 800D when seated in wedge-like opening 25D.

A shear rib 890D is formed in base 810D, laterally displaced from the two keys 820D, 825D (which are themselves arranged in an "over-under" configuration). Posterior graft containment arm (GCA) 805D includes a recess 893D, and base 810D includes a shoulder 894D, whereby posterior graft containment arm (GCA) 805D can mate with base 810D. Anterior graft containment arm (GCA) 815D includes a recess 895D, and implant base 810D includes a shoulder 896D, whereby anterior graft containment arm (GCA) 815D can mate with base 810D.

Posterior graft containment arm (GCA) 805D, and/or anterior graft containment arm (GCA) 815D, may include raised points or dimples 831D (not shown).

Keys 820D, 825D each include a bore 833D, 834D, respectively. Bores 833D, 834D receive expansion thread fixation screws 865D for fixing implant 800D to the tibia. Expansion thread fixation screws 865D are configured so as to intentionally terminate within bores 833D, 834D. This is in contrast to implant 800C which allows expansion thread fixation screws 865 to extend out of the distal ends of bores 833C, 834C and then into the adjacent bone. The bores 833D, 834D may be axially aligned with the longitudinal axes of keys 820D, 825D, respectively. Keys 820D, 825D may also include external ribs 836D (not shown). External ribs 836D may extend longitudinally or circumferentially. Keys 820D, 825D may also be slotted (i.e., in a manner analogous to the slots provided in keys 820, 825 of implant 800), whereby to permit keys 820D, 825D to expand when expansion thread fixation screws 865D are received in bores 833D, 834D. The external thread on the expansion thread fixation screws 865D may be tapered so as to expand the bore into the cancellous bone of the tibia when the expansion thread fixation screws are received within bores 833D, 834D. Alternatively, the internal thread on bores 833D, 834D may be tapered so as to expand the bore into the cancellous bone of the tibia when the expansion thread fixation screws 865D are received within bores 833D, 834D.

Shear rib 890D is laterally offset from keys 820D, 825D, which are arranged in an "over-under" configuration. Shear rib 890D projects above and below the top and bottom surfaces of base 810D. Among other things, it has been found that the provision of shear rib 890D provides, at the base of the implant, excellent load-bearing characteristics and substantial resistance to rotational and shear forces.

In order to provide appropriate keyholes 85D, 90D (FIG. 42) for receiving keys 820D, 825D, and also for providing a shear rib keyhole 897D for receiving shear rib 890D, a keyhole drill guide is used as disclosed above.

Implant 800D (and an associated drill guide) may be used in an open wedge, high tibial osteotomy in a manner which is generally similar to that previously described with respect to implant 800C (and drill guide 400C), except that expansion thread fixation screws 865D terminate within bores 833D, 834D.

Providing implant 800D with two graft containment arms, e.g., posterior graft containment arm (GCA) 805D and anterior graft containment arm (GCA) 815D, is frequently preferred. However, in some circumstances, it may be desirable to omit one or both of posterior graft containment arm (GCA) 805D and anterior graft containment arm (GCA) 815D. Thus, in one preferred form of the invention, implant 800D comprises only base 810D and omits both posterior graft containment arm (GCA) 805D and anterior graft containment arm (GCA) 815D.

Providing implant 800D with a pair of keys 820D, 825D is generally preferred. However, in some circumstances, it may be desirable to omit one or the other, or both, of keys 820D, 825D. Furthermore, in other circumstances, it may be desirable to provide more than two keys, e.g., to provide three keys.

Furthermore, each of the keys 820D, 825D may include more than one bore 833D, 834D. Thus, for example, one key may be expanded by multiple expansion thread fixation screws 865D.

It should be noted that while the construction of implant 800D is highly similar to the construction of implant 800C, the construction of implant 800D provides expansion thread fixation screws 865D that intentionally terminate within bores 833D, 834D, and hence within the body of the key, i.e., they do not penetrate into the adjacent bone.

Implant with Draw Nuts

Figure 45:
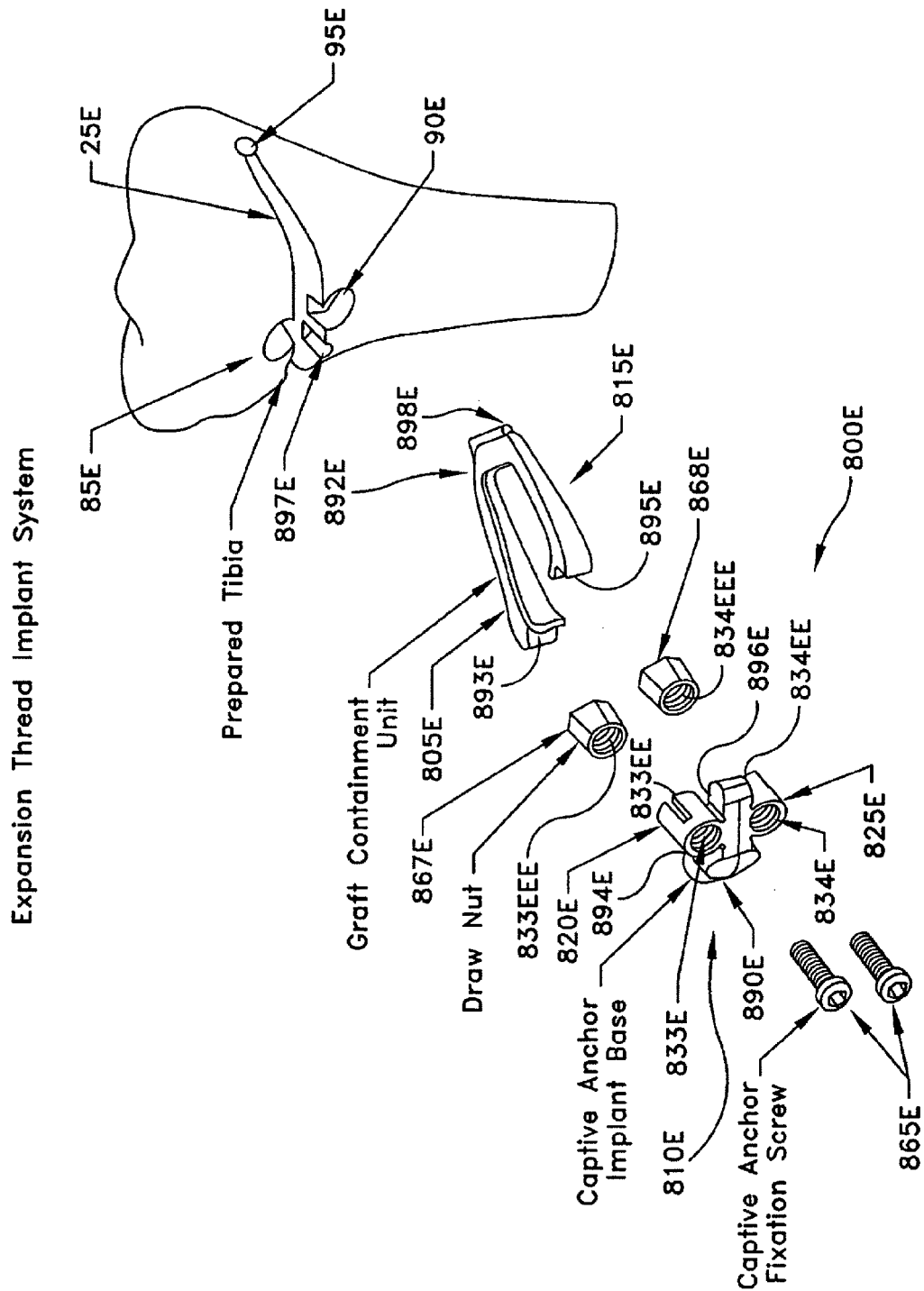
FIGS. 45-47 are schematic views showing another wedge-shaped implant formed in accordance with the present invention.
Figure 46:
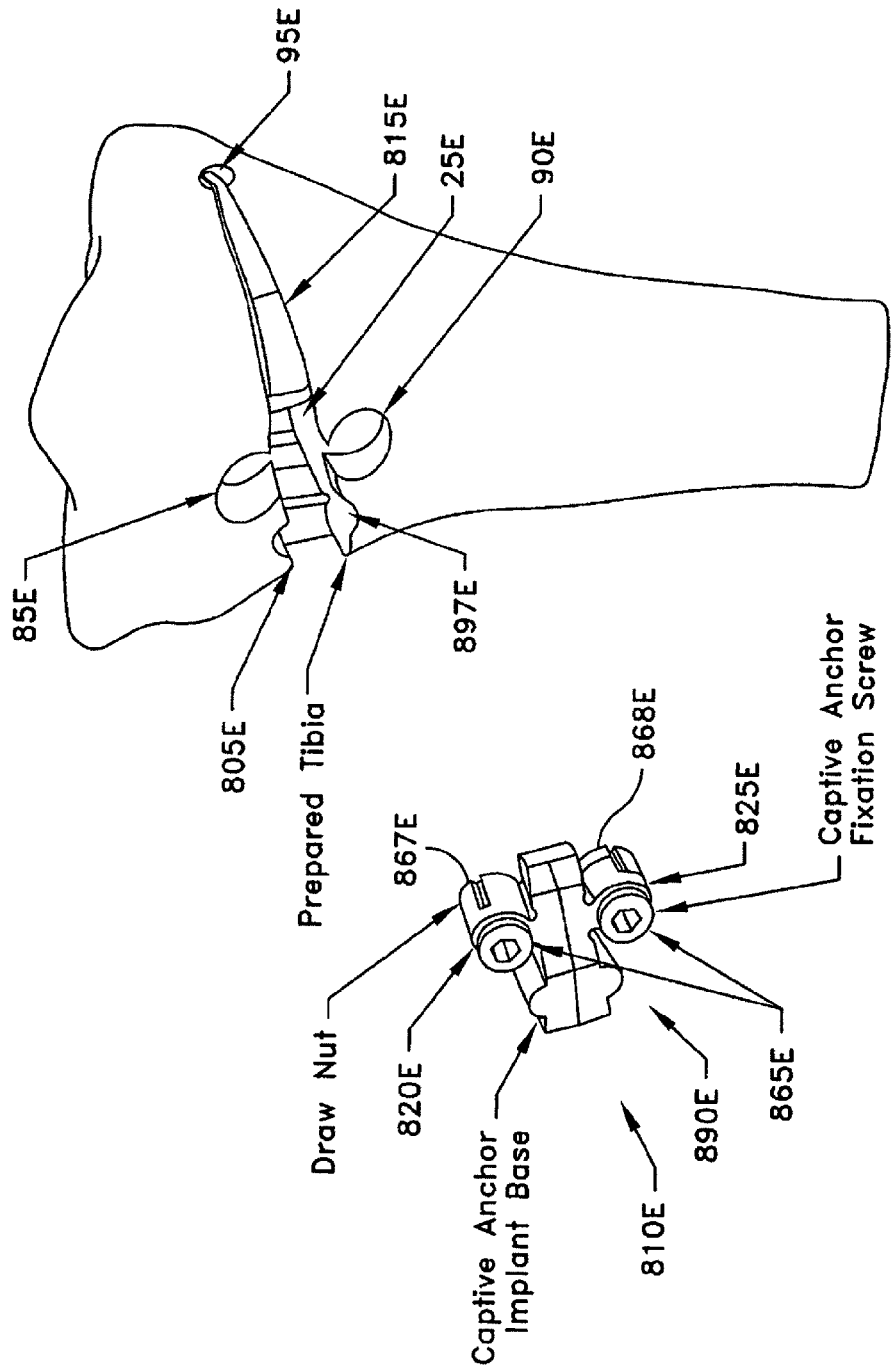
Figure 47:
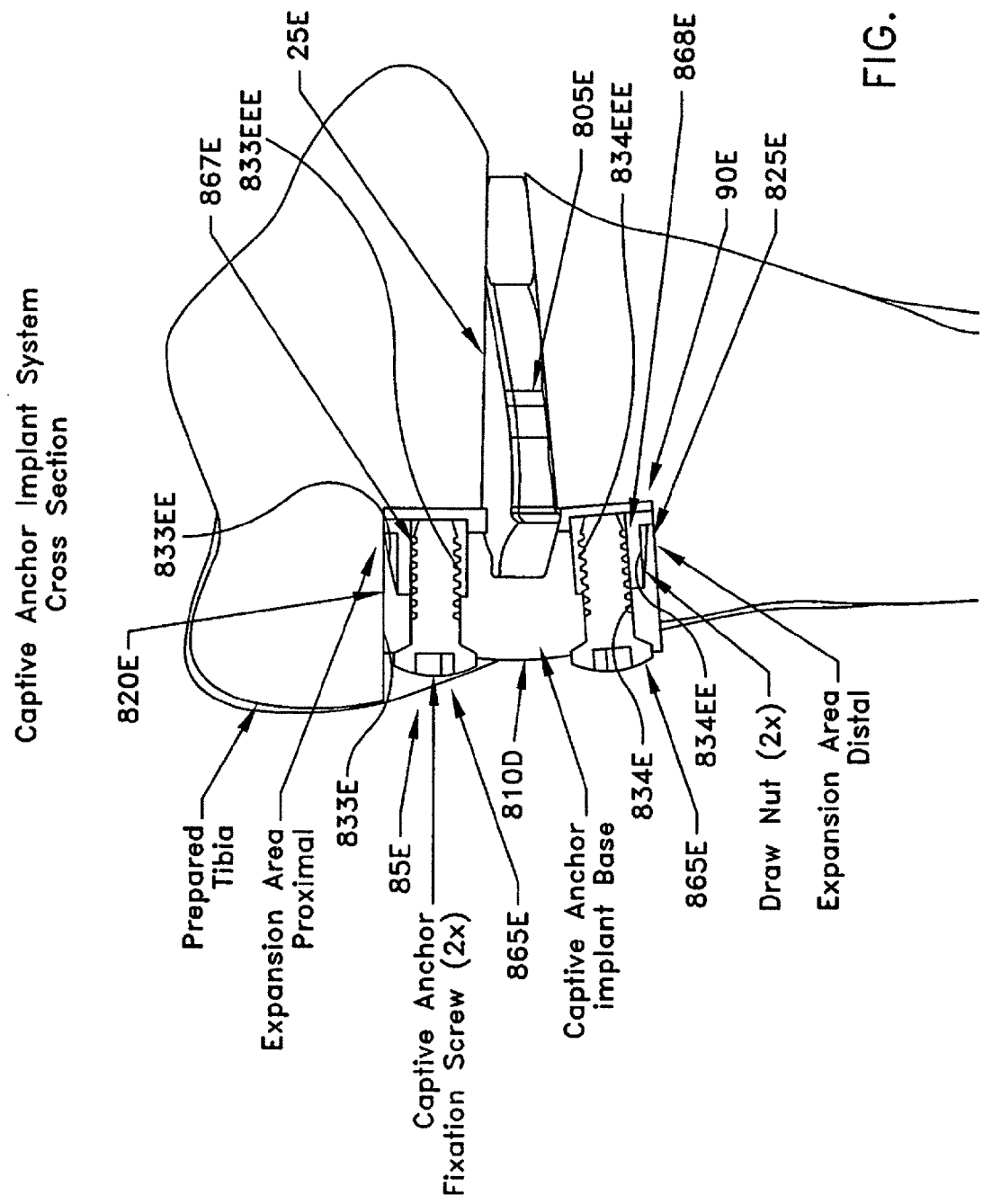

Looking next at FIGS. 45-47, there is shown an implant 800E also formed in accordance with the present invention. Implant 800E is generally similar to the implant 800C disclosed above, except that implant 800E provides counterbores 833EE, 834EE, respectively, for receiving draw nuts 867E, 868E, which in turn include bores 833EEE, 834EEE, respectively.

More particularly, and still looking now at FIGS. 45-47, implant 800E comprises a posterior graft containment arm (GCA) 805E, a base 810E and an anterior graft containment arm (GCA) 815E. Preferably a bridge 892E connects the distal end of posterior graft containment arm (GCA) 805E with the distal end of anterior graft containment arm (GCA) 815E. If desired, bridge 892E may be provided with a distal tab 898E to be received in oversized hole 95E. Distal tab 898E serves to improve the alignment and stability of implant 800E when seated in wedge-like opening 25E.

A shear rib 890E is formed in base 810E, laterally displaced from the two keys 820E, 825E (which are themselves arranged in an "over-under" configuration). Posterior graft containment arm (GCA) 805E includes a recess 893E, and base 810E includes a shoulder 894E, whereby posterior graft containment arm (GCA) 805E can mate with base 810E. Anterior graft containment arm (GCA) 815E includes a recess 895E, and implant base 810E includes a shoulder 896E, whereby anterior graft containment arm (GCA) 815E can mate with base 810E.

Posterior graft containment arm (GCA) 805E, and/or anterior graft containment arm (GCA) 815E, may include raised points or dimples 831E (not shown).

Keys 820E, 825E each include a bore 833E, 834E, respectively, and a counterbore 833EE, 834EE, respectively. Draw nuts 867E, 868E are positioned at the distal ends of bores 833E, 834E, in counterbores 833EE, 834EE, respectively. Draw nuts 867E, 868E each include a bore 833EEE, 834EEE, respectively, such that when expansion thread fixation screws 865E are received in bores 833E, 834E and bores 833EEE, 834EEE of draw nuts 867E, 868E, the draw nuts will be drawn into counterbores 833EE, 834EE, thereby enhancing the expansion of keys 820E, 825E, whereby to securely fix implant 800E to the tibia.

The bores 833E, 834E may be axially aligned with the longitudinal axes of keys 820E, 825E, respectively. Keys 820E, 825E may also include external ribs 836E (not shown). External ribs 836E may extend longitudinally or circumferentially. Keys 820E, 825E may also be slotted (i.e., in a manner analogous to the slots provided in keys 820, 825 of implant 800), whereby to permit keys 820E, 825E to expand when expansion thread fixation screws 865E are received in bores 833E, 834E and in bores 833EEE, 834EEE of draw nuts 867E, 868E.

Shear rib 890E is laterally offset from keys 820E, 825E, which are arranged in an "over-under" configuration. Shear rib 890E projects above and below the top and bottom surfaces of base 810E. Among other things, it has been found that the provision of shear rib 890E provides, at the base of the implant, excellent load-bearing characteristics and substantial resistance to rotational and shear forces.

In order to provide appropriate keyholes 85E, 90E (FIGS. 45 and 46) for receiving keys 820E, 825E, and also for providing a shear rib keyhole 897E for receiving shear rib 890E, a keyhole drill guide is used as disclosed above.

Implant 800E (and an associated drill guide) may be used in an open wedge, high tibial osteotomy in a manner which is generally similar to that previously described with respect to implant 800C (and drill guide 400C). Providing implant 800E with two graft containment arms, e.g., posterior graft containment arm (GCA) 805E and anterior graft containment arm (GCA) 815E, is frequently preferred. However, in some circumstances, it may be desirable to omit one or both of posterior graft containment arm (GCA) 805E and anterior graft containment arm (GCA) 815E. Thus, in one preferred form of the invention, implant 800E comprises only base 810E and omits both posterior graft containment arm (GCA) 805E and anterior graft containment arm (GCA) 815E.

Providing implant 800E with a pair of keys 820E, 825E is generally preferred. However, in some circumstances, it may be desirable to omit one or the other, or both, of keys 820E, 825E. Furthermore, in other circumstances, it may be desirable to provide more than two keys, e.g., to provide three keys.

Furthermore, each of the keys 820E, 825E may include more than one bore 833E, 834E and counterbore 833EE, 834EE and more than one draw nut 867E, 868E. Thus, for example, one key may be expanded by multiple expansion thread fixation screws 865E.

It should be noted that while the construction of implant 800E is highly similar to the construction of implant 800C, the construction of implant 800E provides draw nuts 867E, 868E positioned at the distal ends of bores 833E, 834E, received within counterbores 833EE, 834EE, respectively.

Implant with Open Keys

Figure 48:
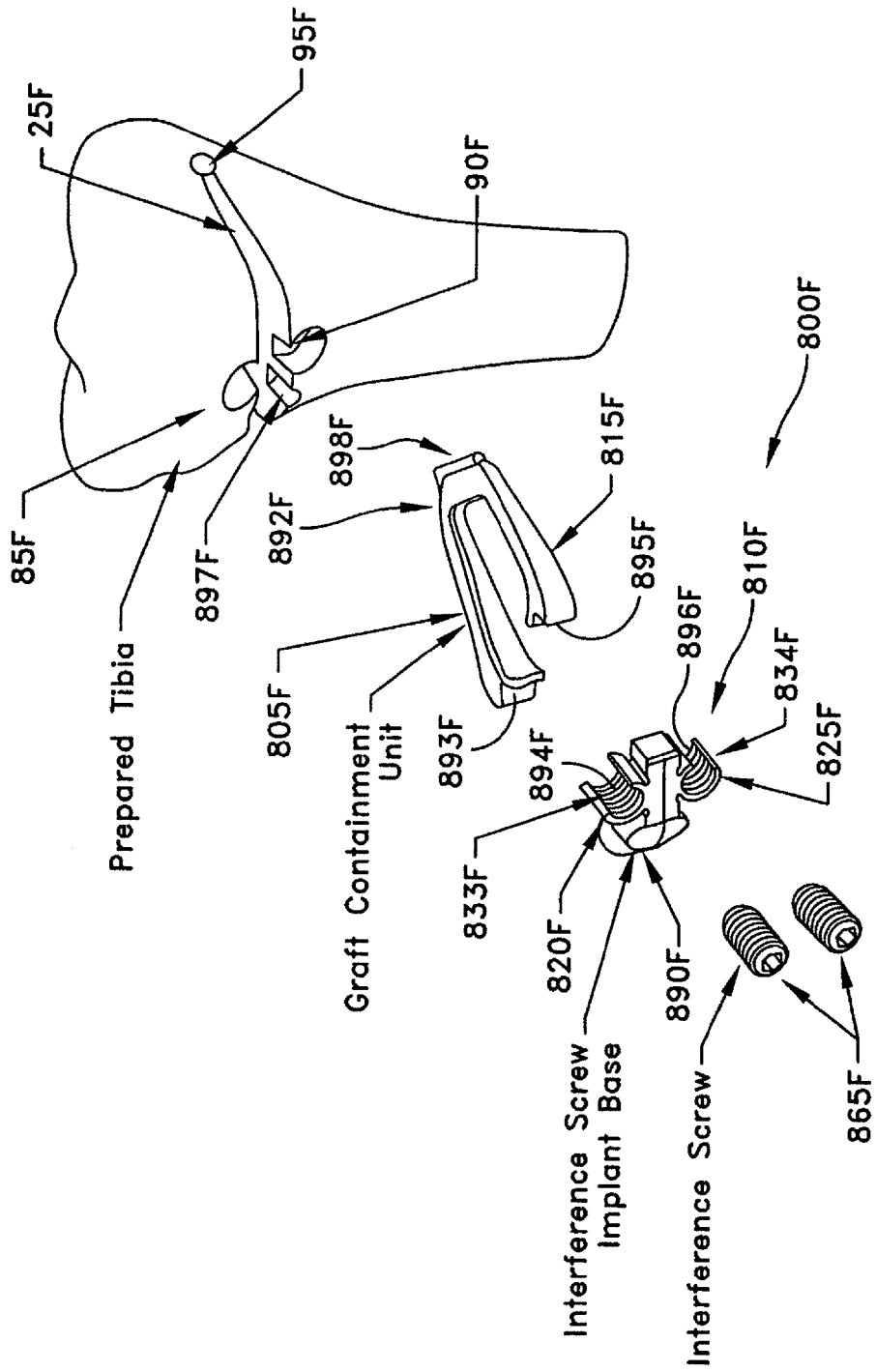
FIGS. 48-50 are schematic views showing still another wedge-shaped implant formed in accordance with the present invention.
Figure 49:
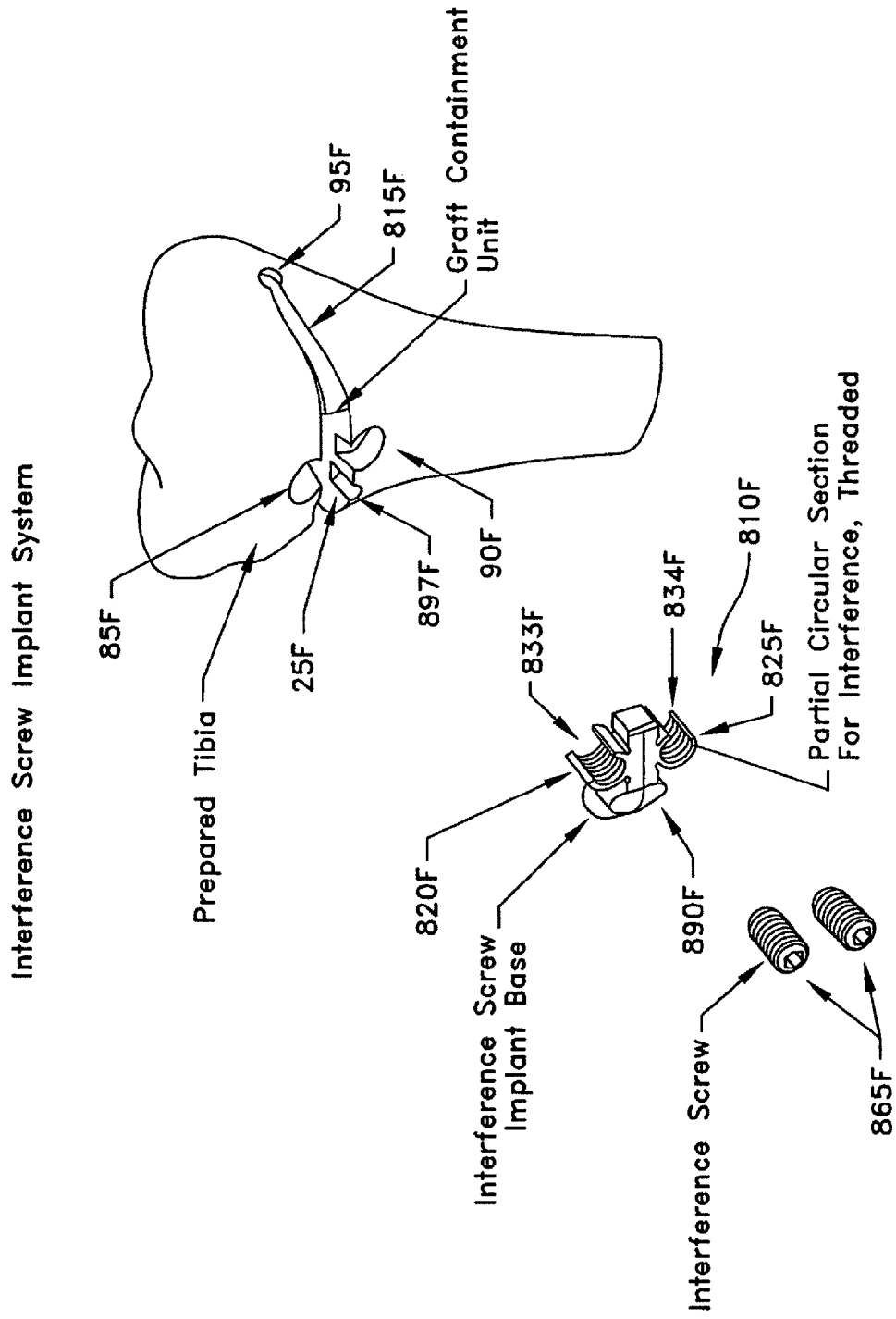
Figure 50:
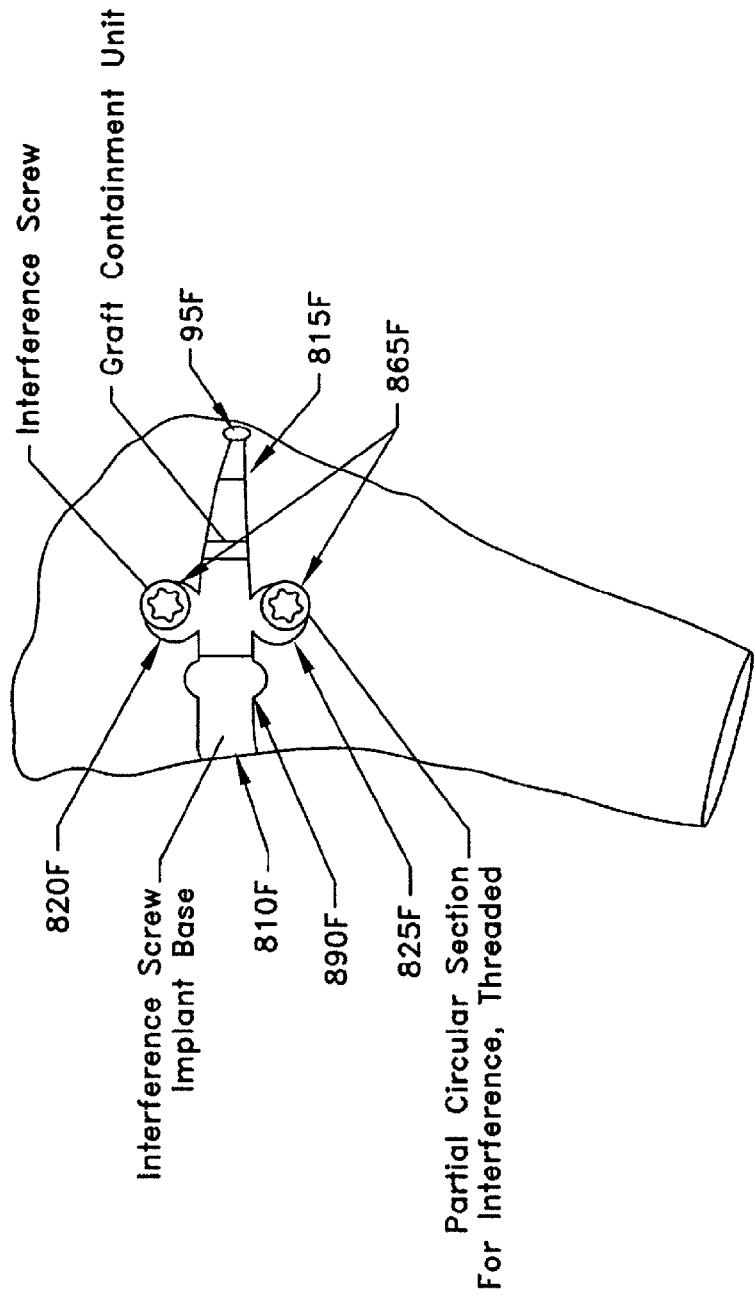

Looking next at FIGS. 48-50, there is shown an implant 800F also formed in accordance with the present invention. Implant 800F is generally similar to the implant 800C disclosed above, except that implant 800F provides open keys having opposed longitudinal edges. Furthermore, the open keys include threaded recesses.

More particularly, and still looking now at FIGS. 48-50, implant 800F comprises a posterior graft containment arm (GCA) 805F, a base 810F and an anterior graft containment arm (GCA) 815F. Preferably a bridge 892F connects the distal end of posterior graft containment arm (GCA) 805F with the distal end of anterior graft containment arm (GCA) 815F. If desired, bridge 892F may be provided with a distal tab 898F to be received in oversized hole 95F. Distal tab 898F serves to improve the alignment and stability of implant 800F when seated in wedge-like opening 25F.

A shear rib 890F is formed in base 810F, laterally displaced from two open keys 820F, 825F (which are themselves arranged in an "over-under" configuration). Posterior graft containment arm (GCA) 805F includes a recess 893F, and base 810F includes a shoulder 894F, whereby posterior graft containment arm (GCA) 805F can mate with base 810F. Anterior graft containment arm (GCA) 815F includes a recess 895F, and implant base 810F includes a shoulder 896F, whereby anterior graft containment arm (GCA) 815F can mate with base 810F.

Posterior graft containment arm (GCA) 805F, and/or anterior graft containment arm (GCA) 815F, may include raised points or dimples 831F (not shown).

Open keys 820F, 825F each include a threaded recess 833F, 834F, respectively. It should be appreciated that due to the geometry of the open keys 820F, 825F when expansion thread fixation screws 865F are received in the threaded recesses 833F, 834F, a portion of the threaded surface of expansion thread fixation screws 865F are exposed to, and hence directly engage, the adjacent bone. This is in contrast with implant 800C, wherein the fixation screws 865C are received within closed keys 820C, 825C.

In one form of the present invention, the keyholes 85F, 90F may be further prepared by tapping with a tap 899F (not shown) with a corresponding thread pitch to that of expansion thread fixation screws 865F.

Threaded recesses 833F, 834F may be axially aligned with the longitudinal axes of open keys 820F, 825F, respectively. Open keys 820F, 825F may also include external ribs 836F. External ribs 836F may extend longitudinally or circumferentially. Open keys 820F, 825F may also be only partially opened, i.e., along only a portion of the length of the keys (i.e., in a manner analogous to the slots provided in keys 820, 825 of implant 800), whereby to provide open keys 820F, 825F with greater structural integrity.

Shear rib 890F is laterally offset from open keys 820F, 825F, which are arranged in an "over-under" configuration. Shear rib 890F projects above and below the top and bottom surfaces of base 810F. Among other things, it has been found that the provision of shear rib 890F provides, at the base of the implant, excellent load-bearing characteristics and substantial resistance to rotational and shear forces.

In order to provide appropriate keyholes 85F, 90F (FIG. 48) for receiving open keys 820F, 825F, and also for providing a shear rib keyhole 897F for receiving shear rib 890F, a keyhole drill guide is used as disclosed above.

Implant 800F (and the associated drill guide) may be used in an open wedge, high tibial osteotomy in a manner which is generally similar to that previously described with respect to implant 800C (and drill guide 400C), except that the bridged graft containment unit, i.e., posterior graft containment arm (GCA) 805F, bridge 892F and anterior graft containment arm (GCA) 815F, is installed as a single construction. Furthermore, when drill guide 400F is used to form keyholes 85F and 90F, it is also used to form shear rib keyhole 897F.

Providing implant 800F with two graft containment arms, e.g., posterior graft containment arm (GCA) 805F and anterior graft containment arm (GCA) 815F, is frequently preferred. However, in some circumstances, it may be desirable to omit one or both of posterior graft containment arm (GCA) 805F and anterior graft containment arm (GCA) 815F. Thus, in one preferred form of the invention, implant 800F comprises only base 810F and omits both posterior graft containment arm (GCA) 805F and anterior graft containment arm (GCA) 815F.

Providing implant 800F with a pair of open keys 820F, 825F is generally preferred. However, in some circumstances, it may be desirable to omit one or the other, or both, of open keys 820F, 825F. Furthermore, in other circumstances, it may be desirable to provide more than two open keys, e.g., to provide three open keys.

Furthermore, each of the open keys 820F, 825F may include more than one threaded recess 833F, 834F. Thus, for example, open keys may contain multiple, but not overlapping, recesses to receive multiple expansion thread fixation screws 865F. Thus, for example, an open key may include two recesses, one angled leftwardly so as to direct a fixation screw leftwardly into the tibia to the left of the open key, and/or one angled rightwardly so as to direct a fixation screw rightwardly into the tibia to the right of the open key.

It should be noted that while the construction of implant 800F is highly similar to the construction of implant 800C, the construction of implant 800F provides keys which allow a portion of the threaded surface of expansion thread fixation screws 865F to directly engage the adjacent bone.

Keyhole Drill Guide Stabilizer

Figure 51:
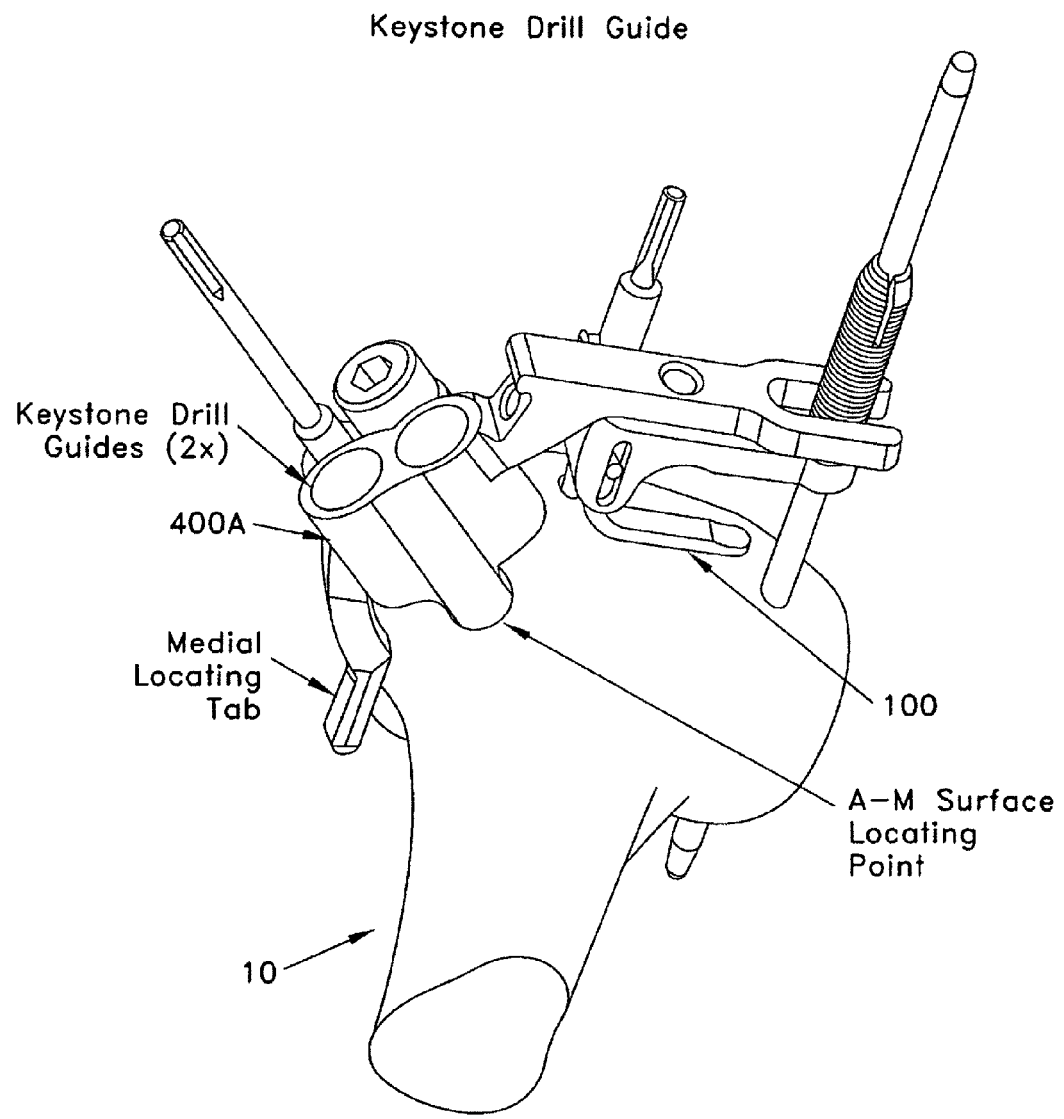
FIGS. 51-53 are schematic views showing a keyhole drill guide stabilizer provided in accordance with another preferred embodiment of the present invention.
Figure 52:
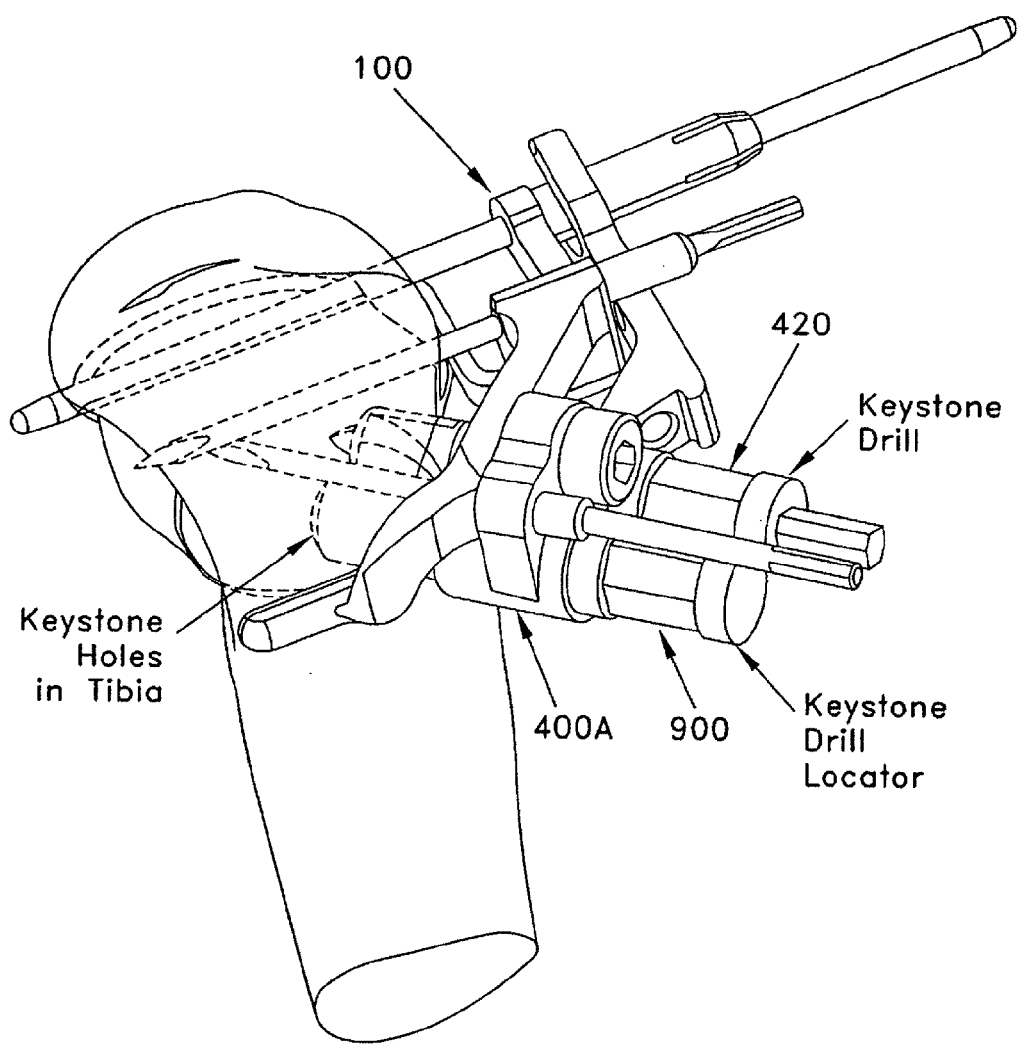
Figure 53:
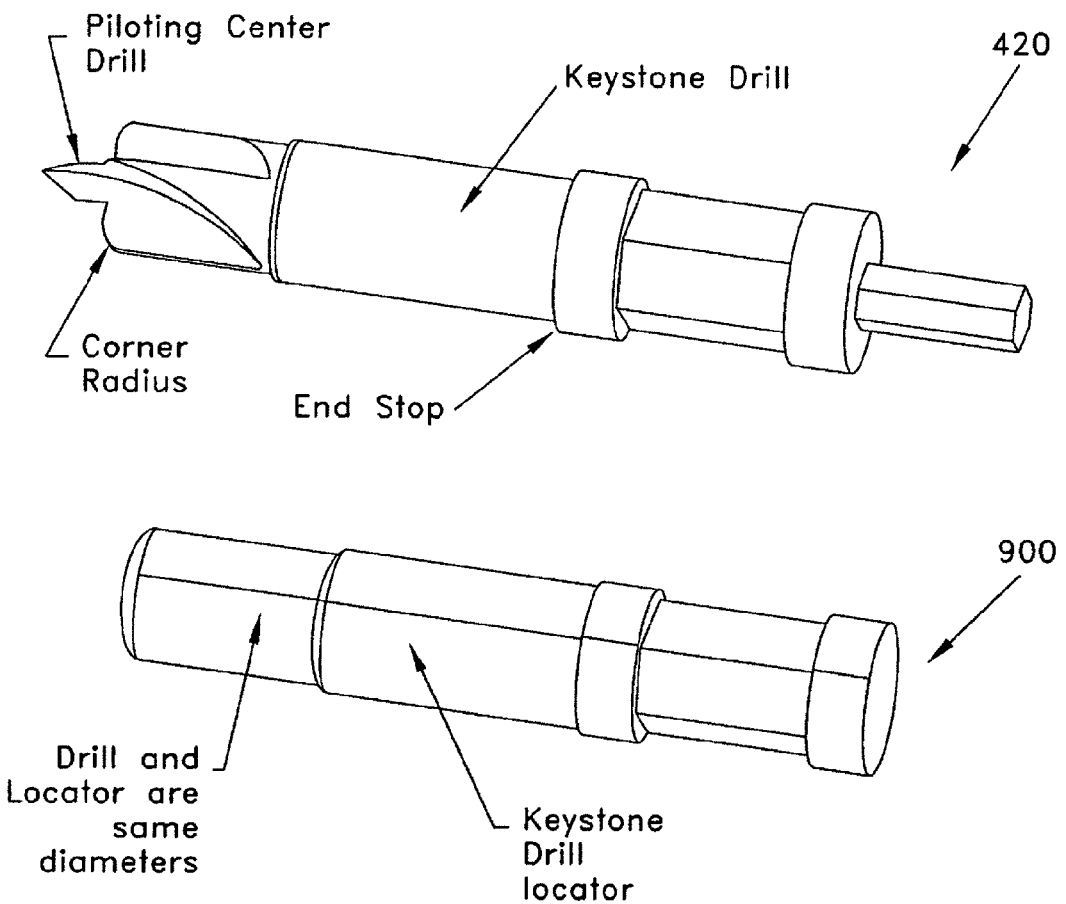
Figure 54:
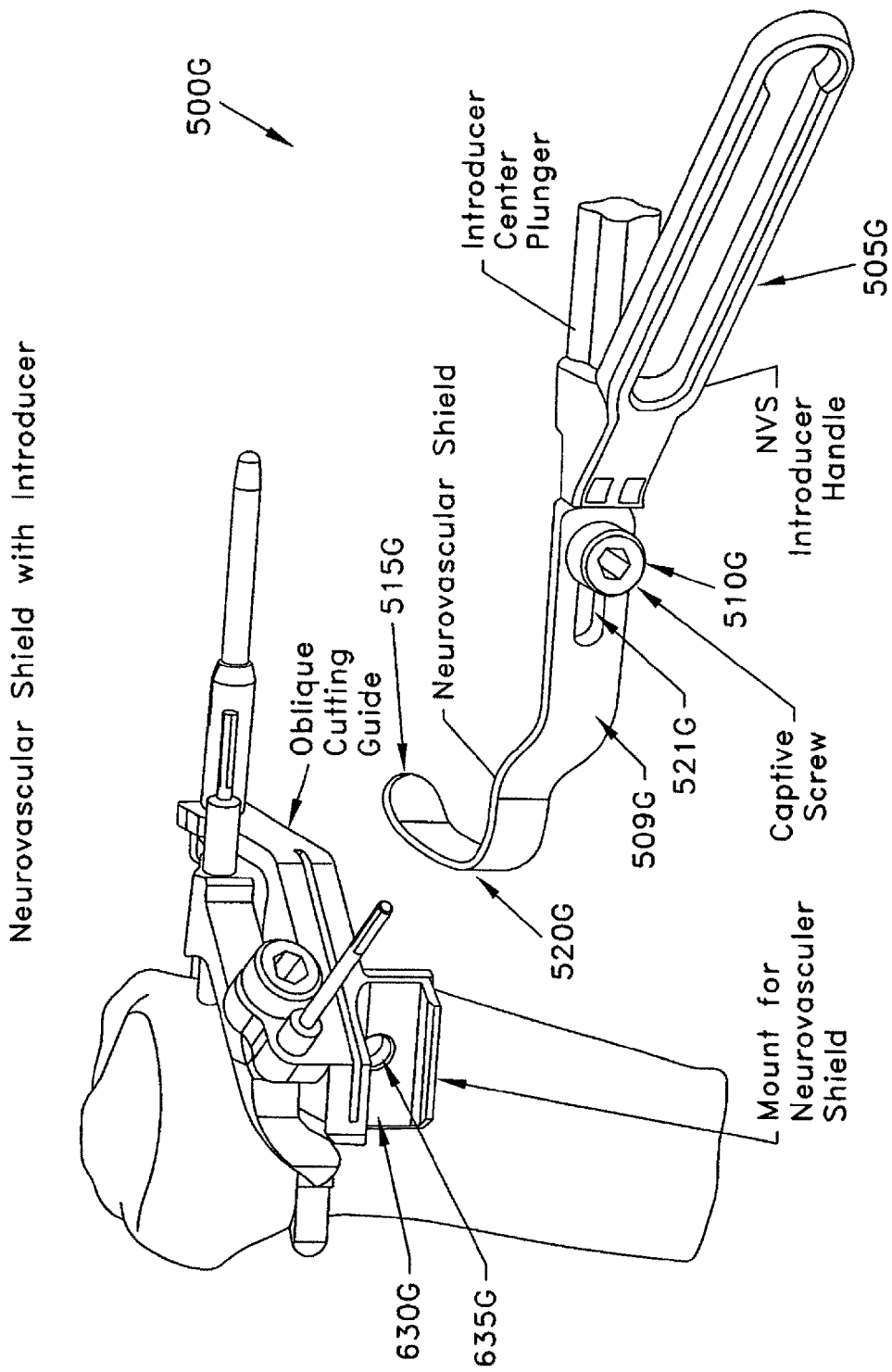
FIGS. 54-57 are schematic views showing an alternative posterior protector provided in accordance with another preferred embodiment of the present invention.
Figure 55:
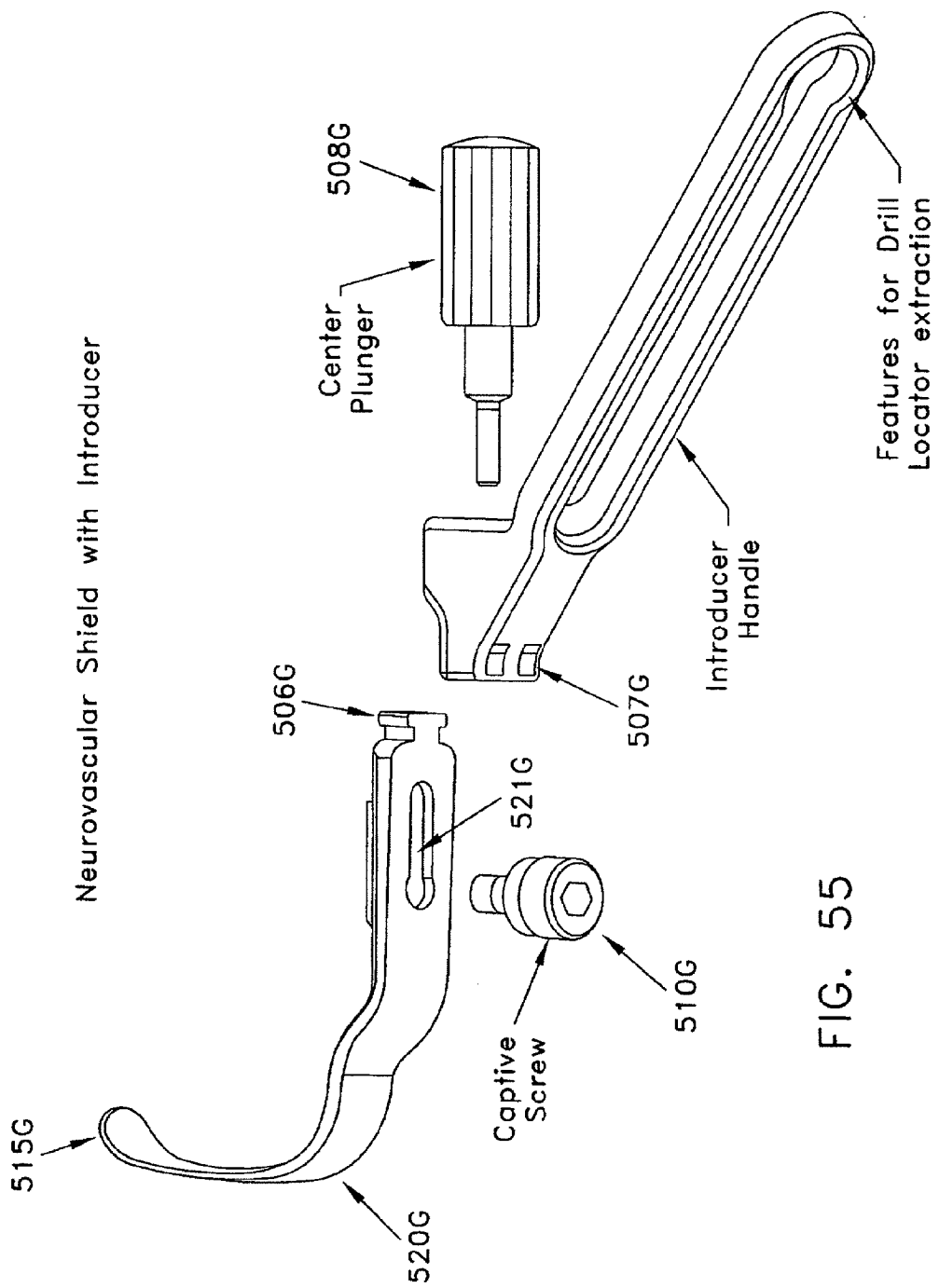
Figure 56:
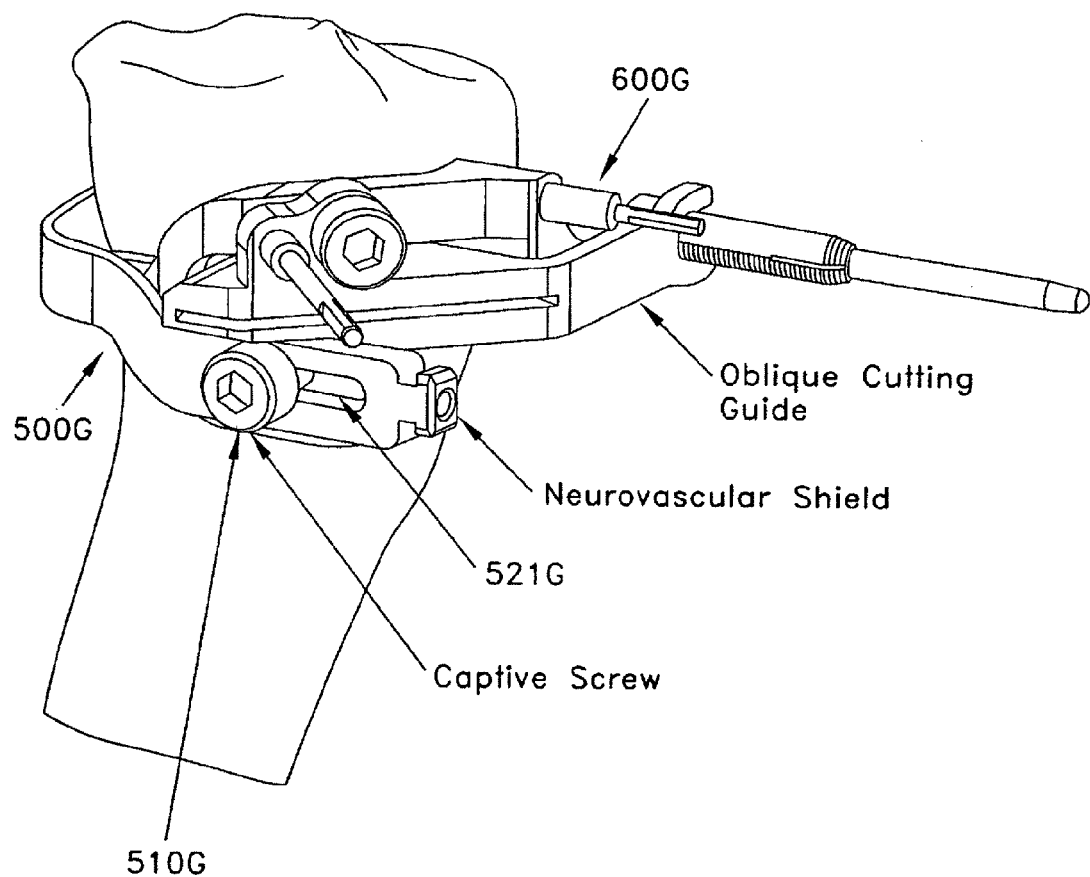
Figure 57:
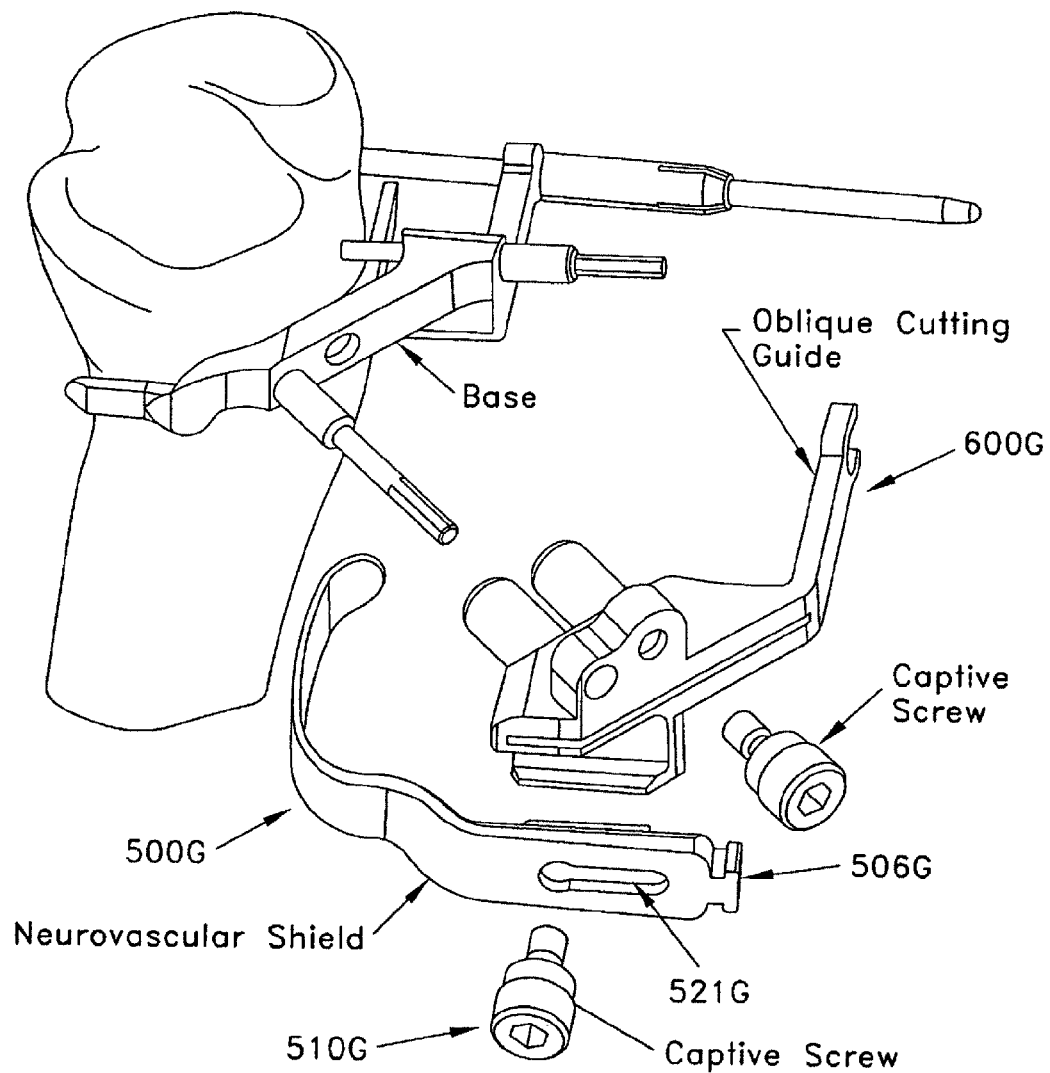

Looking next at FIGS. 51-53, there is shown a keyhole drill guide stabilizer 900. Keyhole drill guide stabilizer 900 is used to help further stabilize the drill guide after the first keyhole has been drilled in the tibia and before the second keyhole is drilled in the tibia. This is done by advancing keyhole drill guide stabilizer 900 through the drill guide and into the first-drilled keyhole, and then maintaining the keyhole drill guide stabilizer in that position while the second keyhole is drilled through the drill guide and into the tibia. This approach helps to eliminate the possibility of any positional variation between the two drilled keyholes due to inadvertent movement of the drill guide between drilling of the two keyholes.

Thus, for example, in FIG. 51 there is shown a drill guide 400A positioned against tibia 10. After the first keyhole has been drilled into the tibia, keyhole drill guide stabilizer 900 is advanced through the drill guide and into the first-drilled keyhole (FIG. 52). Then, with the keyhole drill guide stabilizer 900 in place, end mill 420 is used to drill the second keyhole. The provision of keyhole drill guide stabilizer 900 helps to eliminate the possibility of any positional variation between the two drilled keyholes due to inadvertent movement of the drill guide between drilling of the two keyholes.

It will be appreciated that keyhole drill guide stabilizer 900 may be used with drill guides which are configured to form "side-by-side" keyholes (e.g., such as the drill guide 400A shown in FIGS. 51 and 52) and/or "over-under" keyholes (such as the drill guide 400 shown in FIG. 18). Furthermore, keyhole drill guide stabilizer 900 may be used with drill guides which are configured to form a shear rib keyhole (e.g., such as the drill guide 400C shown in FIG. 39).

In addition, keyhole drill guide stabilizer 900 may be used with drill guides which are configured to form more than two keyholes. By way of example but not limitation, in the case where three keyholes are to be formed, keyhole drill guide stabilizer 900 is advanced through the drill guide and into the first-drilled keyhole, and then maintained in that position while the second keyhole is drilled through the drill guide and into the tibia. Subsequently, keyhole drill guide stabilizer 900 may be maintained in the first-drilled keyhole or the second-drilled keyhole while the third keyhole is drilled through the drill guide and into the tibia.

Alternative Posterior Protector

Looking next at FIGS. 54-57, there is shown an alternative posterior protector 500G. Posterior protector 500G is attached to an introducer 505G via a tongue 506G and groove 507G, and a center plunger 508G which secures tongue 506G in groove 507G. Posterior protector 500G preferably comprises an extension 509G, a far tip 515G and a curved portion 520G. Extension 509G is slidably received in a slot 630G formed in cutting guide 600G. A thumb screw 510G, extending through a slot 521G in extension 509G, is received in a hole 635G formed in drill guide 600G.

In use, posterior protector 500G is attached to introducer 505G via tongue 506G and groove 507G, and made fast in this position with center plunger 508G. Then the assembly is positioned around the tibia so as to sit between the tibia and the surrounding delicate neurovascular tissues. Then extension 509G is slidably received in slot 630G formed in cutting guide 600G and made fast with thumb screw 510G. It is important to note that by forming extension 509G so that it is slidably received in slot 630G, posterior protector is able to accommodate variations in tibial tubercle anatomy. Then center plunger 508G is removed, and finally introducer 505G is removed, leaving the apparatus in the position shown in FIG. 56, ready for the next step in the procedure.

In accordance with the present invention, far tip 515G may be formed so as to have a flexible or a fixed construction.

Also in accordance with the present invention, curved portion 520G may be constructed with a concave shape. The concave shape provides the surgeon with the assurance that the soft tissues located at the back of the knee are protected during the osteotomy.

Collet Nut for Clamping Apex Pin

Figure 58:
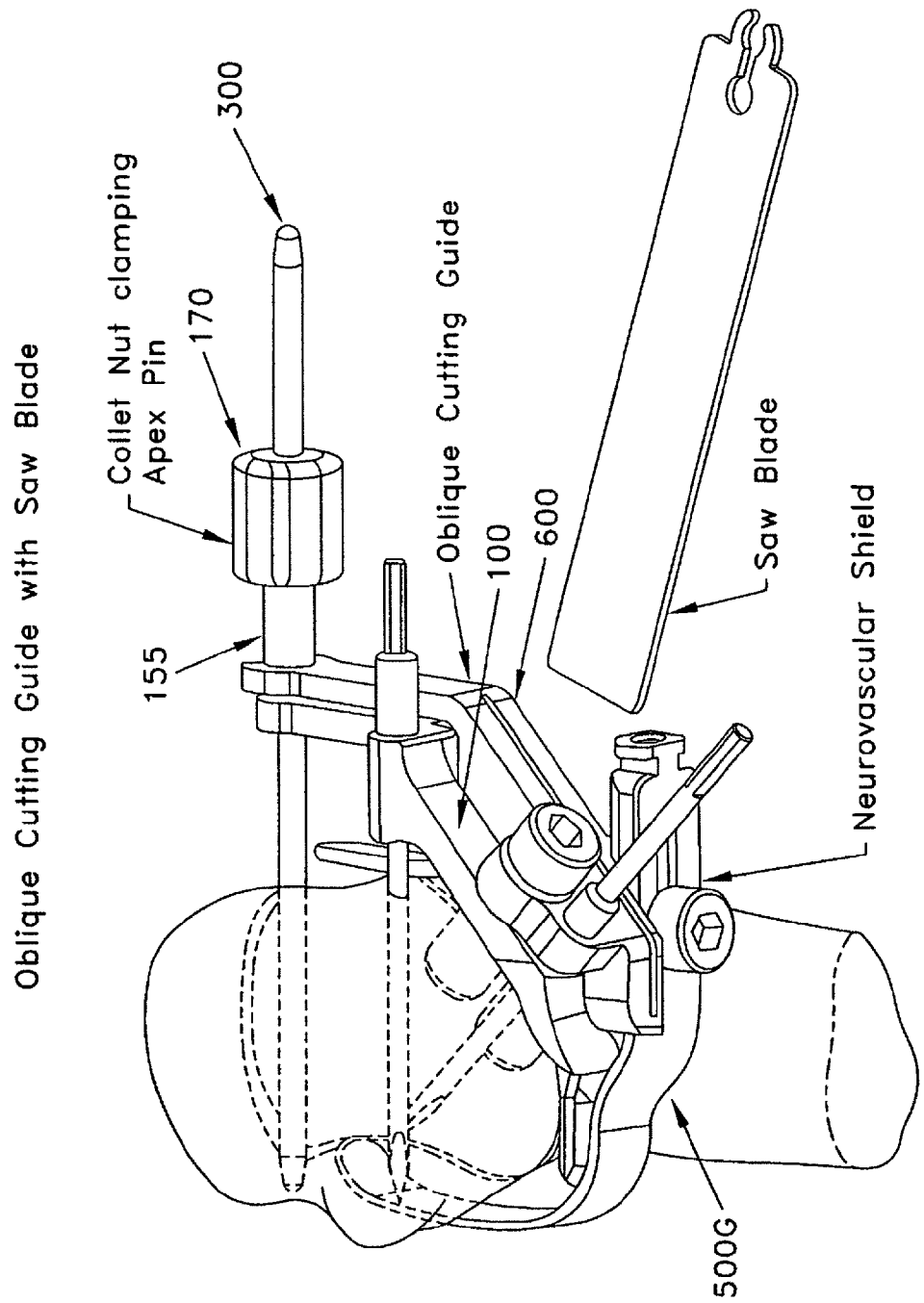
FIG. 58 is a schematic view showing a collet nut which may be used to secure the apex pin to the positioning guide in accordance with another preferred embodiment of the present invention.

In some circumstances it may be desirable to secure apex pin 300 to positioning guide 100 and, more particularly, to apex aimer 155. To this end, and looking now at FIG. 58, a collet nut 170 may be used to secure apex pin 300 to the apex aimer 155 of positioning guide 100. More particularly, in this form of the invention, the proximal end of apex aimer 155 may be configured so as to terminate in a plurality of flexible fingers, with the flexible fingers being arranged so as to together form the cylindrical structure of the apex aimer. Furthermore, the collective structure of the flexible fingers may be threaded, so as to receive the collet nut thereon. Accordingly, when the collet nut is screwed onto the proximal end of apex aimer 155, the fingers can be driven radially inwardly so as to grip the apex pin 300, whereby to secure the apex pin to the apex aimer.

Dogbone Spacer for Opening Jack

Figure 59:
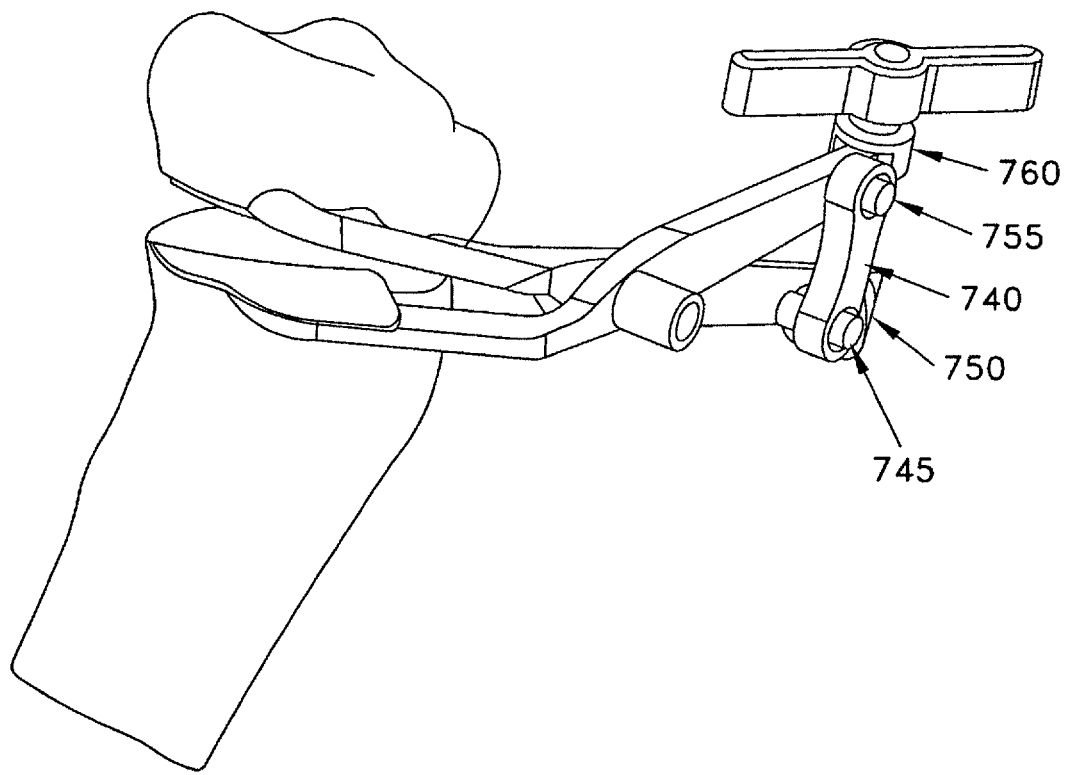
FIG. 59 is a schematic view showing a dogbone spacer which may be used in conjunction with an opening jack to confirm an appropriate correction angle before committing to that correction angle.

In some cases the surgeon may wish to, inter-operatively, confirm an appropriate correction angle before committing to that correction angle. To this end, and looking now at FIG. 59, there is shown a dogbone spacer 740 which mounts to (i) a pin 745 on one free leg 750 of the opening jack, and (ii) a pin 755 on the other free leg 760 of the opening jack. By providing a kit containing a wide range of dogbone spacer sizes, the surgeon (by selecting an appropriate dogbone spacer size and mounting it to the opening jack) can confirm a correction angle with certainty before committing to that correction angle (i.e., by opening a sterile pack containing an implant of a specific size and geometry).

Keyhole Spacer

Figure 60:
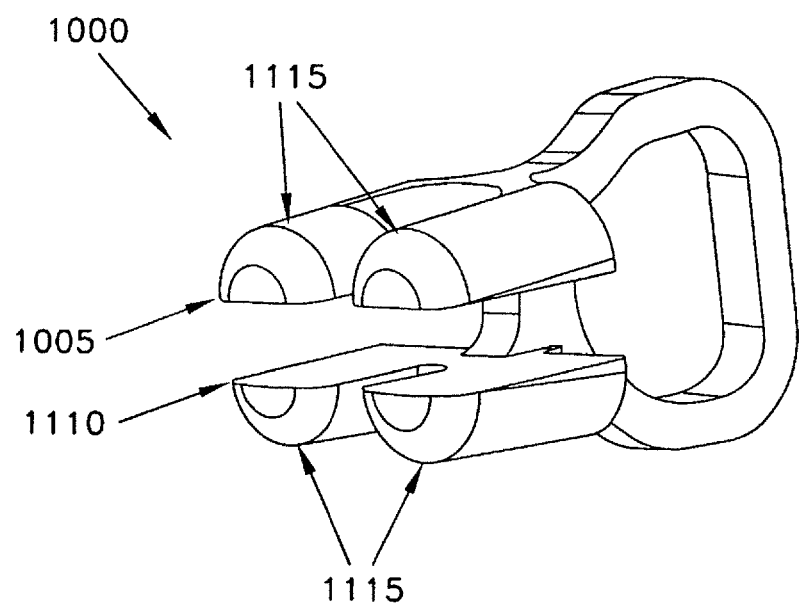
FIG. 60 is a schematic view of a keyhole spacer which may also be used to verify an appropriate correction angle before committing to that correction angle.

Looking next at FIG. 60, there is shown a keyhole spacer 1000 which may also be used to verify an appropriate correction angle before committing to that correction angle. More particularly, keyhole spacer 1000 comprises two keyhole mounts 1005, 1010, wherein each keyhole mount comprises first and second portions 1115 which seat, in spaced-apart fashion, in a keyhole on opposite sides of the wedge-like opening 25. By appropriately sizing each of the keyhole mounts, the surgeon can confirm a correction angle with certainty before committing to that correction angle (i.e., by opening a sterile pack containing an implant of a specific size and geometry).

Significantly, by forming keyhole spacer 1000 out of a radiotranslucent material, keyhole spacer 1000 can be used with fluoroscopic imaging without interfering with visualization.

It should be appreciated that that keyhole spacer 1000 may be configured for use with both "side-by-side" keyholes and/or for "over-under" keyholes.

Wedge Implant with "Toe" Screw(s)

Figure 61:
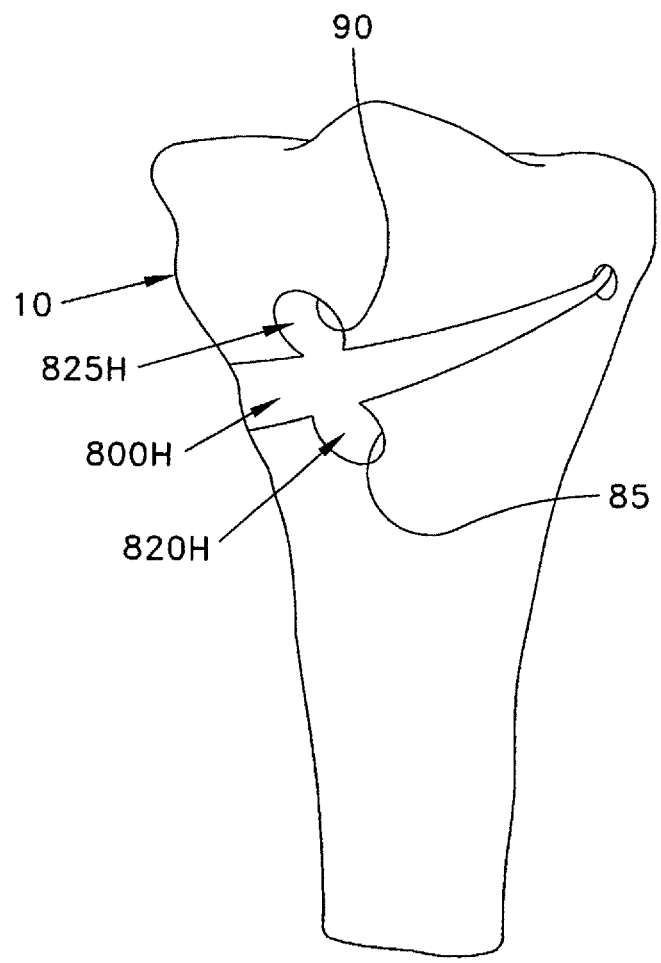
FIGS. 61-63 are schematic side views showing another novel implant disposed in the tibia.

Looking next at FIG. 61, there is shown another wedge implant 800H also formed in accordance with the present invention. Wedge implant 800H is substantially the same as the implant 800 previously described, except that (i) implant 800H is preferably formed as a one-piece construction, and (ii) keys 820H, 825H preferably omit the screw bores 833, 834 associated with the keys 820, 825 of implant 800.

Figure 62:
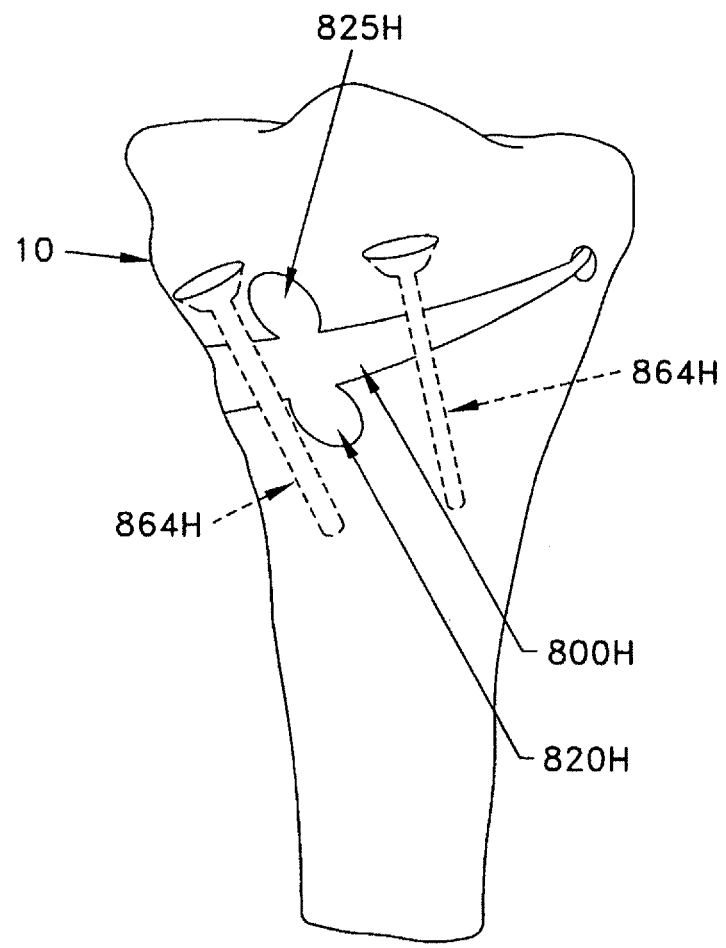
Figure 63:
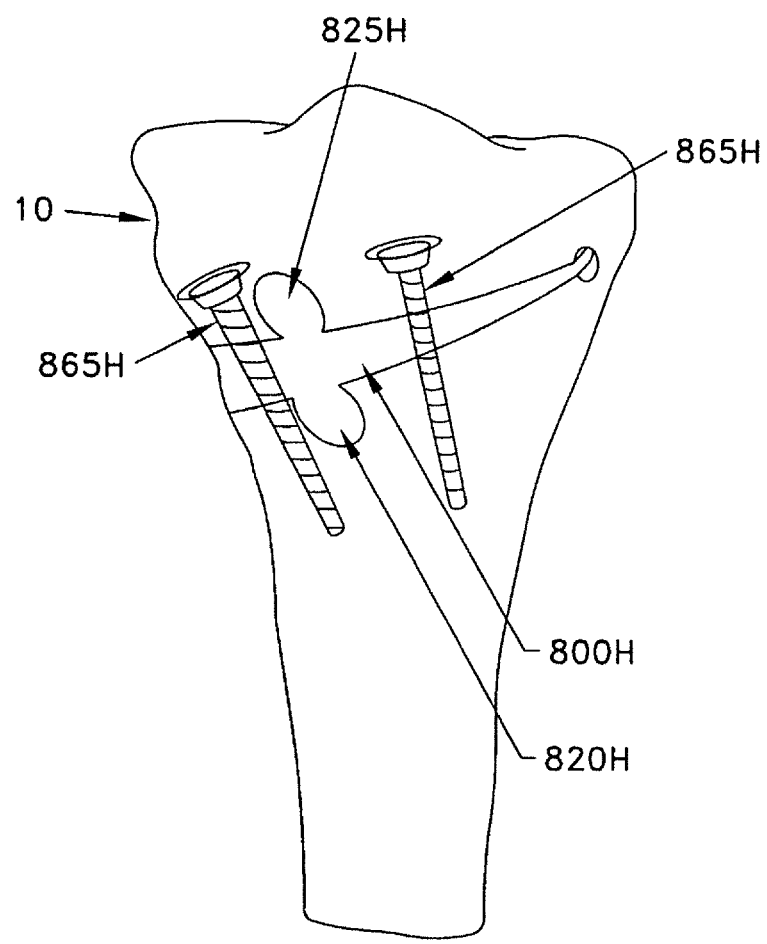

Wedge implant 800H is used by first preparing the tibia in the usual fashion (i.e., by forming the keyholes 85, 90 in the tibia, forming the osteotomy cut 20 in the tibia, and opening the tibia so as to form the wedge-like opening 25). Next, wedge implant 800H is inserted in the wedge-like opening, with keys 820H, 825H disposed in keyholes 85, 90, respectively (FIG. 61). Then one or more fixation holes 864H (FIG. 62) are drilled into the tibia, through the implant 800H, and into the tibia on the far side of the implant. Then one or more fixation screws 865H (FIG. 63) are inserted into fixation holes 864H so that they pass through the tibia, through the implant 800H and into the tibia on the far side of the implant. Thus it will be seen that fixation screws 865H essentially serve as "toe" screws to secure wedge implant 800H in the tibia. In this respect it should be appreciated that fixation holes 864H and fixations screw 865H may pass through any portion of implant 800H, including keys 820H, 825H.

"Toe" screws can be also be used to secure wedge implants having other configurations.

Figure 64:
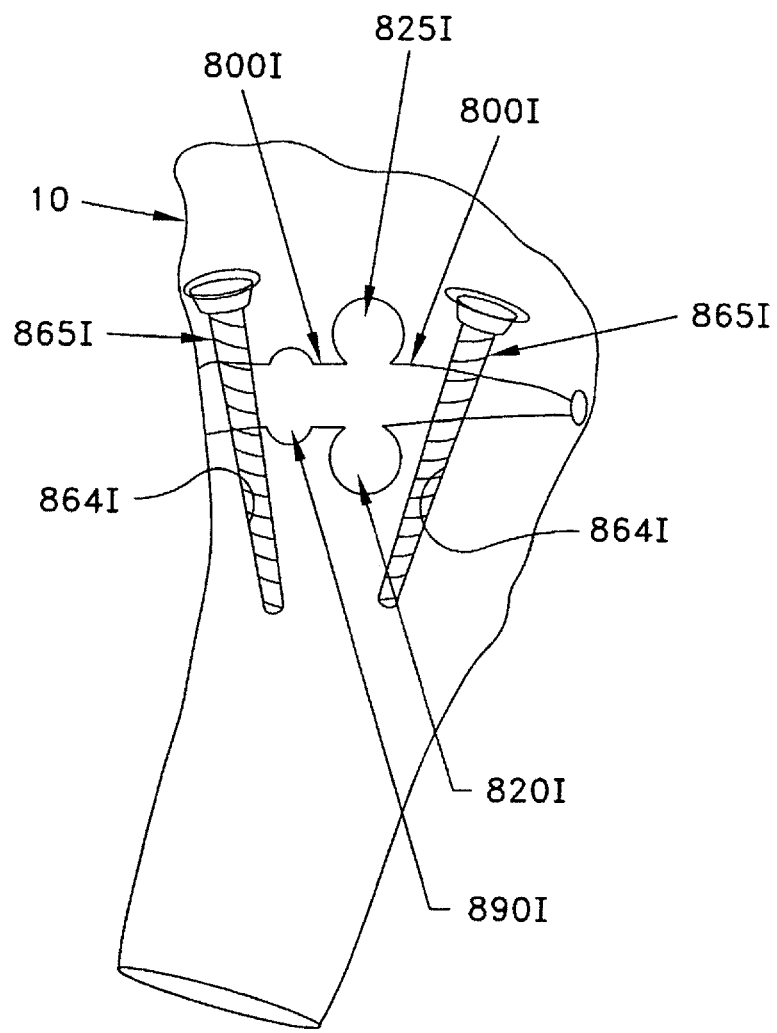
FIG. 64 is a schematic view showing still another novel implant disposed in the tibia.

Thus, for example, and looking now at FIG. 64, there is shown an implant 800I secured in tibia 10 using "toe" screws 865I. In this form of the invention, implant 800I is substantially the same as the implant 800C previously described, except that (i) implant 800I is preferably formed as a one-piece construction, and (ii) keys 820I, 825I preferably omit the screw bores 833C, 834C associated with the keys 820C, 825C of implant 800C. Again, fixation holes 864I and fixations screw 865I may pass through any portion of implant 800I, including keys 820I, 825I and/or shear rib 890I.

Figure 65:
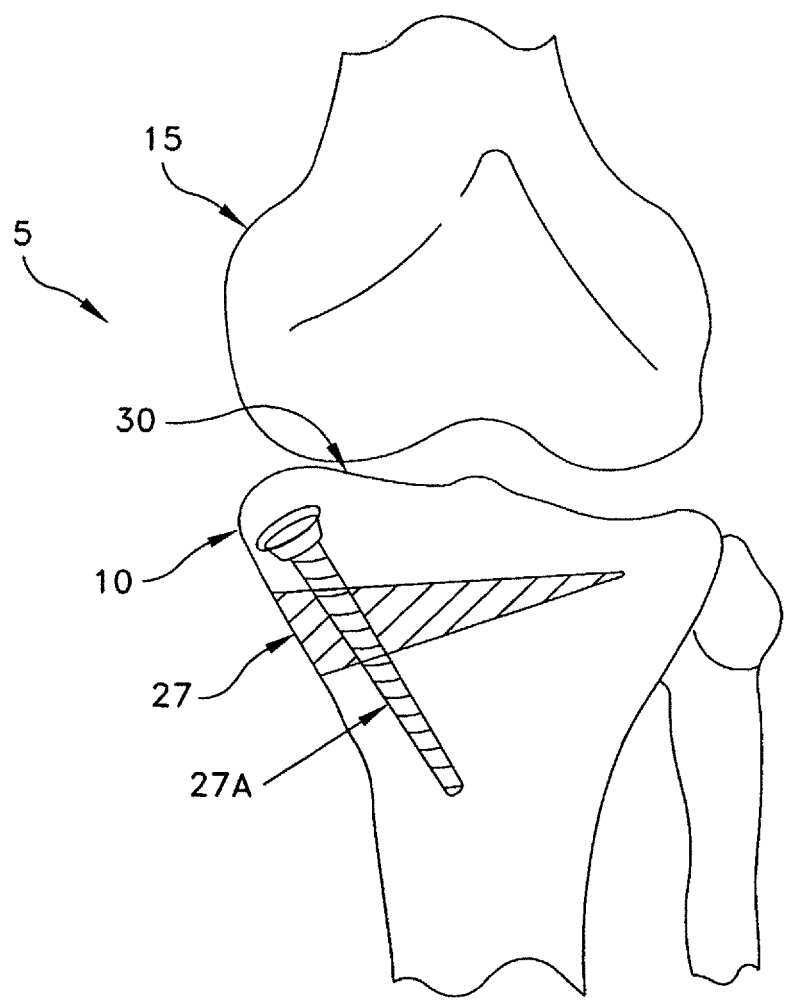
FIG. 65 is a schematic view showing yet another novel implant disposed in the tibia.
Figure 66:
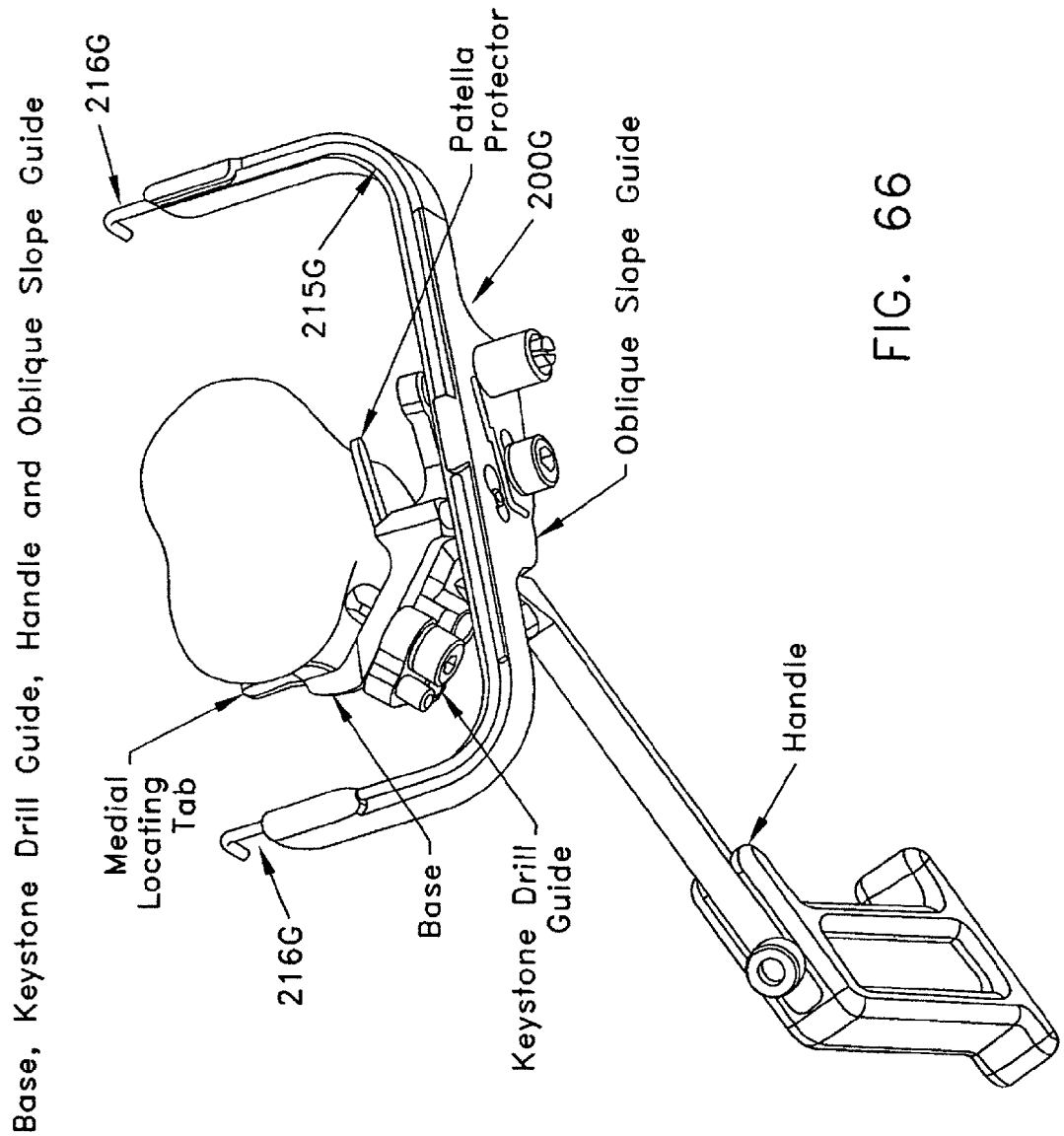
FIGS. 66-68 are schematic views showing an alternative slope guide provided in accordance with another preferred embodiment of the present invention.
Figure 67:
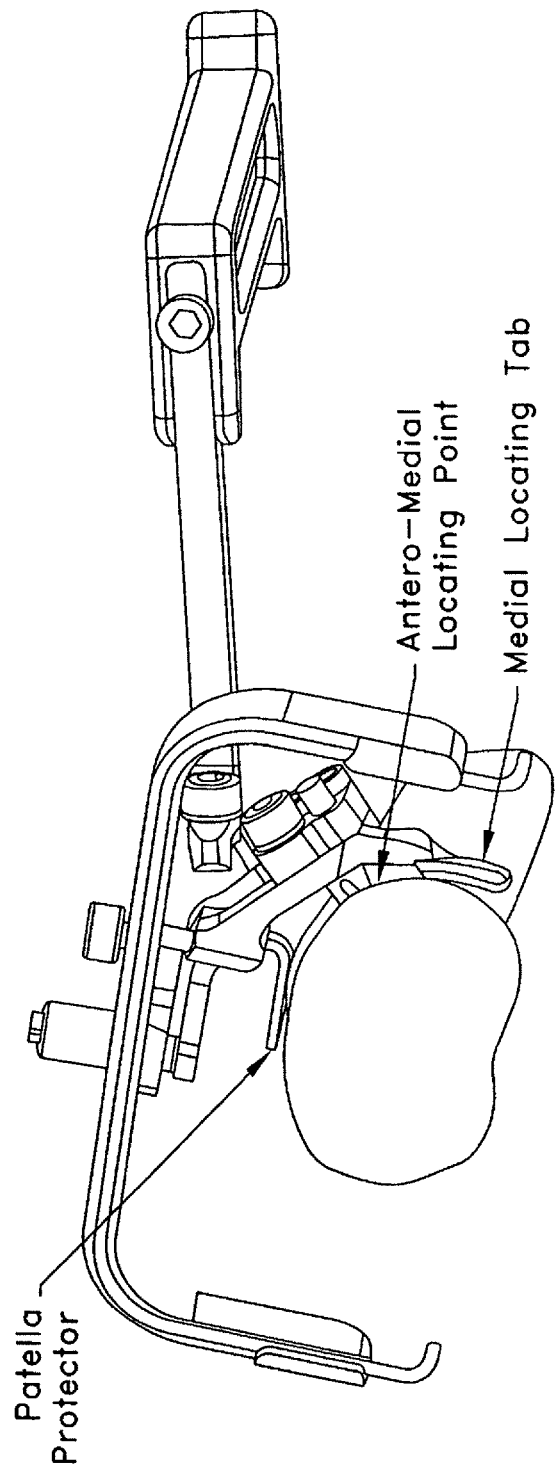
Figure 68:
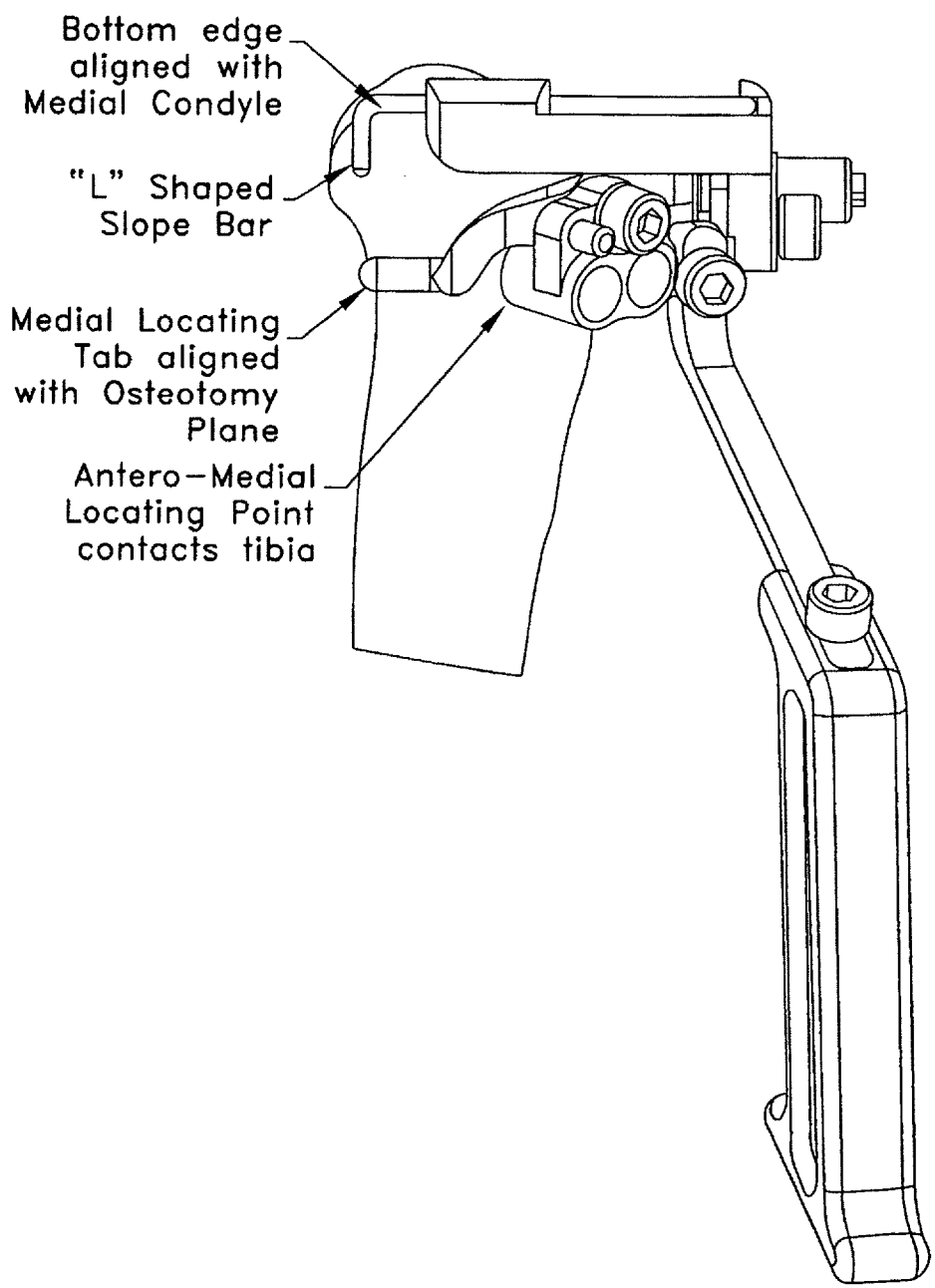

Furthermore, and looking now at FIG. 65, there is shown a "generic" wedge-shaped implant 27 secured in tibia 10 using "toe" screws 27A.

Alternative Slope Guide

Looking next at FIGS. 66-71, there is shown an alternative slope guide 200G. In this embodiment, guide element 215G of slope guide 200G is preferably formed with a "U shape" so as to provide additional functionality. More particularly, by forming guide element 215G with a "U shape", several significant advantages are obtained. First, this construction permits guide element 215G to wrap around the perimeter of the tibia. Second, the "U shape" of guide element 215G also operates to indicate if the slope guide is not vertically aligned with the level of the fluoroscope. More particularly, if slope guide 200G is not vertically aligned with the level of the fluoroscope, the "U shape" of guide element 215G will appear as a "U shape" on the fluoroscope. However, if guide element 215G is vertically aligned with the level of the fluoroscope, then the guide element will appear as a straight line on the fluoroscope. Again, this vertical alignment is important, since it enables alignment of slope guide 200G (and hence positioning guide 100) with the medial condyle, i.e., with the A-P slope plane.

Slope guide 200G may also be provided with "L-shaped" alignment tabs 216G extending from each end of slope guide 200G. "L-shaped" alignment tabs 216G operate to indicate if the slope guide is not horizontally aligned with the level of the fluoroscope. More particularly, if slope guide 200G is not horizontally aligned with the level of the fluoroscope, "L-shaped" alignment tabs 216G will appear as two distinct "L's" on the fluoroscope. However, if slope guide 200G is horizontally aligned with the level of the fluoroscope, then "L-shaped" alignment tabs 216G will appear as a single "L" on the fluoroscope.

Figure 69:
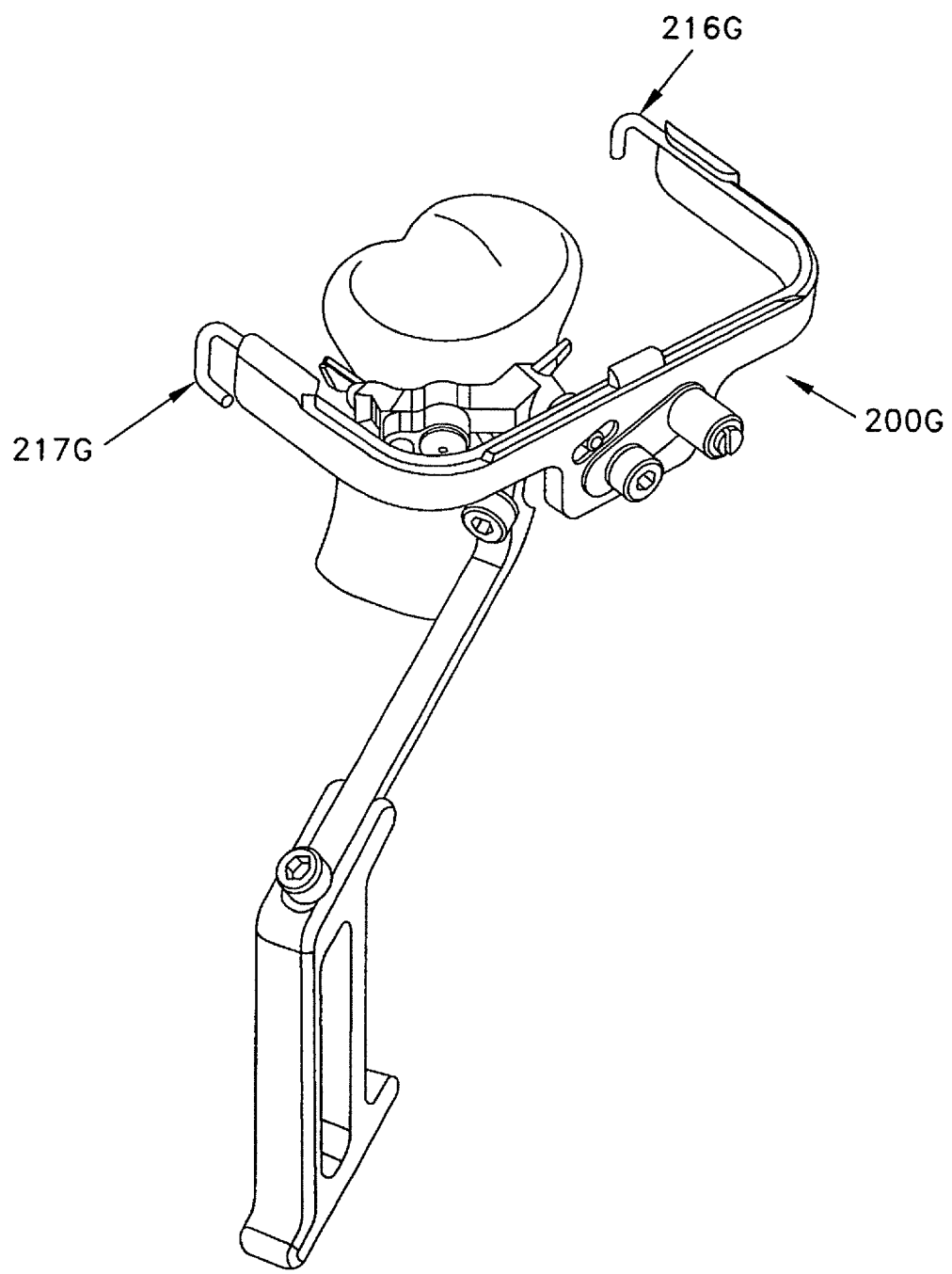
FIGS. 69-71 are schematic views showing an alternative slope guide also provided in accordance with another preferred embodiment of the present invention.
Figure 70:
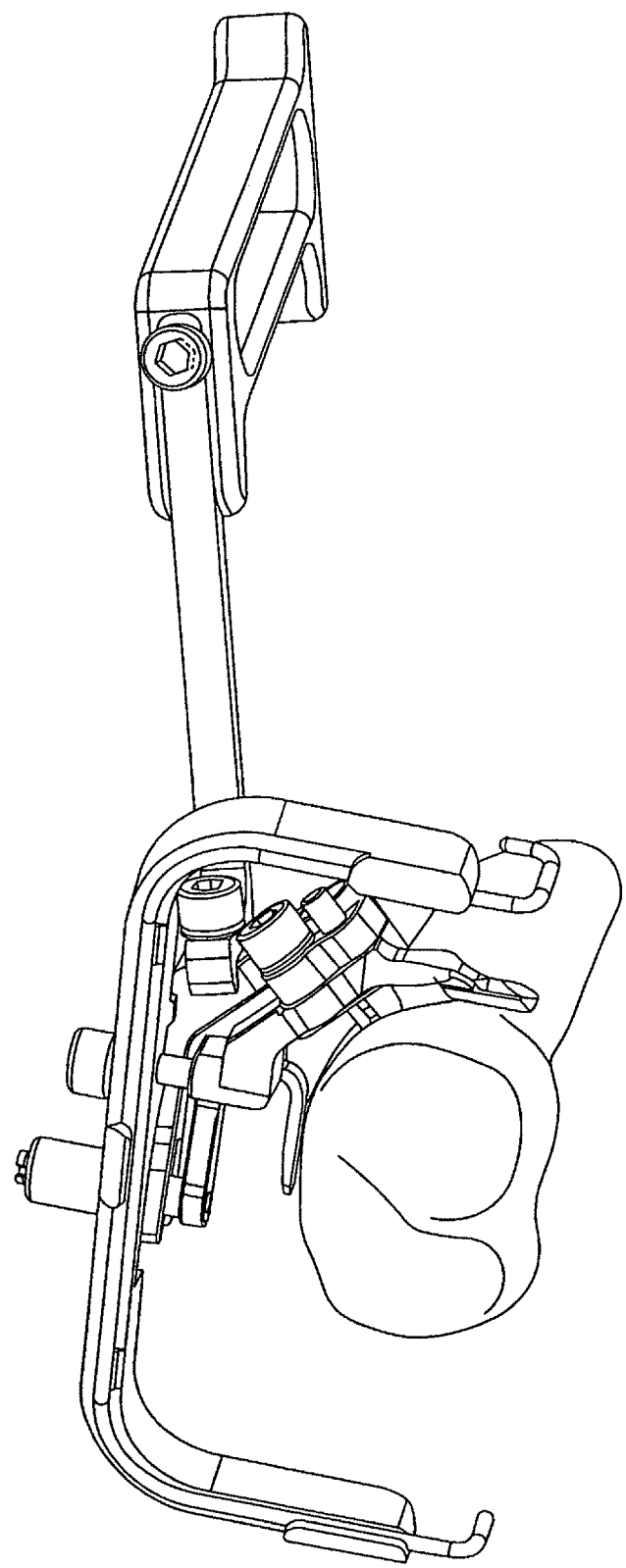
Figure 71:
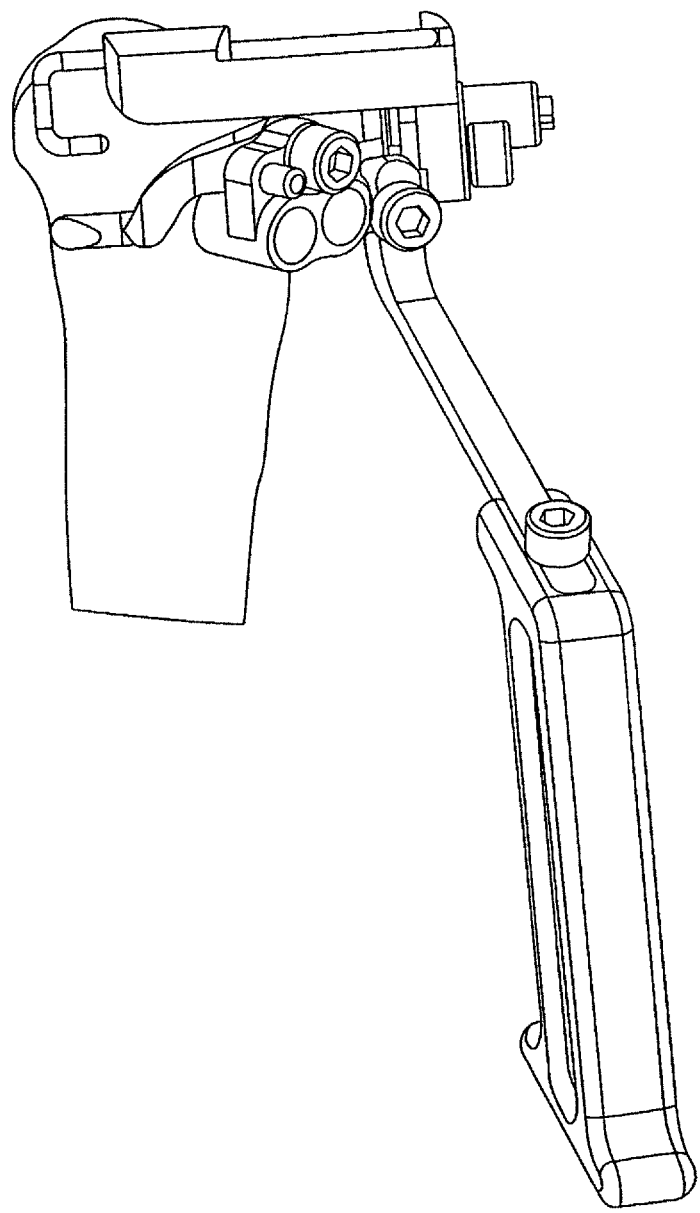

Additionally, and now looking at FIGS. 69-71, slope guide 200G may also be provided with one "L-shaped" alignment tab 216G extending from one end of slope guide and one hook 217G extending from the other end of slope guide 200G. Hook 217G allows a surgeon to differentiate between the distal and proximal ends of U-shaped slope guide 200G while being viewed under fluoroscopy.

Alternative Tibial Tubercle Locating Tab

Figure 72:
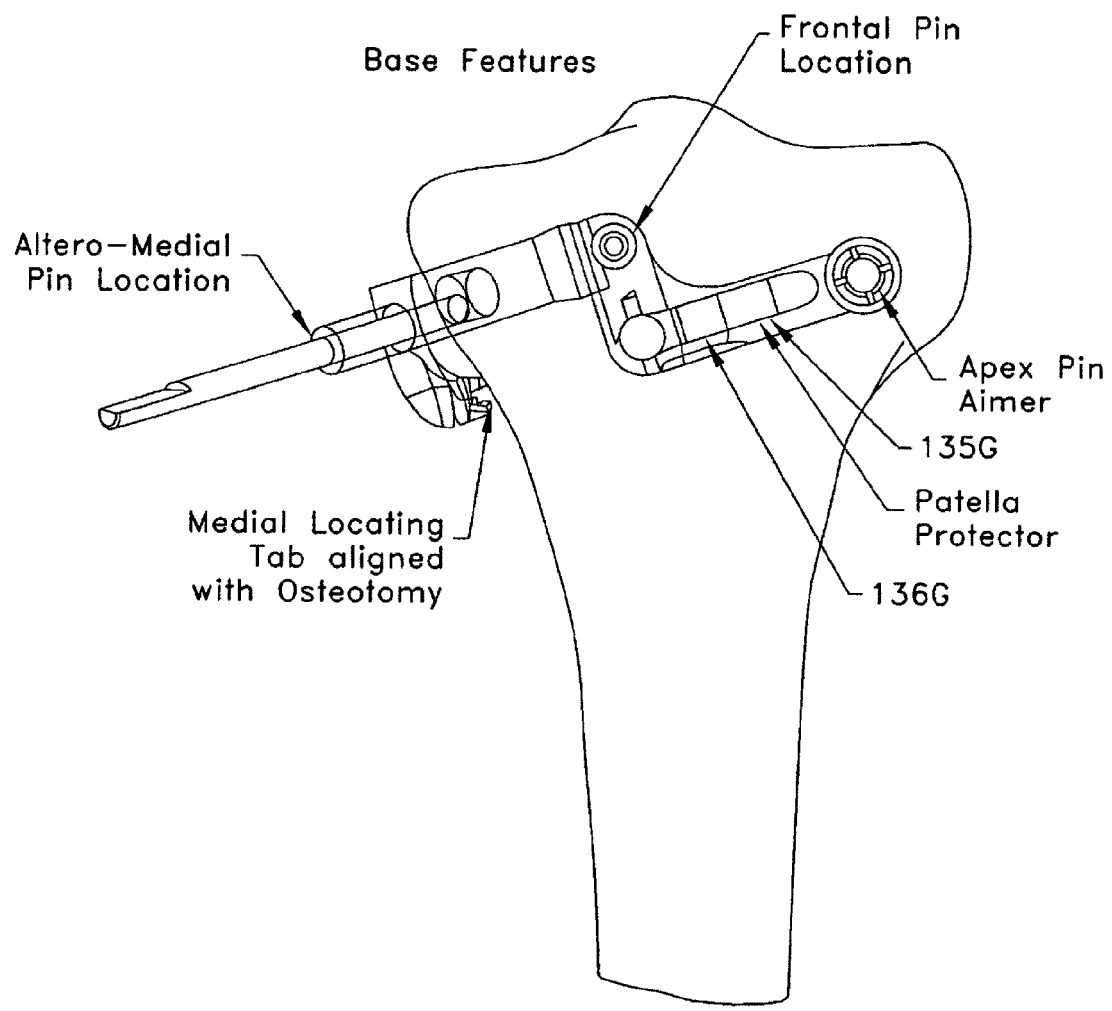
FIGS. 72 and 73 are schematic views showing an alternative tibial tubercle locating tab also provided in accordance with another preferred embodiment of the present invention.
Figure 73:
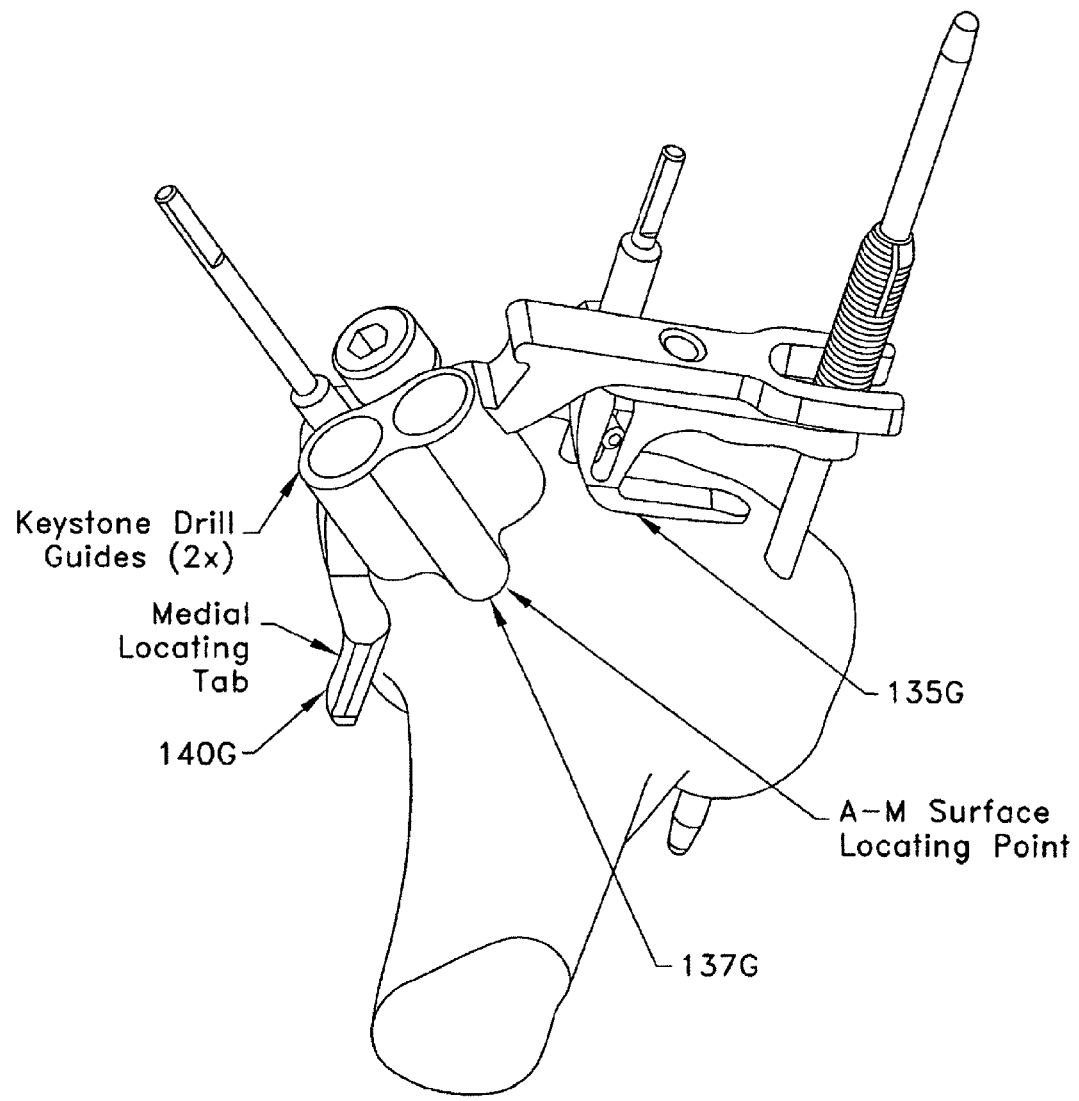

Looking next at FIGS. 72 and 73, there is shown an alternative tibial tubercle locating tab 135G. In this embodiment, tibial tubercle locating tab 135G is slidably attached to positioning guide 100. It is important to note that by forming tibial tubercle locating tab 135G so that it is slidably received in a slot 136G, tibial tubercle locating tab 135G is able to accommodate variations in tibial tubercle anatomy.

It should be appreciated that tibial tubercle locating tab 135G also functions as an anterior protector by providing a protective shield between the oscillating saw blade and the anterior soft tissue structures, e.g., the patellar tendon. Thus, tibial tubercle locating tab 135G also functions as a patellar tendon protector.

Tibial tubercle locating tab 135G also serves to position the instrumentation above the tubercle. In addition, medial locating tab 140G and A-M surface locating tab 137G position the instrumentation laterally and anterior to posterior. Thus, tibial tubercle locating tab 135G, medial locating tab 140G and A-M surface locating tab 137G help to align positioning guide 100 with the tibia.

Anterio-Lateral Osteotomies

In the foregoing description, the present invention is discussed in the context of performing an open wedge osteotomy using an antero-medial approach so as to effect a medial opening wedge osteotomy. Of course, it should be appreciated that the present invention may also be used in antero-lateral approaches so as to effect a lateral opening wedge osteotomy, or in other approaches which will be well known to those skilled in the art.

Method and Apparatus for Performing a Spherical Osteotomy

Figure 74:
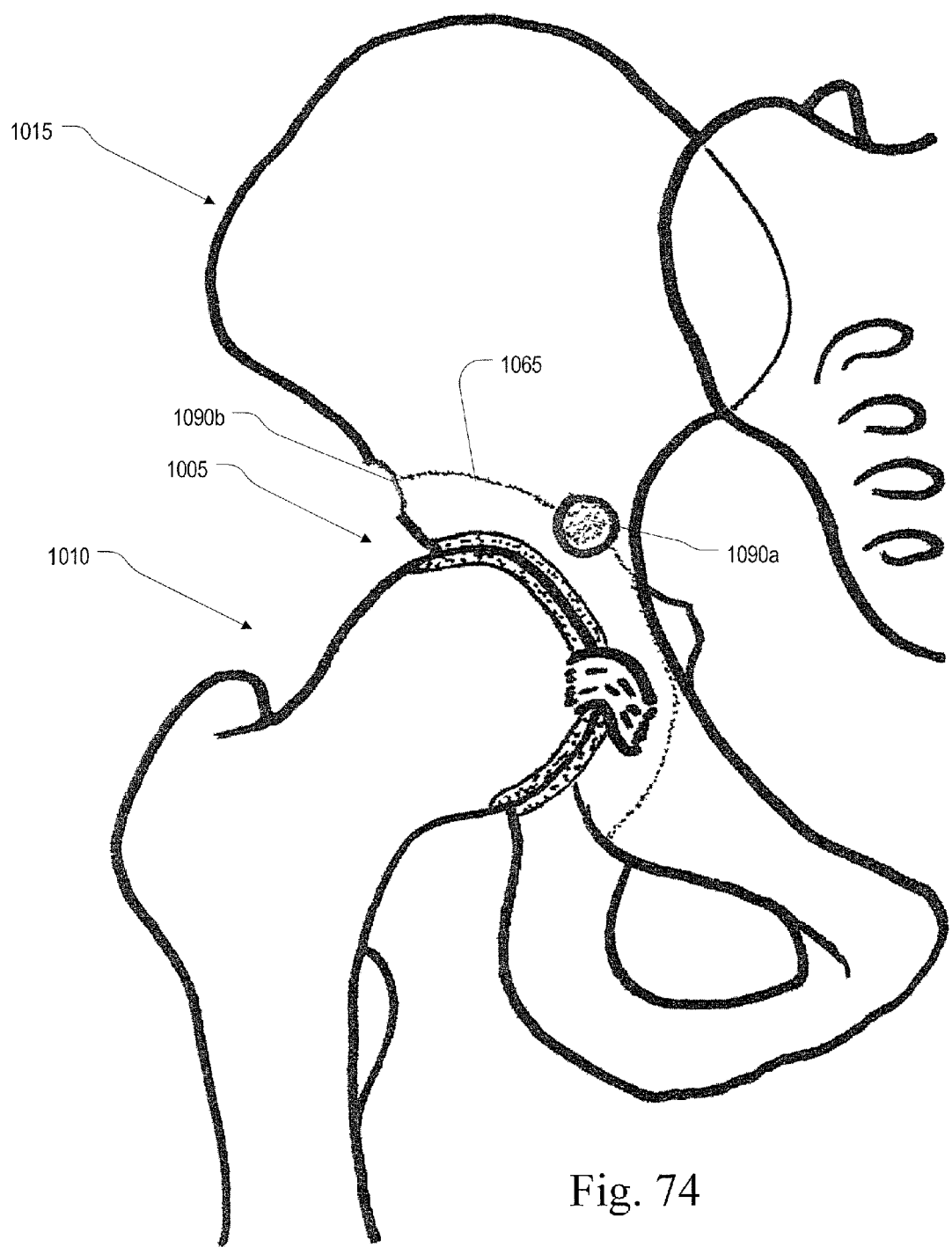
FIG. 74 shows a step in performing a spherical osteotomy according to a disclosed embodiment from an anterior view of a hip joint.
Figure 75:
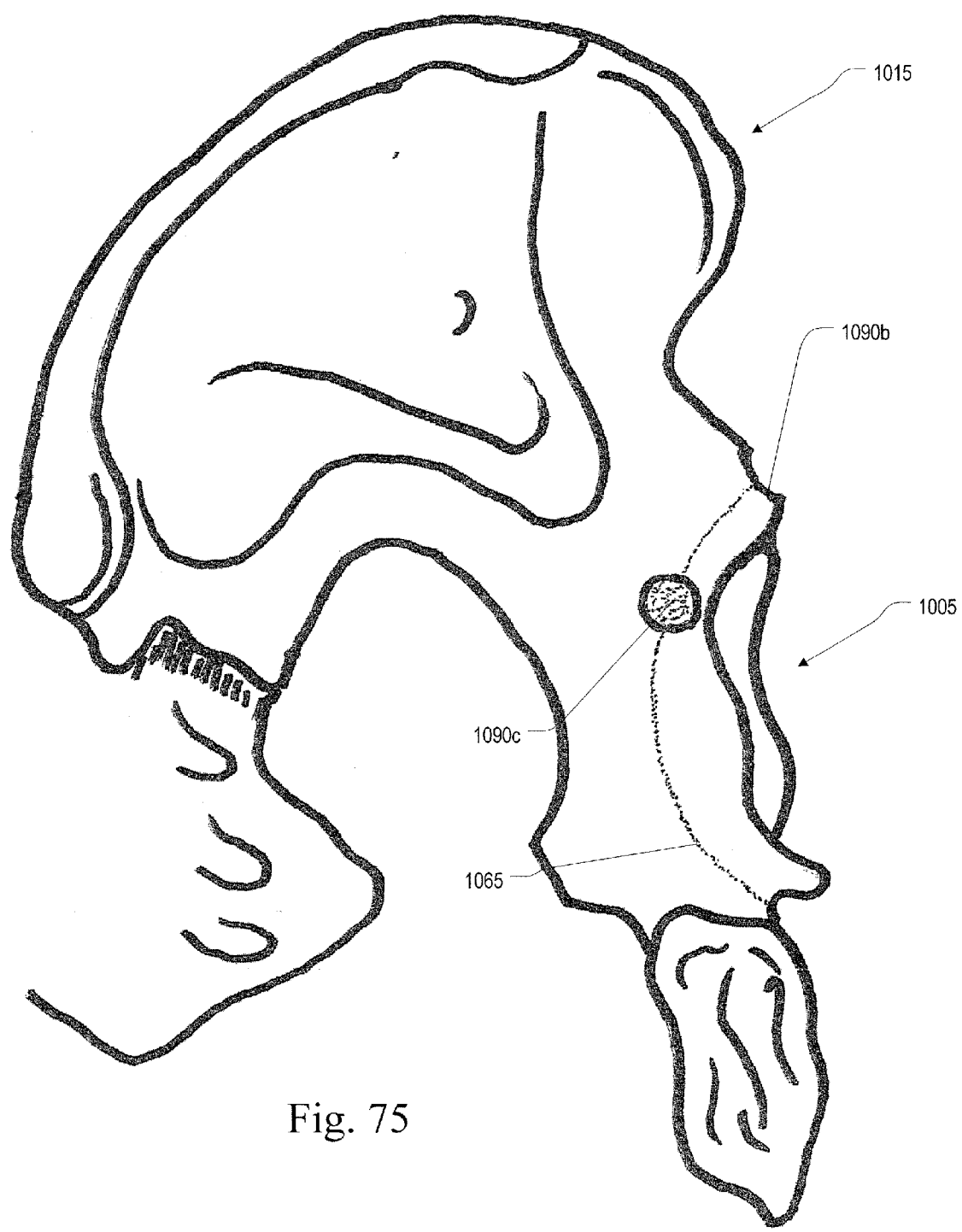
FIG. 75 shows a step in performing a spherical osteotomy according to a disclosed embodiment from a posterior-lateral view of a hip joint.

In another embodiment, any or all of the positioning guide 100 (shown in FIG. 16), slope guide 200 (shown in FIG. 11), apex pin 300 (shown in FIG. 16), keyhole drill guide 400 (shown in FIG. 18), posterior protector 500 (shown in FIG. 20), and cutting guide 600 (shown in FIG. 20) may be modified and utilized to create a spherical osteotomy, shown in FIGS. 74 and 75. FIG. 74 shows the upper femur 1010, pelvis 1015, and hip joint 1005 from an anterior view. A radial cutting plane 1065 is defined in pelvis 1015 along a cutting plane on the acetabular side of the hip joint 1005 as shown and as can be understood from the above description with respect to the tibial osteotomy.

Keyholes 1090 may be formed along the cutting plane 1065 as shown in FIG. 74 and FIG. 75, which shows the pelvis 1015 and hip joint 1005 from a posterior-lateral view. In one embodiment, the keyholes 1090a,b,c are formed around the pelvis 1015, as shown in FIGS. 74 and 75. In the embodiment shown, three keyholes 1090a,b,c are formed in the pelvis 1015, an anterior facing keyhole 1090a, a lateral facing keyhole 1090b, and a posterior facing keyhole 1090c. However, depending on the desired support for the osteotomy, more or fewer keyholes may be formed as required. The keyholes 1090a,b,c may be formed using a tapered drill bit such that the proximal diameter of the keyhole 1090a,b,c is greater than the distal diameter. In another embodiment, the keyholes 1090a,b,c may be formed as a roughly cylindrical shape.

In one embodiment, shown in FIGS. 74 and 75, the keyholes 1090a,b,c are formed such that the cutting plane 1065 transects the keyholes 1090a,b,c. In one embodiment, the transection may be such that the upper portion of the keyhole 1090a,b,c and the lower portion of the keyhole 1090a,b,c are approximately equal in side (i.e. the cutting plane 1065 may bisect the keyholes 1090a,b,c). In another embodiment, the cutting plane 1065 may transect the keyhole 1090a,b,c such that the upper and lower portions are not roughly equal in size. In another embodiment, as is shown and described above with respect to the tibial implant, the keyholes 1090a,b,c may be formed as shown above such that the cutting plane 1065 is tangential to the keyholes 1090a,b,c.

Figure 76:
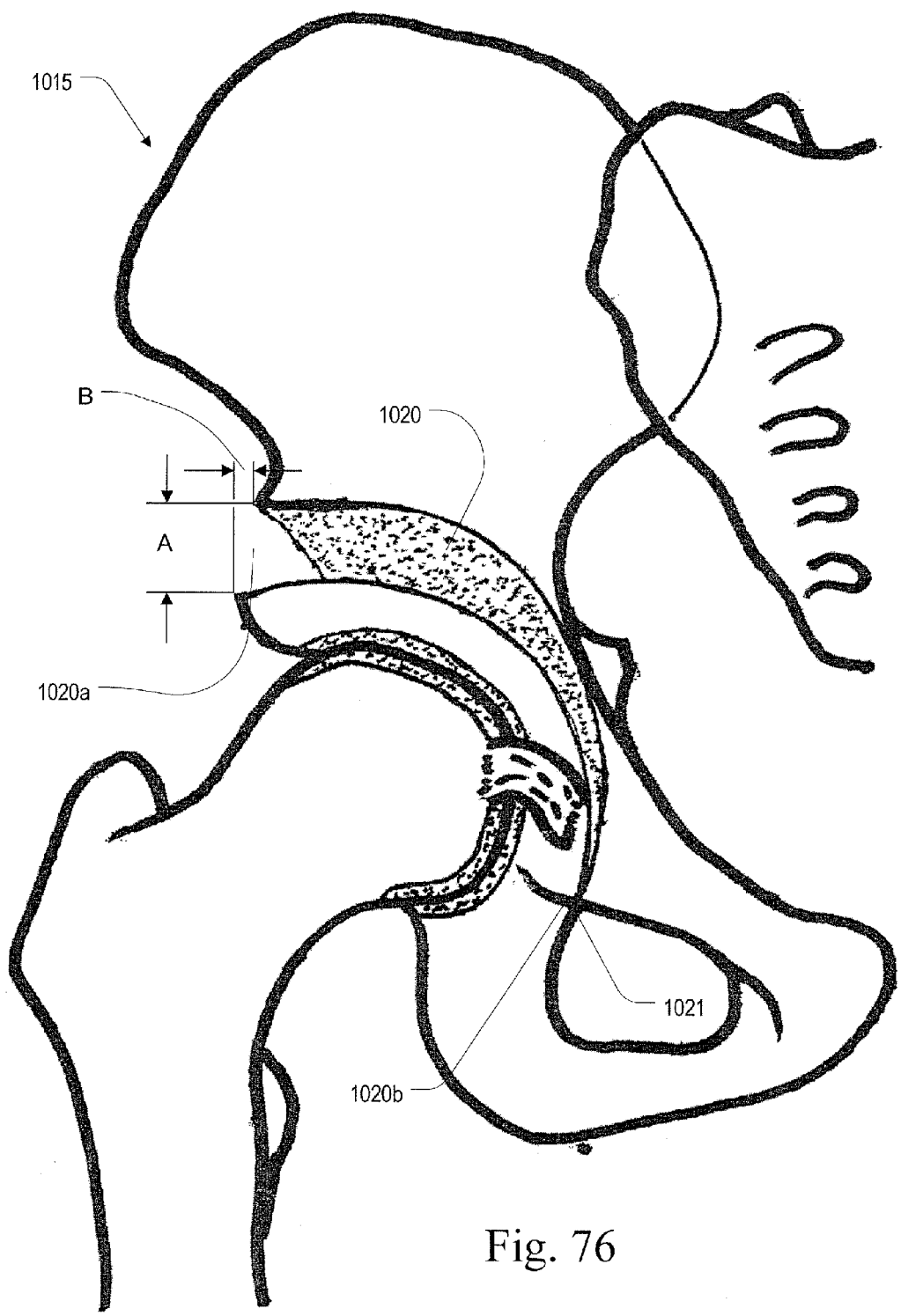
FIG. 76 shows a step in performing a spherical osteotomy according to a disclosed embodiment from an anterior view of a hip joint.

As shown next in FIG. 76, a radial cut is made along the cutting plane 1065 and the cut is widened using the fixtures and methods described above to create an opening 1020. The opening 1020 may be made either before or after the formation of the keyholes 1090a,b,c (not shown in FIG. 76). The opening 1020 is widened at a proximal end 1020a of the opening 1020. In one embodiment, the opening 1020 is formed such that a bony hinge 1021 remains at the distal end 1020b of the opening 1020. If desired, an apex pin according to the embodiments described above may be utilized to define the bony hinge 1021. In another embodiment, the opening 1020 is formed completely through the pelvis 1015. The opening 1020 is widened in order to create a desired vertical correction A and a desired lateral correction B. Depending on the desired vertical correction A and lateral correction B, the distal end 1020b of the cut may be located at any point within the pelvis 1015 or may terminate at the opposing side of the pelvis 1015 from which the opening 1020 began.

Figure 77:
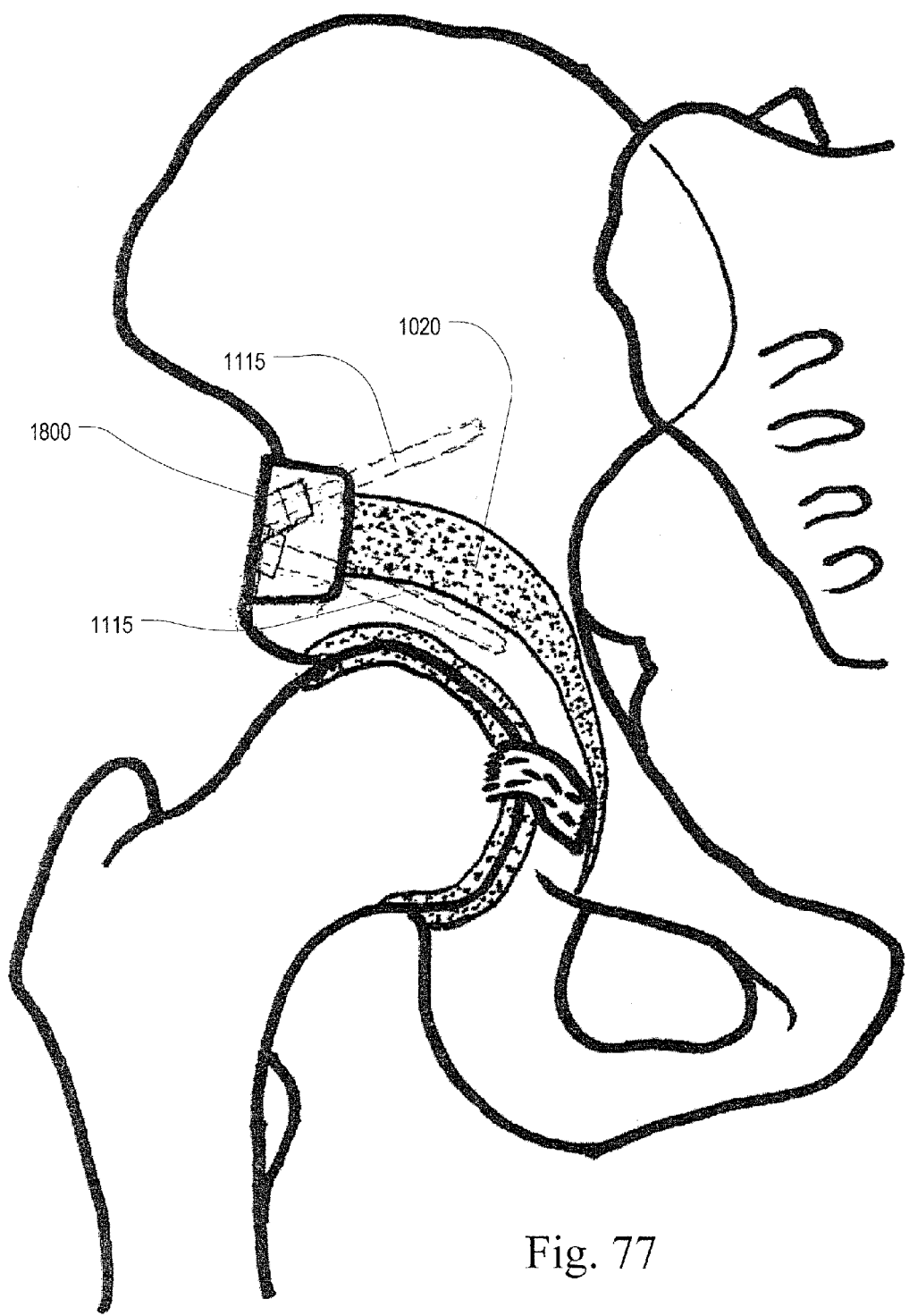
FIG. 77 shows a step in performing a spherical osteotomy according to a disclosed embodiment from an anterior view of a hip joint.

Once the opening 1020 is widened to the desired correction, a keyhole implant 1800 according to one embodiment is inserted into the opening 1020 and lateral keyhole 1090b as shown in FIG. 77 to stabilize the opening 1020. Fasteners 1115 may then be inserted though the keyhole implant 1800 and into the upper and lower portions of the pelvis 1015 that were defined by the opening 1020 in order to fix the implant in place and further stabilize the opening 1020. The fasteners 1115 may be any suitable fixation element and include, but are not limited to, the fixation screws described above.

Figure 78:
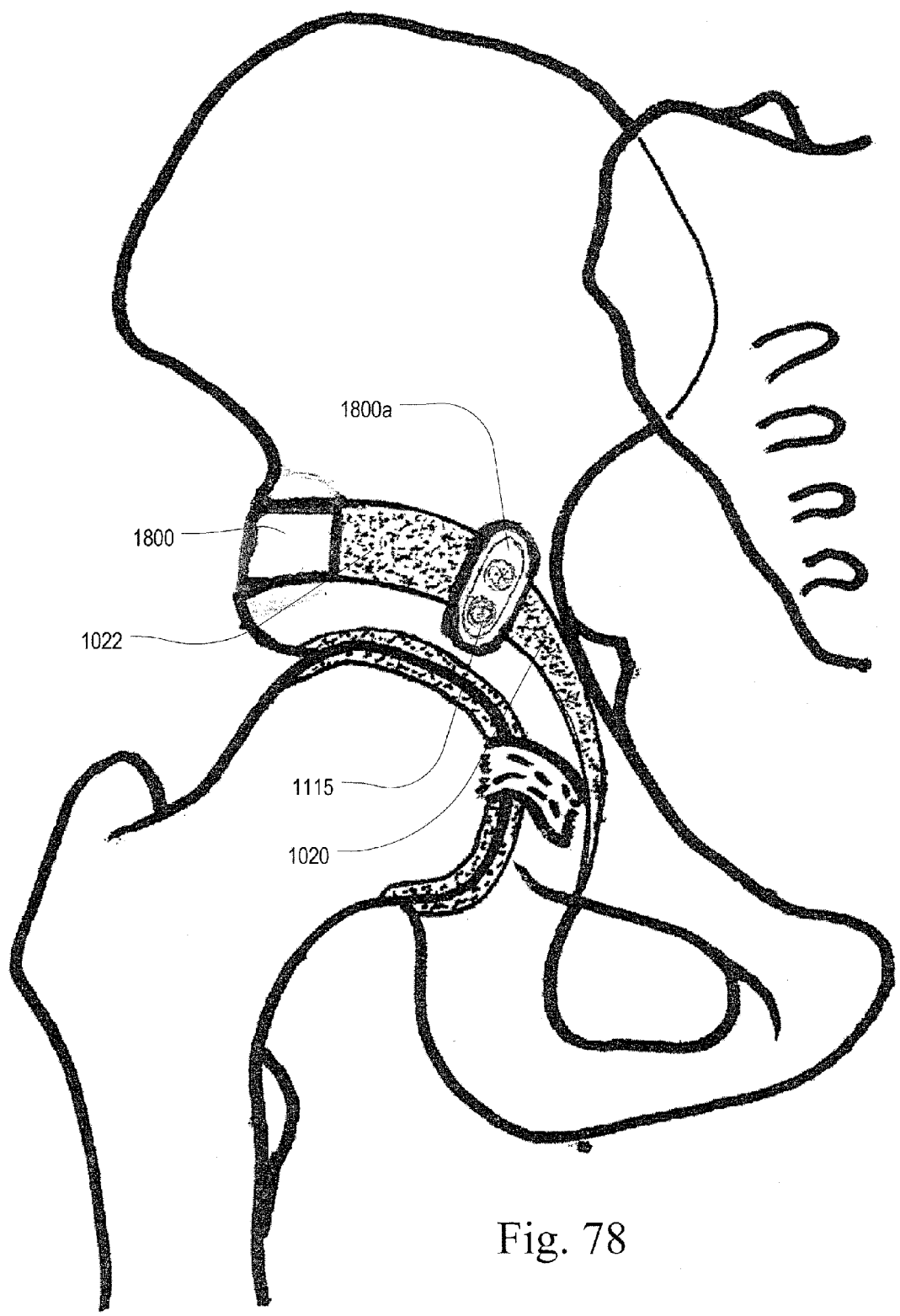
FIG. 78 shows a step in performing a spherical osteotomy according to a disclosed embodiment from an anterior view of a hip joint.
Figure 79:
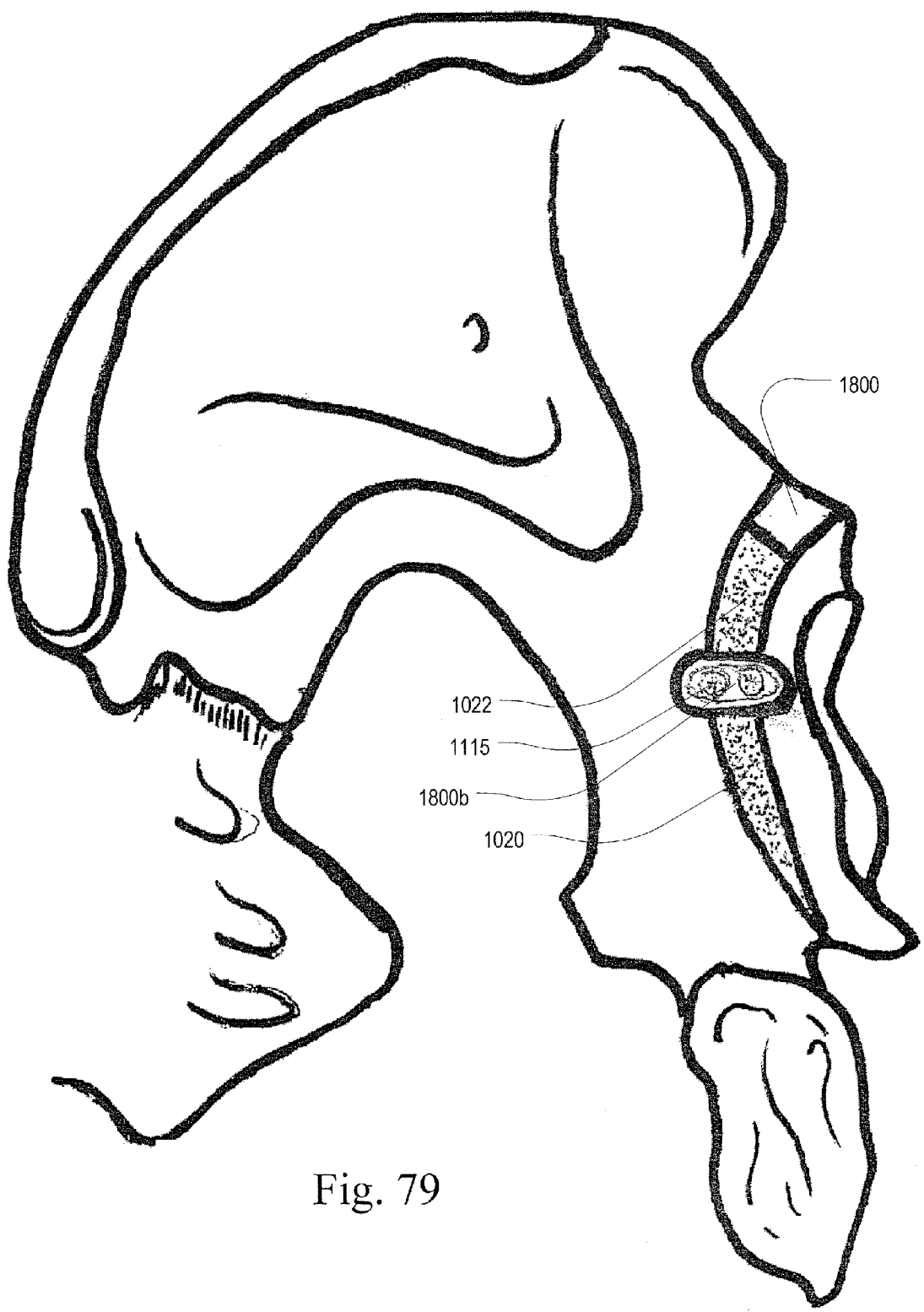
FIG. 79 shows a step in performing a spherical osteotomy according to a disclosed embodiment from a posterior-lateral view of a hip joint.

Other keyhole implants 1800a,b may be inserted into the anterior and posterior keyholes 1090a,c as shown in FIGS. 78 and 79. These provide further stability to the opening 1020 to prevent the opening from collapsing, stabilize the opening 1020 while healing, and provide support in the anterior-posterior direction. As can be understood, the keyhole implants 1800a,b are sized according to the desired corrections shown in FIG. 76. Once the keyhole implants 1800a,b,c are positioned in place fasteners 1115 can be inserted through the implants a,b,c and into the upper and/or lower surfaces of the opening 1020 to stabilize the keyhole implants 1800a,b,c. After the keyhole implants 1800a,b,c have been fixed in place as desired, a graft material 1022 (e.g., bone paste, bone cement, etc.) may be positioned within the interior of the opening 1020 in order to provide additional support and speed healing.

FIGS. 80 and 81 show the keyhole implant 1800a, as shown in FIG. 78. In this embodiment, the keyhole implant (e.g. 1800a) has an upper key 1865a and lower key 1865b that are configured to engage the upper portion of the keyhole and lower portion of the keyhole respectively. The body 1810 of the implant fits into the opening 1020 and acts to space the upper key 1865a from the lower key 1865b.

As is shown in FIGS. 80 and 81 the keyhole implant 1800a may have a taper from proximal to distal end to provide the desired spacing in the opening 1020 as shown and described above. Internal bores 1120 may be provided in the keyhole implant 1800a in order to permit insertion of fasteners through the keyhole implant 1800a and into the bone above and below the keyhole implant 1800a to permit securing the keyhole implant 1800a in place within the opening 1020 as described above. The keyhole implant 1800a may also be provided a counterbore 1811 to permit the fasteners that are inserted through the internal bores 1120 are inset within the keyhole implant 1800a. Once the implant 1800a is installed, the counterbore 1811 may be filled with a graft material as described above to speed healing.

Figure 82:
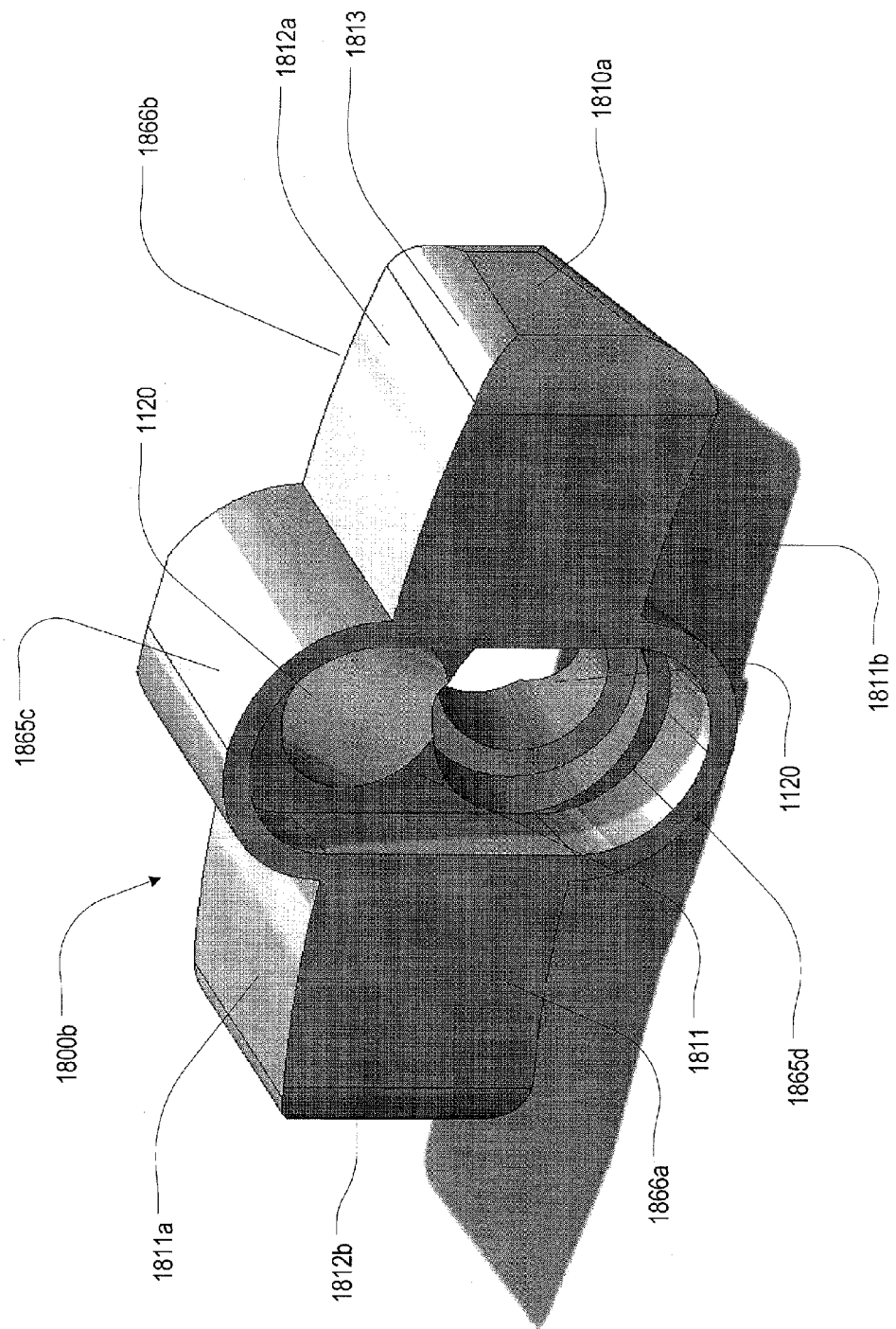
FIG. 82 shows an implant for performing a spherical osteotomy.

FIG. 82 shows a keyhole implant 1800b according to another embodiment. The keyhole implant 1800b may be used at the lateral keyhole 1890b, shown in FIGS. 74 and 75. In one embodiment, the keyhole implant 1800b is provided such that the upper key 1865c and lower key 1865d are square to the proximal surface 1866a of the implant 1800b (i.e. the keyhole implant 1800b is not tapered as the keyhole implant 1800a was). The body 1810a may also be tapered from proximal to distal end of the implant 1800b as shown in FIG. 82. In another embodiment, the upper and lower keys 1865c,d may be tapered from proximal to distal end as was shown in FIGS. 80 and 81. In another embodiment, the body 1810a may be configured such that the upper body surface 1811a and lower body surface 1811b are square to the proximal surface 1866a of the keyhole implant 1800b.

In the embodiment shown in FIG. 82, the keyhole implant 1800b is provided two arms 1812a,b that are configured to be inserted into the opening 1020. The arms 1812a,b provide stability to the opening 1020 to prevent the opening 1020 from shift in the anterior-posterior direction and to provide additional strength to prevent the opening 1020 from collapsing. The upper and lower body surfaces 1811a,b are thus configured to support the upper and lower surfaces of the opening 1020. Similar to the keyhole implant 1800a shown in FIGS. 80 and 81, the keyhole implant 1800b may be provided internal bores 1120 to receive fasteners and secure the implant 1800b to the upper and lower bone surfaces defined by the cut. The keyhole implant 1800b may also be provided a counterbore 1811, as described above. In one embodiment, the arms 1812a,b are provided a radius 1813 on one or more of the upper surface 1811a, lower surface 1811b, proximal end 1866a, and distal end 1866b at the lateral extent of each arm 1812a,b.

In another embodiment, each arm 1812a,b of the keyhole implant 1800b may be tapered from medial to lateral or lateral to medial to allow the keyhole implant 1800b to be utilized in the anterior and posterior keyholes 1890a,b shown in FIGS. 74 and 75. This will provide the keyhole implant 1800b with a wedge-shape as described above with respect to the tibial implant described above. The taper of the arms 1812a,b from medial to lateral or lateral to medial will depend on if the keyhole implant 1800b is to be inserted into the anterior or posterior keyholes 1890a,b shown in FIGS. 74 and 75.

Modifications

While several embodiments have been described in detail, it should be readily understood that the invention is not limited to the disclosed embodiments. Rather the embodiments can be modified to incorporate any number of variations, alterations, substitutions, or equivalent arrangements not heretofore described. Although certain features have been described with some embodiments of the osteotomy systems, apparatuses, and methods, such features can be employed in other embodiments of the osteotomy systems, apparatuses, and methods as well. Accordingly, the invention is not limited by the foregoing description, but is only limited by the scope of the appended claims. Further, it is understood that many changes in the details, materials, steps and arrangements of parts, which have been herein described and illustrated in order to explain the nature of the invention, may be made by those skilled in the art without departing from the principles and scope of the present invention.

What is claimed is:

1. A method for performing an osteotomy, the method comprising:
    cutting a bone along a substantially radial cutting plane;
    forming a first keyhole in the bone adjacent to the cutting plane;
    moving the bone on either side of the cut apart so as to form an opening in the bone; and
    positioning a first implant in the opening created in the bone, wherein the first implant comprises at least one key, and further wherein the at least one key is disposed in the first keyhole formed in the bone.

2. The method according to claim 1, wherein the cutting plane is at an acetabular side of a hip joint.

3. The method according to claim 1, wherein the opening is a substantially spherical osteotomy opening.

4. The method according to claim 1, further comprising forming a second keyhole and a third keyhole in the bone adjacent the cutting plane.

5. The method according to claim 4, wherein the first keyhole faces a substantially lateral direction, the second keyhole faces a substantially posterior direction, and the third keyhole faces a substantially anterior direction.

6. The method according to claim 1, further comprising:
    providing a second implant comprising a second key in the opening such that the second key engages the second keyhole; and
    providing a third implant comprising a third key in the opening such that the third key engages the third keyhole.

7. The method according to claim 1, wherein the cutting plane transects the keyhole.

8. The method according to claim 1, wherein the cutting plane bisects the keyhole.

9. The method according to claim 1, wherein the cutting plane is tangential to the keyhole.

10. The method according to claim 1, wherein the key includes an interior bore for receiving a fastener.

11. The method according to claim 10, wherein the interior bore is angled so as to direct the fastener into the adjacent bone.

12. The method according to claim 1, wherein the key includes external ribs to facilitate fixation.

13. The method according to claim 1, wherein the implant includes at least two interior bores for receiving a fastener.

14. A method for performing an osteotomy, the method comprising:
   cutting a bone along a cutting plane, wherein the bone is a pelvis;
   forming a first keyhole in the bone adjacent to the cutting plane;
   moving the bone on either side of the cut apart so as to form an opening in the bone; and
   positioning a first implant in the opening created in the bone, wherein the first implant comprises at least one key, and further wherein the at least one key is disposed in the first keyhole formed in the bone.

15. The method according to claim 14, wherein the step of cutting along the cutting plane terminates the cut within the pelvis to define a bony hinge at a distal end of the cut.

16. The method according to claim 14, wherein the cut is formed entirely through the pelvis.

17. The method according to claim 14, wherein the opening is a substantially spherical osteotomy opening.

18. The method according to claim 14, further comprising forming a second keyhole and a third keyhole in the bone adjacent the cutting plane.

19. The method according to claim 18, wherein the first keyhole faces a substantially lateral direction, the second keyhole faces a substantially posterior direction, and the third keyhole faces a substantially anterior direction.

20. The method according to claim 18, further comprising:
   providing a second implant comprising a second key in the opening such that the second key engages the second keyhole; and
   providing a third implant comprising a third key in the opening such that the third key engages the third keyhole.

21. The method according to claim 14, wherein the cutting plane transects the keyhole.

22. The method according to claim 14, wherein the cutting plane bisects the keyhole.

23. The method according to claim 14, wherein the cutting plane is tangential to the keyhole.

24. The method according to claim 14, wherein the key includes an interior bore for receiving a fastener.

25. The method according to claim 24, wherein the interior bore is angled so as to direct the fastener into the adjacent bone.

26. The method according to claim 14, wherein the key includes external ribs to facilitate fixation.

27. The method according to claim 14, wherein the implant includes at least two interior bores for receiving a fastener.

* * * * *